(12) United States Patent
Li et al.

(10) Patent No.: US 12,188,055 B2
(45) Date of Patent: *Jan. 7, 2025

(54) ENGINEERED GLUCOSYLTRANSFERASES

(71) Applicant: NUTRITION & BIOSCIENCES USA 4, INC., Rochester, NY (US)

(72) Inventors: Yougen Li, Glen Mills, PA (US); Ellen D. Semke, Newark, DE (US); Qiong Cheng, Wilmington, DE (US); Jian Ping Lai, Wallingford, PA (US)

(73) Assignee: NUTRITION & BIOSCIENCES USA 4, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/157,512

(22) Filed: Jan. 20, 2023

(65) Prior Publication Data
US 2023/0392128 A1 Dec. 7, 2023

Related U.S. Application Data

(63) Continuation of application No. 17/118,733, filed on Dec. 11, 2020, now Pat. No. 11,560,551, which is a continuation of application No. 16/127,293, filed on Sep. 11, 2018, now Pat. No. 10,865,393.

(60) Provisional application No. 62/557,840, filed on Sep. 13, 2017.

(51) Int. Cl.
*C12N 9/10* (2006.01)
*C08B 37/00* (2006.01)
*C12N 15/56* (2006.01)
*C12P 19/04* (2006.01)
*C12P 19/18* (2006.01)
*G16B 25/00* (2019.01)

(52) U.S. Cl.
CPC ........ *C12N 9/1048* (2013.01); *C08B 37/0009* (2013.01); *C12N 9/1051* (2013.01); *C12P 19/04* (2013.01); *C12P 19/18* (2013.01); *C12Y 204/01005* (2013.01); *C12Y 204/01* (2013.01); *G16B 25/00* (2019.02)

(58) Field of Classification Search
None
See application file for complete search history.

(56) References Cited

U.S. PATENT DOCUMENTS

| | | | | |
|---|---|---|---|---|
| 10,301,604 B2 * | 5/2019 | Li | | C08B 37/0009 |
| 10,865,393 B2 * | 12/2020 | Li | | C08B 37/0009 |
| 11,028,373 B2 * | 6/2021 | Li | | C12N 9/1051 |
| 11,560,551 B2 * | 1/2023 | Li | | C12N 9/1051 |
| 2014/0087431 A1 * | 3/2014 | Payne | | C12P 19/04 |
| | | | | 435/97 |
| 2018/0072998 A1 * | 3/2018 | Li | | C08B 37/0009 |

OTHER PUBLICATIONS

UniProt Database Accession No. T0TT57, Sep. 2016, 2 pages (Year: 2016).*

* cited by examiner

*Primary Examiner* — David Steadman

(57) ABSTRACT

Disclosed herein are glucosyltransferases with modified amino acid sequences. Such engineered enzymes exhibit improved alpha-glucan product yields and/or lower leucrose yields, for example. Further disclosed are reactions and methods in which engineered glucosyltransferases are used to produce alpha-glucan.

20 Claims, No Drawings

Specification includes a Sequence Listing.

ENGINEERED GLUCOSYLTRANSFERASES

This application is a continuation of U.S. application Ser. No. 17/118,733 (filed Dec. 11, 2020, now U.S. patent Ser. No. 11/560,551), which is a continuation of U.S. application Ser. No. 16/127,293 (filed Sep. 11, 2018, now U.S. patent Ser. No. 10/865,393), which claims the benefit of U.S. Provisional Application No. 62/557,840 (filed Sep. 13, 2017), all of which prior applications are incorporated herein by reference in their entirety.

FIELD

The present disclosure is in the field of enzyme catalysis. For example, the disclosure pertains to glucosyltransferase enzymes with modified amino acid sequences. Such modified enzymes have improved product yield properties, for example.

REFERENCE TO SEQUENCE LISTING SUBMITTED ELECTRONICALLY

The official copy of the sequence listing has been submitted electronically via EFS-Web or Patent Center as a file named CL6613USCNT2_SequenceListing.xml created on Aug. 24, 2023 and having a size of about 147000 bytes. The sequence listing contained in this file is part of the specification and is herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from Streptococcus salivarius (Simpson et al., Microbiology 141:1451-1460, 1995). Also for example, U.S. Pat. No. 7,000,000 disclosed the preparation of a spun fiber from enzymatically produced alpha-1,3-glucan. Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages.

While these and other advances have been made in producing glucan polymers using glucosyltransferase enzymes, less attention appears to have been drawn to improving the glucan yields of such enzymes. Addressing this technological gap, disclosed herein are glucosyltransferases engineered to have modified amino acid sequences endowing these enzymes with enhanced glucan production properties.

SUMMARY

In one embodiment, the present disclosure concerns a non-native glucosyltransferase comprising at least two amino acid substitutions at positions corresponding with amino acid residues Gln-588, Phe-607, or Arg-741 of SEQ ID NO:62, wherein the non-native glucosyltransferase synthesizes alpha-glucan comprising 1,3-linkages, and wherein the non-native glucosyltransferase has: (i) an alpha-glucan yield that is higher than the alpha-glucan yield of a second glucosyltransferase that only differs from the non-native glucosyltransferase at the substitution positions, and/or (ii) a leucrose yield that is lower than the leucrose yield of the second glucosyltransferase.

In another embodiment, the present disclosure concerns a polynucleotide comprising a nucleotide sequence encoding a non-native glucosyltransferase as presently disclosed, optionally wherein one or more regulatory sequences are operably linked to the nucleotide sequence, and preferably wherein the one or more regulatory sequences include a promoter sequence.

In another embodiment, the present disclosure concerns a reaction composition comprising water, sucrose, and a non-native glucosyltransferase as presently disclosed.

In another embodiment, the present disclosure concerns a method of producing alpha-glucan comprising: (a) contacting at least water, sucrose, and a non-native glucosyltransferase enzyme as presently disclosed, whereby alpha-glucan is produced; and b) optionally, isolating the alpha-glucan produced in step (a).

In another embodiment, the present disclosure concerns a method of preparing a polynucleotide sequence encoding a non-native glucosyltransferase, the method comprising: (a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes alpha-glucan comprising 1,3-linkages; and (b) modifying the polynucleotide sequence identified in step (a) to substitute at least two amino acids of the parent glucosyltransferase at positions corresponding with amino acid residues Gln-588, Phe-607 or Arg-741 of SEQ ID NO:62, thereby providing a polynucleotide sequence encoding a non-native glucosyltransferase that has: (i) an alpha-glucan yield that is higher than the alpha-glucan yield of the parent glucosyltransferase, and/or (ii) a leucrose yield that is lower than the leucrose yield of the parent glucosyltransferase.

BRIEF DESCRIPTION OF THE SEQUENCES

TABLE 1

Summary of Nucleic Acid and Protein SEQ ID Numbers[b]

| Description | Nucleic acid SEQ ID NO. | Protein SEQ ID NO. |
| --- | --- | --- |
| GTF 0874, Streptococcus sobrinus. The first 156 amino acids of the protein are deleted compared to GENBANK Identification No. 450874; a start methionine is included. | 1 [a] | 2 (1435 aa) |
| GTF 6855, Streptococcus salivarius SK126. The first 178 amino acids of the protein are deleted compared to GENBANK Identification No. 228476855 (Acc. No. ZP_04061500.1); a start methionine is included. | 3 [a] | 4 (1341 aa) |

TABLE 1-continued

Summary of Nucleic Acid and Protein SEQ ID Numbers[b]

| Description | Nucleic acid SEQ ID NO. | Protein SEQ ID NO. |
|---|---|---|
| GTF 2379, *Streptococcus salivarius*. The first 203 amino acids of the protein are deleted compared to GENBANK Identification No. 662379; a start methionine is included. | 5 [a] | 6 (1247 aa) |
| GTF 7527 or GTFJ, *Streptococcus salivarius*. The first 42 amino acids of the protein are deleted compared to GENBANK Identification No. 47527; a start methionine is included. | 7 [a] | 8 (1477 aa) |
| GTF 1724, *Streptococcus downei*. The first 162 amino acids of the protein are deleted compared to GENBANK Identification No. 121724; a start methionine is included. | 9 [a] | 10 (1436 aa) |
| GTF 0544, *Streptococcus mutans*. The first 164 amino acids of the protein are deleted compared to GENBANK Identification No. 290580544; a start methionine is included. | 11 [a] | 12 (1313 aa) |
| GTF 5926, *Streptococcus dentirousetti*. The first 144 amino acids of the protein are deleted compared to GENBANK Identification No. 167735926; a start methionine is included. | 13 [a] | 14 (1323 aa) |
| GTF 4297, *Streptococcus oralis*. The first 228 amino acids of the protein are deleted compared to GENBANK Identification No. 7684297; a start methionine is included. | 15 [a] | 16 (1348 aa) |
| GTF 5618, *Streptococcus sanguinis*. The first 223 amino acids of the protein are deleted compared to GENBANK Identification No. 328945618; a start methionine is included. | 17 [a] | 18 (1348 aa) |
| GTF 2765, unknown *Streptococcus* sp. C150. The first 193 amino acids of the protein are deleted compared to GENBANK Identification No. 322372765; a start methionine is included. | 19 [a] | 20 (1340 aa) |
| GTF 0427, *Streptococcus sobrinus*. The first 156 amino acids of the protein are deleted compared to GENBANK Identification No. 940427; a start methionine is included. | 25 [a] | 26 (1435 aa) |
| GTF 2919, *Streptococcus salivarius* PS4. The first 92 amino acids of the protein are deleted compared to GENBANK Identification No. 383282919; a start methionine is included. | 27 [a] | 28 (1340 aa) |
| GTF 2678, *Streptococcus salivarius* K12. The first 188 amino acids of the protein are deleted compared to GENBANK Identification No. 400182678; a start methionine is included. | 29 [a] | 30 (1341 aa) |
| GTF 3929, *Streptococcus salivarius* JIM8777. The first 178 amino acids of the protein are deleted compared to GENBANK Identification No. 387783929; a start methionine is included. | 33 [a] | 34 (1341 aa) |
| GTF 3298, *Streptococcus* sp. C150. The first 209 amino acids of the protein are deleted compared to GENBANK Identification No. 322373298; a start methionine is included. | | 59 (1242 aa) |
| Wild type GTFJ, *Streptococcus salivarius*. GENBANK Identification No. 47527. | | 60 (1518 aa) |
| Wild type GTF corresponding to GTF 2678, *Streptococcus salivarius* K12. | | 61 (1528 aa) |
| Wild type GTF corresponding to GTF 6855, *Streptococcus salivarius* SK126. | | 62 (1518 aa) |
| Wild type GTF corresponding to GTF 2919, *Streptococcus salivarius* PS4. | | 63 (1431 aa) |
| Wild type GTF corresponding to GTF 2765, unknown *Streptococcus* sp. C150. | | 64 (1532 aa) |
| Shorter version of GTF 7527, *Streptococcus salivarius*, (also referred to as "7527-NT" herein. The first 178 amino acids of the protein are deleted compared to GENBANK Identification No. 47527; a start methionine is included. | | 65 (1341 aa) |
| Terminator sequence added to pHY300PLK to derive the pHYT vector. | 67 | |
| Aclglu1 alpha-glucosidase. | | 68 (971 aa) |
| Nfiglu1 alpha-glucosidase. | | 69 (969 aa) |
| Ncrglu1 alpha-glucosidase. | | 70 (1022 aa) |
| TauSec098_b alpha-glucosidase. | | 71 (1012 aa) |
| TauSec098_c alpha-glucosidase. | | 72 (984 aa) |
| TauSec098_d alpha-glucosidase. | | 73 (984 aa) |
| TauSec099 alpha-glucosidase. | | 74 (973 aa) |
| BloGlu1 alpha-glucosidase. | | 75 (604 aa) |

TABLE 1-continued

Summary of Nucleic Acid and Protein SEQ ID Numbers[b]

| Description | Nucleic acid SEQ ID NO. | Protein SEQ ID NO. |
|---|---|---|
| BloGlu2 alpha-glucosidase. | | 76 (604 aa) |
| BloGlu3 alpha-glucosidase. | | 77 (604 aa) |
| BpsGlu1 alpha-glucosidase. | | 78 (585 aa) |
| BthGlu1 alpha-glucosidase. | | 79 (601 aa) |
| BbrGlu2 alpha-glucosidase. | | 80 (662 aa) |
| BbrGlu5 alpha-glucosidase. | | 81 (606 aa) |

[a] This DNA coding sequence is codon-optimized for expression in *E. coli* and is merely disclosed as an example of a suitable coding sequence.
[b] SEQ ID NOs: 21-24, 31, 32, 35-58 and 66 are intentionally not included in this table and merely serve as placeholders.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The terms "alpha-glucan", "alpha-glucan polymer" and the like are used interchangeably herein. An alpha-glucan is a polymer comprising glucose monomeric units linked together by alpha-glycosidic linkages. In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of alpha-glucan polymers herein include alpha-1,3-glucan.

The terms "poly alpha-1,3-glucan", "alpha-1,3-glucan", "alpha-1,3-glucan polymer" and the like are used interchangeably herein. Alpha-1,3-glucan is a polymer comprising glucose monomeric units linked together by glycosidic linkages, typically wherein at least about 50% of the glycosidic linkages are alpha-1,3. Alpha-1,3-glucan in certain embodiments comprises at least 90% or 95% alpha-1,3 glycosidic linkages. Most or all of the other linkages in alpha-1,3-glucan herein typically are alpha-1,6, though some linkages may also be alpha-1,2 and/or alpha-1,4.

The terms "glycosidic linkage", "glycosidic bond", "linkage" and the like are used interchangeably herein and refer to the covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. The term "alpha-1,6-glycosidic linkage" as used herein refers to the covalent bond that joins alpha-D-glucose molecules to each other through carbons 1 and 6 on adjacent alpha-D-glucose rings. The glycosidic linkages of a glucan polymer herein can also be referred to as "glucosidic linkages". Herein, "alpha-D-glucose" will be referred to as "glucose".

The glycosidic linkage profile of an alpha-glucan herein can be determined using any method known in the art. For example, a linkage profile can be determined using methods using nuclear magnetic resonance (NMR) spectroscopy (e.g., $^{13}$C NMR or $^1$H NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, FL, 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as $DP_w$ (weight average degree of polymerization) or $DP_n$ (number average degree of polymerization). The molecular weight of smaller alpha-glucan polymers such as oligosaccharides typically can be provided as "DP" (degree of polymerization), which simply refers to the number of glucoses comprised within the alpha-glucan. Various means are known in the art for calculating these various molecular weight measurements such as with high-pressure liquid chromatography (HPLC), size exclusion chromatography (SEC), or gel permeation chromatography (GPC).

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The terms "leucrose" and "D-glucopyranosyl-alpha(1-5)-D-fructopyranose" are used interchangeably herein and refer to a disaccharide containing an alpha-1,5 glucosyl-fructose linkage.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (by-products) of a GTF reaction can include glucose, various soluble gluco-oligosaccharides, and leucrose. Wild type forms of glucosyltransferase enzymes generally contain (in the N-terminal to C-terminal direction) a signal peptide (which is typically removed by cleavage processes), a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009).

The term "glucosyltransferase catalytic domain" herein refers to the domain of a glucosyltransferase enzyme that provides alpha-glucan-synthesizing activity to a glucosyltransferase enzyme. A glucosyltransferase catalytic domain typically does not require the presence of any other domains to have this activity.

The terms "enzymatic reaction", "glucosyltransferase reaction", "glucan synthesis reaction", "reaction composition", "reaction formulation" and the like are used interchangeably herein and generally refer to a reaction that initially comprises water, sucrose, at least one active glucosyltransferase enzyme, and optionally other components. Components that can be further present in a glucosyltransferase reaction typically after it has commenced include fructose, glucose, leucrose, soluble gluco-oligosaccharides (e.g., DP2-DP7) (such may be considered as products or by-products, depending on the glucosyltransferase used), and/or insoluble alpha-glucan product(s) of DP8 or higher (e.g., DP100 and higher). It would be understood that certain glucan products, such as alpha-1,3-glucan with a degree of polymerization (DP) of at least 8 or 9, are water-insoluble and thus not dissolved in a glucan synthesis reaction, but rather may be present out of solution (e.g., by virtue of having precipitated from the reaction). It is in a glucan synthesis reaction where the step of contacting water, sucrose and a glucosyltransferase enzyme is performed. The term "under suitable reaction conditions" as used herein refers to reaction conditions that support conversion of sucrose to alpha-glucan product(s) via glucosyltransferase enzyme activity.

The "yield" of an alpha-glucan product in a glucosyltransferase reaction in some aspects herein represents the molar yield based on the converted sucrose. The molar yield of an alpha-glucan product can be calculated based on the moles of the alpha-glucan product divided by the moles of the sucrose converted. Moles of converted sucrose can be calculated as follows: (mass of initial sucrose−mass of final sucrose)/molecular weight of sucrose [342 g/mol]. This molar yield calculation can be considered as a measure of selectivity of the reaction toward the alpha-glucan. In some aspects, the "yield" of an alpha-glucan product in a glucosyltransferase reaction can be based on the glucosyl component of the reaction. Such a yield (yield based on glucosyl) can be measured using the following formula:

Alpha-Glucan Yield=((IS/2−(FS/2+LE/2+GL+SO))/ (IS/2−FS/2))×100%.

The fructose balance of a glucosyltransferase reaction can be measured to ensure that HPLC data, if applicable, are not out of range (90-110% is considered acceptable). Fructose balance can be measured using the following formula:

Fructose Balance=((180/342×(FS+LE)+FR)/(180/ 342×IS))×100%.

In the above two formulae, IS is [Initial Sucrose], FS is [Final Sucrose], LE is [Leucrose], GL is [Glucose], SO is [Soluble Oligomers] (gluco-oligosaccharides), and FR is [Fructose]; the concentrations of each foregoing substrate/product provided in double brackets are in units of grams/L and as measured by HPLC, for example.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "aqueous conditions", "aqueous reaction conditions", "aqueous setting", "aqueous system" and the like are used interchangeably herein. Aqueous conditions herein refer to a solution or mixture in which the solvent is at least about 60 wt % water, for example. A glucosyltransferase reaction herein is performed under aqueous conditions.

The terms "soluble", "aqueous-soluble", "water-soluble" and the like as used herein characterize a glucan that has the capability of dissolving in water and/or an aqueous solution herein. Examples of soluble glucans herein are certain oligosaccharides, such as alpha-1,3-glucan with a DP less than 8. In contrast, a glucan that is "insoluble", "aqueous-insoluble", "water-insoluble" (and like terms) does not dissolve (or does not appreciably dissolve) in water and/or an aqueous solution herein. Optionally, the conditions for determining solubility include a water/solution temperature range of about 1 to 85° C. (e.g., 20-25° C.) and/or a pH range of about 4-9 (e.g., 6-8).

The terms "polynucleotide", "polynucleotide sequence", "nucleic acid molecule" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene can refer to a gene that is introduced into the host organism by gene transfer. Foreign/heterologous genes can comprise native genes inserted into a non-native organism, native genes introduced into a new location within the native host, or chimeric genes. Polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

As used herein, the term "polypeptide" is defined as a chain of amino acid residues, usually having a defined sequence. As used herein the term polypeptide is interchangeable with the terms "peptides" and "proteins". Typical amino acids contained in polypeptides herein include (respective three- and one-letter codes shown parenthetically): alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), valine (Val, V).

The term "heterologous" means not naturally found in the location of interest. For example, a heterologous gene can be one that is not naturally found in a host organism, but that is introduced into the host organism by gene transfer. As another example, a nucleic acid molecule that is present in a chimeric gene can be characterized as being heterologous, as such a nucleic acid molecule is not naturally associated with the other segments of the chimeric gene (e.g., a promoter can be heterologous to a coding sequence).

A "non-native" amino acid sequence or polynucleotide sequence comprised in a cell or organism herein does not occur in a native (natural) counterpart of such cell or organism. Such an amino acid sequence or polynucleotide sequence can also be referred to as being heterologous to the cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". A promoter may alternatively be inducible. One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator", "terminator" and the like as used herein refer to DNA sequences located downstream of a coding sequence. This includes polyadenylation recognition sequences and other sequences encoding regulatory signals capable of affecting mRNA processing or gene expression.

As used herein, a first nucleic acid sequence is "hybridizable" to a second nucleic acid sequence when a single-stranded form of the first nucleic acid sequence can anneal to the second nucleic acid sequence under suitable annealing conditions (e.g., temperature, solution ionic strength). Hybridization and washing conditions are well known and exemplified in Sambrook J, Fritsch E F and Maniatis T, *Molecular Cloning: A Laboratory Manual,* 2nd ed., Cold Spring Harbor Laboratory: Cold Spring Harbor, NY (1989), which is incorporated herein by reference, particularly Chapter 11 and Table 11.1.

The term "DNA manipulation technique" refers to any technique in which the sequence of a DNA polynucleotide sequence is modified. Although the DNA polynucleotide sequence being modified can be used as a substrate itself for modification, it does not have to be physically in hand for certain techniques (e.g., a sequence stored in a computer can be used as the basis for the manipulation technique). A DNA manipulation technique can be used to delete and/or mutate one or more DNA sequences in a longer sequence. Examples of a DNA manipulation technique include recombinant DNA techniques (restriction and ligation, molecular cloning), polymerase chain reaction (PCR), and synthetic DNA methods (e.g., oligonucleotide synthesis and ligation). Regarding synthetic DNA techniques, a DNA manipulation technique can entail observing a DNA polynucleotide in silico, determining desired modifications (e.g., one or more deletions) of the DNA polynucleotide, and synthesizing a DNA polynucleotide that contains the desired modifications.

The term "in silico" herein means in or on an information storage and/or processing device such as a computer; done or produced using computer software or simulation, i.e., virtual reality.

The terms "upstream" and "downstream" as used herein with respect to polynucleotides refer to "5' of" and "3' of", respectively.

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be up-regulated or down-regulated in certain embodiments.

The term "operably linked" as used herein refers to the association of two or more nucleic acid sequences such that the function of one is affected by the other. For example, a promoter is operably linked with a coding sequence when it is capable of affecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, WI), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.,* 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, *CABIOS.* 5:151-153 (1989); Higgins, D. G. et al., *Comput. Appl. Biosci.* 8:189-191(1992); Thompson, J. D. et al, *Nucleic Acids Research,* 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergent Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The terms "aligns with", "corresponds with", and the like can be used interchangeably herein. Some embodiments herein relate to a glucosyltransferase comprising at least one amino acid substitution at a position corresponding with at least one particular amino acid residue of SEQ ID NO:62. An amino acid position of a glucosyltransferase or subsequence thereof (e.g., catalytic domain or catalytic domain plus glucan-binding domains) (can refer to such an amino acid position or sequence as a "query" position or sequence) can be characterized to correspond with a particular amino acid residue of SEQ ID NO:62 (can refer to such an amino acid position or sequence as a "subject" position or sequence) if (1) the query sequence can be aligned with the subject sequence (e.g., where an alignment indicates that the query sequence and the subject sequence [or a subsequence of the subject sequence] are at least about 30%, 40%, 50%, 60%, 70%, 80%, or 90% identical), and (2) if the query amino acid position directly aligns with (directly lines up against) the subject amino acid position in the alignment of (1). In general, one can align a query amino acid sequence with a subject sequence (SEQ ID NO:62 or a subsequence of SEQ ID NO:62) using any alignment algorithm, tool and/or software described disclosed herein (e.g., BLASTP, ClustalW, ClustalV, Clustal-Omega, EMBOSS) to determine percent identity. Just for further example, one can align a query sequence with a subject sequence herein using the Needleman-Wunsch algorithm (Needleman and Wunsch, *J. Mol. Biol.* 48:443-453, 1970) as implemented in the Needle program of the European Molecular Biology Open Software Suite (EMBOSS [e.g., version 5.0.0 or later], Rice et al., *Trends Genet.* 16:276-277, 2000). The parameters of such an EMBOSS alignment can comprise, for example: gap open penalty of 10, gap extension penalty of 0.5, EBLOSUM62 (EMBOSS version of BLOSUM62) substitution matrix.

The numbering of particular amino acid residues of SEQ ID NO:62 herein (e.g., Leu-373, Leu-428, Ala-472, Ala-510, Leu-513, Met-529, Gln-588, Phe-607, Asn-613, Gln-616, Ser-631, Gly-633, Phe-634, Ser-710, Thr-635, Arg-722, Arg-741, Thr-877, Asp-948, Phe-951, Gln-957, Val-1188, Met-1253) is with respect to the full-length amino acid sequence of SEQ ID NO:62. The first amino acid (i.e., position 1, Met-1) of SEQ ID NO:62 is at the start of the signal peptide. Unless otherwise disclosed, substitutions herein are with respect to the full-length amino acid sequence of SEQ ID NO:62.

A "non-native glucosyltransferase" herein ("mutant", "variant", "modified" and like terms can likewise be used to describe such a glucosyltransferase) has at least one amino acid substitution at a position corresponding with a particular amino acid residue of SEQ ID NO:62. Such at least one amino acid substitution typically is in place of the amino acid residue(s) that normally (natively) occurs at the same position in the native counterpart (parent) of the non-native glucosyltransferase (i.e., although SEQ ID NO:62 is used as a reference for position, an amino acid substitution herein is with respect to the native counterpart of a non-native glucosyltransferase) (considered another way, when aligning the sequence of a non-native glucosyltransferase with SEQ ID NO:62, determining whether a substitution exists at a particular position does not depend in-and-of-itself on the respective amino acid residue in SEQ ID NO:62, but rather depends on what amino acid exists at the subject position within the native counterpart of the non-native glucosyltransferase). The amino acid normally occurring at the relevant site in the native counterpart glucosyltransferase often (but not always) is the same as (or conserved with) the particular amino acid residue of SEQ ID NO:62 for which the alignment is made. A non-native glucosyltransferase optionally can have other amino acid changes (mutations, deletions, and/or insertions) relative to its native counterpart sequence.

It may be instructive to illustrate a substitution/alignment herein. SEQ ID NO:12 (GTF 0544) is a truncated form of a *Streptococcus sobrinus* glucosyltransferase. It is noted that Leu-193 of SEQ ID NO:12 corresponds with Leu-373 of SEQ ID NO:62 (alignment not shown). If SEQ ID NO:12 is mutated at position 193 to substitute the Leu residue with a different residue (e.g., Gln), then it can be stated that the position 193-mutated version of SEQ ID NO:12 represents a non-native glucosyltransferase having an amino acid substitution at a position corresponding with Leu-373 of SEQ ID NO:62, for example.

The term "isolated" means a substance (or process) in a form or environment that does not occur in nature. Non-limiting examples of isolated substances include (1) any non-naturally occurring substance (e.g., a non-native glucosyltransferase herein), (2) any substance including, but not limited to, any host cell, enzyme, variant, nucleic acid, protein, peptide, cofactor, or carbohydrate/saccharide that is at least partially removed from one or more or all of the naturally occurring constituents with which it is associated in nature; (3) any substance modified by the hand of man relative to that substance found in nature (e.g., a non-native glucosyltransferase herein); or (4) any substance modified by increasing the amount of the substance relative to other components with which it is naturally associated. It is believed that the embodiments (e.g., enzymes and reaction compositions) disclosed herein are synthetic/man-made, and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

While advances have been made in producing glucan polymers using glucosyltransferase enzymes, less attention appears to have been drawn to improving the glucan yields of such enzymes. Addressing this technological gap, disclosed herein are glucosyltransferases engineered to have modified amino acid sequences endowing these enzymes with enhanced glucan production properties.

Certain embodiments of the present disclosure concern a non-native glucosyltransferase comprising at least two or three amino acid substitutions at positions corresponding with amino acid residues Gln-588, Phe-607, and/or Arg-741 of SEQ ID NO:62, wherein the non-native glucosyltransferase synthesizes alpha-glucan comprising 1,3-linkages, and wherein the non-native glucosyltransferase has:
 (i) an alpha-glucan yield that is higher than the alpha-glucan yield of a second glucosyltransferase that only differs from the non-native glucosyltransferase at the substitution position(s), and/or
 (ii) a leucrose yield that is lower than the leucrose yield of the second glucosyltransferase.

Thus, in general, mutant glucosyltransferase enzymes are disclosed herein that can synthesize higher amounts of alpha-glucan, and/or lower yields of leucrose, which is a by-product often considered undesirable when the main goal is alpha-glucan synthesis.

A non-native glucosyltransferase herein synthesizes alpha-glucan comprising 1,3-linkages. In some aspects, at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% of the glycosidic linkages of such an alpha-glucan can be alpha-1,3 linkages. The linkage profile of an alpha-glucan can optionally be characterized as having a range between any two of these values. The other linkages in any of these aspects having 30%-99% alpha-1,3 linkages can be alpha-1,6, and/or not include any alpha-1,4 or alpha-1,2 linkages, for example.

Alpha-glucan in some aspects can have, for example, less than 10%, 9%, 8%, 7%, 6%, 5%, 4%, 3%, 2%, 1%, or 0.5% of alpha-1,2 or alpha-1,4 glycosidic linkages. In another embodiment, an alpha-glucan only has alpha-1,3 and optionally alpha-1,6 linkages (i.e., no alpha-1,2 or alpha-1,4 linkages).

Alpha-glucan in some aspects can be linear/unbranched (no branch points). Alternatively, there can be branches in an alpha-glucan herein. For example, an alpha-glucan can have less than about 10%, 9%, 8%, 7%, 6%, 5%, 4%, 3%, 2%, or 1% branch points as a percent of the linkages in the polymer.

In certain aspects, an alpha-glucan can have a molecular weight in $DP_w$ or $DP_n$ of at least about 100. For example, the $DP_w$ or $DP_n$ can be about, or at least about, 100, 150, 200, 250, 300, 350, 400, 450, 500, 550, 600, 650, 700, 750, 800, 850, 900, 950, 1000, 1100, or 1200. The molecular weight of an alpha-glucan can optionally be expressed as a range between any two of these values (e.g., 100-1200, 400-1200, 700-1200, 100-1000, 400-1000, 700-1000).

An alpha-glucan produced by a non-native glucosyltransferase herein typically is water-insoluble. Alpha-1,3-glucan is generally insoluble at a $DP_w$ of 8 or 9 and above in neutral (e.g., pH 6-8) aqueous conditions.

Any of the foregoing linkage profiles and/or molecular weight profiles, for example, can be combined herein to appropriately characterize an alpha-glucan product of a non-native glucosyltransferase of the present disclosure. In some aspects, the linkage and/or molecular weight profile of an alpha-glucan product can be as disclosed in any of the following publications, all of which are incorporated herein by reference: U.S. Pat. Nos. 7,000,000 and 8,871,474, U.S. Patent Appl. Publ. No. 2015/0232819.

A non-native glucosyltransferase, for example, can comprise the amino acid sequence of any glucosyltransferase disclosed in the following publications that is capable of producing alpha-glucan as presently disclosed, but with the exception that the non-native glucosyltransferase comprises at least two of, or all three of, amino acid substitutions at positions corresponding with amino acid residues Gln-588, Phe-607, and/or Arg-741 of SEQ ID NO:62: U.S. Pat. Nos. 7,000,000 and 8,871,474; and U.S. Patent Appl. Publ. Nos. 2015/0232819 and 2017/0002335, all of which are incorporated herein by reference. In some aspects, such a non-native glucosyltransferase (i) comprises the foregoing substitutions, and (ii) comprises an amino acid sequence that is at least about 90%, 91%, 92%, 93%, 94%, 95%, 96%, 97%, 98%, 99%, or 99.5% identical to the amino acid sequence of the respective counterpart/parent glucosyltransferase not having the foregoing substitutions.

In some aspects, a non-native glucosyltransferase (i) comprises at least two of, or all three of, amino acid substitutions at positions corresponding with amino acid residues Gln-588, Phe-607, and/or Arg-741 of SEQ ID NO:62, and (ii) comprises or consists of an amino acid sequence that is at least about 90%, 91%, 92%, 93%, 94%, 95%, 96%, 97%, 98%, 99%, or 99.5% identical to SEQ ID NO:2, 4, 6, 8, 10, 12, 14, 16, 18, 20, 26, 28, 30, 34, or 59. Certain information regarding alpha-glucan products of glucosyltransferases with most of these amino acid sequences is provided in Table 2.

TABLE 2

GTF Enzymes and Related Alpha-Glucan Products[a]

| GTF ID | SEQ ID NO. | Reducing Sugars | Insoluble Product | Linkages % alpha-1,3 | Linkages % alpha-1,6 | $DP_n$ |
|---|---|---|---|---|---|---|
| 0874 | 2 | yes | yes | 100 | 0 | 60 |
| 6855 | 4 | yes | yes | 100 | 0 | 440 |
| 2379 | 6 | yes | yes | 37 | 63 | 310 |
| 7527 | 8 | yes | yes | 100 | 0 | 440 |
| 1724 | 10 | yes | yes | 100 | 0 | 250 |
| 0544 | 12 | yes | yes | 62 | 36 | 980 |
| 5926 | 14 | yes | yes | 100 | 0 | 260 |
| 4297 | 16 | yes | yes | 31 | 67 | 800 |
| 5618 | 18 | yes | yes | 34 | 66 | 1020 |
| 2765 | 20 | yes | yes | 100 | 0 | 280 |
| 0427 | 26 | yes | yes | 100 | 0 | 120 |
| 2919 | 28 | yes | yes | 100 | 0 | 250 |
| 2678 | 30 | yes | yes | 100 | 0 | 390 |
| 3929 | 34 | yes | yes | 100 | 0 | 280 |

[a]GTF reactions and product analyses were performed as follows. Reactions were prepared comprising sucrose (50 g/L), potassium phosphate buffer (pH 6.5, 20 mM) and a GTF enzyme (2.5% bacterial cell extract by volume; extracts prepared according to U.S. Appl. Publ. No. 2017/0002335, in a manner similar to procedure disclosed in U.S. Pat. No. 8,871,474). After 24-30 hours at 22-25° C., insoluble product was harvested by centrifugation, washed three times with water, washed once with ethanol, and dried at 50° C. for 24-30 hours. Approximate linkages and $DP_n$ are shown for each insoluble product. Linkages and $DP_n$ were determined by 13C NMR and SEC, respectively.

In some aspects, a non-native glucosyltransferase (i) comprises at least two of, or all three of, amino acid substitutions at positions corresponding with amino acid residues Gln-588, Phe-607 and/or Arg-741 of SEQ ID NO:62, and (ii) comprises or consists of a glucosyltransferase catalytic domain that is at least about 90%, 91%, 92%, 93%, 94%, 95%, 96%, 97%, 98%, 99%, or 99.5% identical to amino acid residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20. Such a non-native glucosyltransferase, for instance, is believed to be able to produce alpha-glucan that is water-insoluble and comprise at least about 50% (e.g., ≥90% or ≥95%) alpha-1,3 linkages, and optionally further have a $DP_w$ of at least 100. It is noted that a glucosyltransferase with amino acid positions 54-957 of SEQ ID NO:65 can produce alpha-1,3-glucan with 100% alpha-1,3 linkages and a $DP_w$ of at least 400 (data not shown, refer to Table 6 of U.S. Pat. Appl. Publ. No. 2017/0002335, which is incorporated herein by reference), for example. It is further noted that SEQ ID NOs:65 (GTF 7527), 30 (GTF 2678), 4 (GTF 6855), 28 (GTF 2919), and 20 (GTF 2765) each represent a glucosyltransferase that, compared to its respective wild type counterpart, lacks the signal peptide domain and all or a substantial portion of the variable domain. Thus, each of these glucosyltransferase enzymes has a catalytic domain followed by a glucan-binding domain. The approximate location of catalytic domain sequences in these enzymes is as follows: 7527 (residues 54-957 of SEQ ID NO:65), 2678 (residues 55-960 of SEQ ID NO:30), 6855 (residues 55-960 of SEQ ID NO:4), 2919 (residues 55-960 of SEQ ID NO:28), 2765 (residues 55-960 of SEQ ID NO:20). The amino acid sequences of the catalytic domains (approx.) of GTFs 2678, 6855, 2919 and 2765 have about 94.9%, 99.0%, 95.5% and 96.4% identity, respectively, with the approximate catalytic domain sequence of GTF 7527 (i.e., amino acids 54-957 of SEQ ID NO:65). Each of these particular glucosyltransferases (GTFs 2678, 6855, 2919 and 2765) can produce alpha-1,3-glucan with 100% alpha-1,3 linkages and a $DP_w$ of at least 400 (data not shown, refer to Table 4 of U.S. Pat. Appl. Publ. No. 2017/0002335). Based on this activity, and the relatedness (high percent identity) of the foregoing catalytic domains, it is contemplated that a non-native glucosyltransferase herein having one of the foregoing catalytic domains further with an amino acid substitution combination as presently disclosed can produce alpha-glucan comprising at least about 50% (e.g., ≥90% or ≥95%) alpha-1,3 linkages and a $DP_w$ of at least 100.

In some aspects, a non-native glucosyltransferase (i) comprises at least two of, or all three of, amino acid substitutions at positions corresponding with amino acid residues Gln-588, Phe-607 and/or Arg-741 of SEQ ID NO:62, and (ii) comprises or consists of an amino acid sequence that is at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:62 or a subsequence thereof such as SEQ ID NO:4 (without start methionine thereof) or positions 55-960 of SEQ ID NO:4 (approximate catalytic domain).

Although it is believed that a non-native glucosyltransferase in certain aspects need only have a catalytic domain, the non-native glucosyltransferase can be comprised within a larger amino acid sequence. For example, a catalytic domain may be linked at its C-terminus to a glucan-binding domain, and/or linked at its N-terminus to a variable domain and/or signal peptide.

Although amino acid substitutions in a non-native glucosyltransferase are generally disclosed herein with respect to the corresponding positions in SEQ ID NO:62, such substitutions can alternatively be stated simply with respect to its position number in the sequence of the non-native glucosyltransferase itself, as convenience may dictate.

Still further examples of non-native glucosyltransferases can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example. A non-native glucosyltransferase herein typically lacks an N-terminal signal peptide; such an enzyme can optionally be characterized as being mature if its signal peptide was removed during a secretion process.

A non-native glucosyltransferase herein can be derived from any microbial source, for example, such as bacteria. Examples of bacterial glucosyltransferases are those derived from a *Streptococcus* species, *Leuconostoc* species, or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A non-native glucosyltransferase herein can be prepared by fermentation of an appropriately engineered microbial strain, for example. Recombinant enzyme production by fermentation is well known in the art using microbial species such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*) and *Trichoderma* (e.g., *T. reesei*) (e.g., see Adrio and Demain, *Biomolecules* 4:117-139, 2014, which is incorporated herein by reference). A nucleotide sequence encoding a non-native glucosyltransferase amino acid sequence is typically linked to a heterologous promoter sequence to create an expression cassette for the enzyme, and/or is codon-optimized accordingly. Such an expression cassette may be incorporated in a suitable plasmid or integrated into the microbial host chromosome, using methods well known in the art. The expression cassette may include a transcriptional terminator nucleotide sequence following the amino acid coding sequence. The expression cassette may also include, between the promoter sequence and glucosyltransferase amino acid coding sequence, a nucleotide sequence encoding a signal peptide (e.g., heterologous signal peptide) that is designed for direct secretion of the glucosyltransferase enzyme. At the end of fermentation, cells may be ruptured accordingly (generally when a signal peptide for secretion is not employed) and the glucosyltransferase enzyme can be isolated using methods such as precipitation, filtration, and/or concentration. Alternatively, a lysate or extract comprising a glucosyltransferase can be used without further isolation. If the glucosyltransferase was secreted (i.e., it is present in the fermentation broth), it can optionally be used as isolated from, or as comprised in, the fermentation broth. The activity of a glucosyltransferase enzyme can be confirmed by biochemical assay, such as measuring its conversion of sucrose to glucan polymer.

A non-native glucosyltransferase herein can comprise amino acid substitutions at positions corresponding with at least two of, or all three of, amino acid residues Gln-588, Phe-607 and/or Arg-741 of SEQ ID NO:62. In some aspects, the amino acid substitution at a position corresponding with amino acid Gln-588 of SEQ ID NO:62 can be with a Leu, Ala, or Val residue. In some aspects, the amino acid substitution at a position corresponding with amino acid Phe-607 of SEQ ID NO:62 can be with a Trp, Tyr, or Asn residue. In some aspects, the amino acid substitution at a position corresponding with amino acid Arg-741 of SEQ ID NO:62 can be with a Ser or Thr residue. Examples of a non-native glucosyltransferase herein comprise at least: (A) Gln-588-Ala, Phe-607-Tyr and Arg-741-Ser substitutions; (B) Gln-588-Leu, Phe-607-Trp and Arg-741-Ser substitutions; or (C) Gln-588-Leu, Phe-607-Tyr and Arg-741-Thr substitutions. In some aspects, a non-native glucosyltransferase herein can comprise amino acid substitutions at positions corresponding with amino acid residues (i) Gln-588 and Phe-607, (ii) Gln-588 and Arg-741, or (iii) Phe-607 and Arg-741 of SEQ ID NO:62.

A non-native glucosyltransferase herein can comprise, in addition to the foregoing two or three amino acid substitutions, one, two, three, four, five, six, seven, eight, nine, or more of the disclosed amino acid substitutions, for instance. For example, a non-native glucosyltransferase can further comprise at least one amino acid substitution at a position corresponding with amino acid residue Ala-510 and/or Asp-948 of SEQ ID NO:62. In some aspects, the amino acid substitution at a position corresponding with amino acid Ala-510 of SEQ ID NO:62 can be with an Asp, Glu, Ile, or Val residue. In some aspects, the amino acid substitution at a position corresponding with amino acid Asp-948 of SEQ ID NO:62 can be with a Gly, Val, or Ala residue. Examples of a non-native glucosyltransferase herein comprise at least: (D) Ala-510-Glu and Asp-948-Val substitutions; (E) an Asp-948-Ala substitution; or (F) Ala-510-Asp and Asp-948-Gly substitutions, (in addition to any of the foregoing substitution combinations of A, B, or C, for example).

In another example, a non-native glucosyltransferase can further comprise at least one amino acid substitution at a position corresponding with amino acid residue Ser-631, Ser-710, Arg-722, and/or Thr-877 of SEQ ID NO:62. In some aspects, the amino acid substitution at a position corresponding with amino acid Ser-631 of SEQ ID NO:62 can be with a Thr, Asp, Glu, or Arg residue. In some aspects, the amino acid substitution at a position corresponding with amino acid Ser-710 of SEQ ID NO:62 can be with a Gly, Ala, or Val residue. In some aspects, the amino acid substitution at a position corresponding with amino acid Arg-722 of SEQ ID NO:62 can be with a His or Lys residue. In some aspects, the amino acid substitution at a position corresponding with amino acid Thr-877 of SEQ ID NO:62 can be with a Lys, His, or Arg residue. Examples of a non-native glucosyltransferase herein comprise at least: (G) Ser-631-Thr, Ser-710-Gly, Arg-722-His and Thr-877-Lys substitutions; (H) Ser-710-Ala, Arg-722-Lys and Thr-877-Lys substitutions; or (I) Ser-631-Ser, Ser-710-Gly, and Thr-877-Arg substitutions, (in addition to any of the foregoing substitution combinations of [i] A, B, or C; or [ii] A, B, or C with D, E, or F).

In another example, a non-native glucosyltransferase can further comprise at least one amino acid substitution at a position corresponding with amino acid residue Val-1188, Met-1253, and/or Gln-957 of SEQ ID NO:62. In some aspects, the amino acid substitution at a position corresponding with amino acid Val-1188 of SEQ ID NO:62 can be with a Glu or Asp residue. In some aspects, the amino acid substitution at a position corresponding with amino acid Met-1253 of SEQ ID NO:62 can be with an Ile, Leu, Ala, or Val residue. In some aspects, the amino acid substitution at a position corresponding with amino acid Gln-957 of SEQ ID NO:62 can be with a Pro residue. Examples of a non-native glucosyltransferase herein comprise at least: (J) a Val-1188-Asp substitution; (K) a Met-1253-Ile substitution; (L) Val-1188-Glu and Met-1253-Ile substitutions; (M) Val-1188-Glu, Met-1253-Ile and Gln-957-Pro substitutions; or (N) a Val-1188-Glu substitution (in addition to any of the foregoing substitution combinations of [i] A, B, or C; [ii] A, B, or C with D, E, or F; [iii] A, B, or C with G, H, or I; [iv] A, B, or C with one of D, E, or F, and one of G, H, or I).

Other suitable substitutions that can be in addition to those listed above, for example, include those as listed in Table 3 in Example 1 (below) that are associated with (i) a decrease in leucrose production by at least about 5%, 10%, 15%, 20%, 25%, 30%, 35%, 40%, 45%, 50%, 55%, 60%, 65%, 70%, 75%, 80%, 85%, 90%, or 95%, and/or (ii) an increase in glucan yield by at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, or 150%. In some aspects, suitable additional substitutions include those as listed in Table 3 in Example 1 (below) that are associated with a decrease in glucose production by at least about 5%, 10%, 15%, 20%, 25%, 30%, 35%, 40%, 45%, 50%, 55%, 60%, 65%, 70%, 75%, or 80%. In some aspects, suitable additional substitutions include those as listed in Table 3 in Example 1 (below) that are associated with a decrease in gluco-oligosaccharide (oligomer) production by at least about 5%, 10%, 15%, 20%, 25%, 30%, 35%, 40%, 45%, 50%, 55%, 60%, or 65%. The foregoing substitutions as listed in Table 3 are as they correspond with the listed residue position number in SEQ ID NO:62. In some aspects, one or more substitutions are conserved or non-conserved substitutions; such conservation (or not) can be, for instance, with respect to the amino acid that occurs in the native glucosyltransferase from which the non-native glucosyltransferase is derived.

Simply for illustration purposes, a non-native glucosyltransferase herein can comprise a combination of amino acid substitutions at positions as follows (i-xix), where each substitution position corresponds with the respective amino acid position number of SEQ ID NO:62:
(i) A510, Q588, F607, R741, D948, R722, T877, M1253 and K1277;
(ii) A510, Q588, F607, R741, D948, R722, T877, V1188, M1253 and Q957;
(iii) A510, Q588, F607, R741, D948, T877, V1188, M1253 and Q957;
(iv) A510, Q588, F607, R741, D948 and M1253;
(v) A510, Q588, F607, R741 and D948;
(vi) Q588, F607, R741 and D948;
(vii) A510, Q588, F607, R741, D948, N628, T635, T877, M1253, F929 and R1172;
(viii) A510, Q588, F607, R741, D948, S631, S710, R722, T877, V1188 and M1253;
(ix) A510, Q588, F607, R741, D948, S631, S710, R722, T877 and V1188;
(x) A510, Q588, F607, R741, D948, S631, S710, T877, V1188 and M1253;
(xi) A510, Q588, F607, R741 and D948;
(xii) A510, Q588, F607, R741, D948 and V1188;
(xiii) A510, Q588, F607, R741, D948, S631, S710 and V1188;
(xiv) A510, Q588, F607, R741, D948, S710, R722, T877 and M1253;
(xv) A510, Q588, F607, R741, D948, S631, R722, T877, V1188 and M1253;
(xvi) A510, Q588, F607, R741, D948, S631, T877, V1188 and M1253;
(xvii) A510, Q588, F607, R741, D948, S631 and V1188;
(xviii) A510, Q588, F607, R741, D948, S631, R722, T877, V1188 and M1253; or
(xix) A510, Q588, F607, R741, D948, V1188 and M1253;
Some particular examples of embodiments i-xix are disclosed in Example 4 below (Table 7). Thus, a non-native glucosyltransferase in some aspects can comprise one of the following combinations of substitutions (xx-xxxviii), where each substitution corresponds with the respective amino acid residue of SEQ ID NO:62:
(xx) A510D/Q588L/F607Y/R741S/D948G/R722H/T877K/M1253I/K1277N,
(xxi) A510D/Q588L/F607Y/R741S/D948G/R722H/T877K/V1188E/M1253I/Q957P,
(xxii) A510D/Q588L/F607Y/R741S/D948G/T877K/V1188E/M1253I/Q957P,
(xxiii) A510D/Q588L/F607Y/R741S/D948G/M1253I,
(xxiv) A510D/Q588L/F607W/R741S/D948G,
(xxv) Q588L/F607Y/R741S/D948G,
(xxvi) A510D/Q588L/F607Y/R741S/D948G/N628D/T635A/T877K/M1253I/F929L/R1172C,
(xxvii) A510D/Q588L/F607W/R741S/D948G/S631T/S710G/R722H/T877K/V1188E/M1253I,
(xxviii) A510D/Q588L/F607W/R741S/D948G/S631T/S710G/R722H/T877K/V1188E,
(xxix) A510D/Q588L/F607W/R741S/D948G/S631T/S710G/T877K/V1188E/M1253I,
(xxx) A510D/Q588L/F607Y/R741S/D948G,
(xxxi) A510D/Q588L/F607Y/R741S/D948G/V1188E,
(xxxii) A510D/Q588L/F607W/R741S/D948G/S631T/S710G/V1188E,
(xxxiii) A510D/Q588L/F607W/R741S/D948G/S710G/R722H/T877K/M1253I,
(xxxiv) A510D/Q588L/F607Y/R741S/D948G/S631T/R722H/T877K/V1188E/M1253I,
(xxxv) A510D/Q588L/F607W/R741S/D948G/S631T/T877K/V1188E/M1253I, (xxxvi) A510D/Q588L/F607W/R741S/D948G/S631T/ V1188E,
(xxxvii) A510D/Q588L/F607Y/R741S/D948G/S631T/ R722H/T877K/V1188E/M1253I, or
(xxxviii) A510D/Q588L/F607W/R741S/D948G/ V1188E/M1253I.

A non-native glucosyltransferase with a combination of amino acid substitutions herein can be based on any of a variety of glucosyltransferase amino acid sequences as presently disclosed, for example. Simply for illustration purposes, examples of such a non-native glucosyltransferase include those with a combination of amino acid substitutions as described herein (e.g., any of embodiments i-xxxviii above) and comprising or consisting of an amino acid sequence that is at least about 90%, 91%, 92%, 93%, 94%, 95%, 96%, 97%, 98%, 99%, or 99.5% identical to SEQ ID NO:65 (optionally without the start methionine of SEQ ID NO:65) or residues 54-957 of SEQ ID NO:65, SEQ ID NO:30 (optionally without the start methionine of SEQ ID NO:30) or residues 55-960 of SEQ ID NO:30, SEQ ID NO:4 (optionally without the start methionine of SEQ ID NO:4) or residues 55-960 of SEQ ID NO:4, SEQ ID NO:28 (optionally without the start methionine of SEQ ID NO:28) or residues 55-960 of SEQ ID NO:28, or SEQ ID NO:20 (optionally without the start methionine of SEQ ID NO:20) or residues 55-960 of SEQ ID NO:20.

A non-native glucosyltransferase herein can have (i) an alpha-glucan yield that is higher than the alpha-glucan yield of a second glucosyltransferase (or, simply, "another" glucosyltransferase) (e.g., parent glucosyltransferase) that only differs from the non-native glucosyltransferase at the substitution positions, and/or (ii) a leucrose yield that is lower than the leucrose yield of the second glucosyltransferase. A second glucosyltransferase herein, for example, can be comprised of all of, or mostly, native amino acid sequence. Thus, while a second glucosyltransferase herein can be a native glucosyltransferase in some aspects, it can be a prior-modified glucosyltransferase in other aspects (e.g., a glucosyltransferase with one or more other amino acid substitutions differing from the substitution[s] of the present disclosure). In some embodiments, a second glucosyltransferase to which a non-native glucosyltransferase is compared has native amino acid residues at the substitution positions. Determining whether an amino acid residue is native can be done by comparing the second glucosyltransferase amino acid sequence to the native/wild type glucosyltransferase amino acid sequence from which the second glucosyltransferase is derived. Optionally, a non-native glucosyltransferase in some embodiments can be characterized as having higher selectivity toward alpha-glucan synthesis (as compared to by-product synthesis).

In some aspects, a non-native glucosyltransferase herein can have an alpha-glucan yield that is at least about 5%, 10%, 20%, 40%, 60%, 80%, 100%, 120%, 140%, 160%, 180%, 200%, 220%, 240%, 260%, 280%, 300%, 320%, 340%, 360%, or 380% higher than the alpha-glucan yield of a second glucosyltransferase as presently disclosed. In some additional or alternative embodiments, a non-native glucosyltransferase can have a decrease in leucrose yield by at least about 5%, 10%, 15%, 20%, 25%, 30%, 35%, 40%, 45%, 50%, 55%, 60%, 65%, 70%, 75%, 80%, 85%, 90%, or 95% compared to the leucrose yield of a second glucosyltransferase. These determinations (alpha-glucan and/or leucrose yield) can be made with respect to any glucan synthesis reaction/process as disclosed herein (e.g., taking into account initial sucrose conc., temperature, pH, and/or reaction time), and using any suitable measurement technique (e.g., HPLC or NIR spectroscopy). Typically, a comparison between non-native and second glucosyltransferases herein can be made under identical or similar reaction conditions. The yield of a glucosyltransferase reaction in some aspects can be measured based on the glucosyl component of the reaction.

In some embodiments, a non-native glucosyltransferase can exhibit a decrease in the yield of soluble gluco-oligosaccharides by at least about 5%, 10%, 15%, 20%, 25%, 30%, 35%, 40%, 45%, 50%, 55%, 60%, 65%, 70%, or 75% compared to the soluble gluco-oligosaccharide yield of a second glucosyltransferase. A soluble gluco-oligosaccharide in some aspects can be DP2-7 or DP2-8, and have any linkage profile disclosed herein. In some aspects, the DP is ≥7, or up to 10, 15, 20, or 25, but with a linkage profile allowing solubility (e.g., not over 90% or 95% alpha-1,3).

In some embodiments, a non-native glucosyltransferase can exhibit a decrease in the yield of glucose by at least about 5%, 10%, 15%, 20%, 25%, 30%, 35%, 40%, 45%, 50%, 55%, 60%, 65%, 70%, 75%, or 80% compared to the glucose yield of a second glucosyltransferase.

Some embodiments disclosed herein concern a polynucleotide comprising a nucleotide sequence that encodes a non-native glucosyltransferase as presently disclosed. Optionally, one or more regulatory sequences are operably linked to the nucleotide sequence, and preferably a promoter sequence is included as a regulatory sequence.

A polynucleotide comprising a nucleotide sequence encoding a non-native glucosyltransferase herein can be a vector or construct useful for transferring a nucleotide sequence into a cell, for example. Examples of a suitable vector/construct can be selected from a plasmid, yeast artificial chromosome (YAC), cosmid, phagemid, bacterial artificial chromosome (BAC), virus, or linear DNA (e.g., linear PCR product). A polynucleotide sequence in some aspects can be capable of existing transiently (i.e., not integrated into the genome) or stably (i.e., integrated into the genome) in a cell. A polynucleotide sequence in some aspects can comprise, or lack, one or more suitable marker sequences (e.g., selection or phenotype marker).

A polynucleotide sequence in certain embodiments can comprise one or more regulatory sequences operably linked to the nucleotide sequence encoding a non-native glucosyltransferase. For example, a nucleotide sequence encoding a non-native glucosyltransferase may be in operable linkage with a promoter sequence (e.g., a heterologous promoter). A promoter sequence can be suitable for expression in a cell (e.g., bacterial cell such as *E. coli* or *Bacillus*; eukaryotic cell such as a fungus, yeast, insect, or mammalian cell) or in an in vitro protein expression system, for example.

Examples of other suitable regulatory sequences include transcription terminator sequences.

Some aspects herein are drawn to a cell comprising a polynucleotide sequence as presently disclosed; such a cell can be any type disclosed herein (e.g., bacterial cell such as *E. coli* or *Bacillus*; eukaryotic cell such as a fungus, yeast, insect, or mammalian cell). A cell can optionally express a non-native glucosyltransferase encoded by the polynucleotide sequence. In some aspects, the polynucleotide sequence exists transiently (i.e., not integrated into the genome) or stably (i.e., integrated into the genome) in the cell.

Some embodiments disclosed herein concern reaction compositions comprising water, sucrose, and one or more non-native glucosyltransferases herein. Such a reaction composition produces, at least, alpha-glucan comprising 1,3-linkages as disclosed.

The temperature of a reaction composition herein can be controlled, if desired, and can be about 5-50° C., 20-40° C., 30-40° C., 20-30° C., 20-25° C., 20° C., 25° C., 30° C., 35° C., or 40° C., for example.

The initial concentration of sucrose in a reaction composition herein can be about 20-400 g/L, 75-175 g/L, or 50-150 g/L, for example. In some aspects, the initial sucrose concentration is at least about 50, 75, 100, 150 or 200 g/L, or is about 50-600 g/L, 100-500 g/L, 50-100 g/L, 100-200 g/L, 150-450 g/L, 200-450 g/L, or 250-600 g/L. "Initial concentration of sucrose" refers to the sucrose concentration in a reaction composition just after all the reaction components have been added/combined (e.g., at least water, sucrose, non-native glucosyltransferase enzyme).

The pH of a reaction composition in certain embodiments can be about 4.0-9.0, 4.0-8.5, 4.0-8.0, 5.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. The buffer concentration in a reaction composition herein can be about 0.1-300 mM, 0.1-100 mM, 10-100 mM, 10 mM, 20 mM, or 50 mM, for example.

A reaction composition can be contained within any vessel (e.g., an inert vessel/container) suitable for applying one or more of the reaction conditions disclosed herein. An inert vessel in some aspects can be of stainless steel, plastic, or glass (or comprise two or more of these components) and be of a size suitable to contain a particular reaction. For example, the volume/capacity of an inert vessel (and/or the volume of a reaction composition herein), can be about, or at least about, 1, 10, 50, 100, 500, 1000, 2500, 5000, 10000, 12500, 15000, or 20000 liters. An inert vessel can optionally be equipped with a stirring device.

A reaction composition herein can contain one, two, or more glucosyltransferase enzymes, for example, just as long that at least one of the enzymes is a non-native glucosyltransferase as presently disclosed. In some embodiments, only one or two glucosyltransferase enzymes is/are comprised in a reaction composition. A glucosyltransferase reaction herein can be, and typically is, cell-free (e.g., no whole cells present).

Any of the features disclosed herein (e.g., above and in the below Examples) regarding a reaction composition can characterize appropriate aspects of a glucan production method herein, and vice versa.

The present disclosure also concerns a method for producing alpha-glucan, the method comprising: (a) contacting at least water, sucrose, and at least one non-native glucosyltransferase as disclosed herein that produces an alpha-glucan, whereby alpha-glucan is produced; and b) optionally, isolating the alpha-glucan produced in step (a). Conducting such a method, which can optionally be characterized as a glucan synthesis method, is typically also performed when conducting a reaction composition herein.

A glucan synthesis method as presently disclosed comprises contacting at least water, sucrose, and a non-native glucosyltransferase herein that produces an alpha-glucan. These and optionally other reagents can be added altogether or in any order as discussed below. This step can optionally be characterized as providing a reaction composition comprising water, sucrose and a non-native glucosyltransferase enzyme that synthesizes alpha-glucan. The contacting step herein can be performed in any number of ways. For example, the desired amount of sucrose can first be dissolved in water (optionally, other components may also be added at this stage of preparation, such as buffer components), followed by addition of glucosyltransferase enzyme. The solution may be kept still, or agitated via stirring or orbital shaking, for example. A glucan synthesis method can be performed by batch, fed-batch, continuous mode, or by any variation of these modes.

Completion of a reaction in certain embodiments can be determined visually (e.g., no more accumulation of insoluble glucan), and/or by measuring the amount of sucrose left in the solution (residual sucrose), where a percent sucrose consumption of at least about 90%, 95%, or 99% can indicate reaction completion. A reaction of the disclosed process can be conducted for about 1 hour to about 2, 4, 6, 8, 10, 12, 14, 16, 18, 20, 22, 24, 36, 48, 60, 72, 96, 120, 144, or 168 hours, for example.

The yield of an alpha-glucan produced in some aspects of a glucan synthesis method herein can be at least about 40%, 45%, 50%, 55%, 60%, 65%, 70%, 75%, 80%, 85%, 90%, 91%, 92%, 93%, 94%, 95%, or 96%. Yield in some aspects can be measured based on the glucosyl component of the reaction. In some additional or alternative embodiments, the yield of leucrose can be less than about 18%, 17%, 16%, 15%, 14%, 13%, 12%, 11%, 10%, 9%, 8%, 7%, 6%, 5%, 4%, 3%, 2%, or 1%. Such a yield in alpha-glucan and/or leucrose in some aspects is achieved in a reaction conducted for about 16-24 hours (e.g., ~20 hours), and/or is as measured using HPLC or NIR spectroscopy.

Insoluble alpha-glucan produced in a method herein can optionally be isolated. In certain embodiments, isolating insoluble alpha-glucan can include at least conducting a step of centrifugation and/or filtration. Isolation can optionally further comprise washing alpha-glucan one, two, or more times with water or other aqueous liquid, and/or drying the alpha-glucan product.

An isolated alpha-glucan product herein, as provided in a dry form, can comprise no more than 2.0, 1.5, 1.0, 0.5, 0.25, 0.10, 0.05, or 0.01 wt % water, for example. In some aspects, an alpha-glucan product is provided in an amount of at least 1 gram (e.g., at least about 2.5, 5, 10, 25, 50, 100, 250, 500, 750, 1000, 2500, 5000, 7500, 10000, 25000, 50000, or 100000 g); such an amount can be a dry amount, for example.

A glucan synthesis method in some aspects can further comprise contacting a soluble fraction of the glucosyltransferase reaction, and/or the glucosyltransferase reaction itself, with an alpha-glucosidase enzyme to hydrolyze at least one glycosidic linkage of one or more oligosaccharides present in the soluble fraction and/or glucosyltransferase reaction, thereby increasing the monosaccharide content in the soluble fraction. A soluble fraction herein can be contacted with an alpha-glucosidase after its separation from an insoluble fraction comprising alpha-1,3-glucan, or before its separation (e.g., while it is being formed in the reaction, and/or after completion of the reaction) (i.e., in contacting step [a] and/or after separation step [b]). A soluble fraction can be a filtrate or supernatant, for example, of a glucosyltransferase reaction, and is typically obtained following the completion of insoluble alpha-1,3-glucan synthesis. Examples of suitable alpha-glucosidases herein include those comprising an amino acid sequence that (i) is 100% identical to, or at least about 90%, 91%, 92%, 93%, 94%, 95%, 96%, 97%, 98%, or 99% identical to, any of SEQ ID NOs:68-81, and (ii) has hydrolytic activity toward alpha-1,5 glucosyl-fructose linkages, alpha-1,3 glucosyl-glucose linkages, and/or alpha-1,6 glucosyl-glucose linkages in saccharides.

Any of the disclosed conditions for synthesizing an alpha-glucan, such as the foregoing or those described in the below Examples, can be applied to practicing a reaction composition as presently disclosed (and vice versa), and/or used to characterize features/activity of a non-native glucosyltransferase, accordingly.

The present disclosure also concerns a method of preparing a polynucleotide sequence encoding a non-native glucosyltransferase herein. This method comprises:

(a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes alpha-glucan comprising 1,3-linkages; and (b) modifying the polynucleotide sequence identified in step (a) to substitute at least two or three amino acids of the parent glucosyltransferase at positions corresponding with amino acid residues Gln-588, Phe-607 and/or Arg-741 of SEQ ID NO:62, thereby providing a polynucleotide sequence encoding a non-native glucosyltransferase that has:

(i) an alpha-glucan yield that is higher than the alpha-glucan yield of the parent glucosyltransferase, and/or (ii) a leucrose yield that is lower than the leucrose yield of the parent glucosyltransferase.

Such a method can optionally further comprise using a polynucleotide prepared in this manner in a method of expressing the non-native glucosyltransferase encoded by the polynucleotide. Such an expression method can follow any heterologous protein expression method as known in the art, for example. The present method of preparing a polynucleotide can optionally alternatively be characterized as a method of increasing the product yield of a glucosyltransferase.

Identification step (a) herein can, in some instances, comprise identifying an amino acid sequence of a parent glucosyltransferase enzyme. A polynucleotide sequence could be determined from this amino acid sequence according to the genetic code (codons), such as the genetic code used in the species from which the parent glucosyltransferase was identified.

Identifying a polynucleotide encoding a parent glucosyltransferase herein can be performed (a) in silico, (b) with a method comprising a nucleic acid hybridization step, (c) with a method comprising a protein sequencing step, and/or (d) with a method comprising a protein binding step, for example.

Regarding in silico detection, the amino acid sequences of candidate parent glucosyltransferase enzymes (and/or nucleotide sequences encoding such glucosyltransferase enzymes) stored in a computer or database (e.g., public databases such as GENBANK, EMBL, REFSEQ, GENEPEPT, SWISS-PROT, PIR, PDB) can be reviewed in silico to identify a glucosyltransferase enzyme comprising an amino acid sequence with a percent sequence identity as described above for a parent glucosyltransferase. Such review could comprise using any means known in the art such as through use of an alignment algorithm or software as described above (e.g., BLASTN, BLASTP, ClustalW, ClustalV, Clustal-Omega, EMBOSS).

Identifying a parent glucosyltransferase as disclosed above can optionally be performed via a method comprising a nucleic acid hybridization step. Such a method can comprise using DNA hybridization (e.g., Southern blot, dot blot), RNA hybridization (e.g., northern blot), or any other method that has a nucleic acid hybridization step (e.g., DNA sequencing, PCR, RT-PCR, all of which may comprise hybridization of an oligonucleotide), for example. A polynucleotide sequence encoding SEQ ID NO:4 or a subsequence thereof (e.g., positions 55-960 of SEQ ID NO:4) can be used as a probe, for example, in such a hybridization. Conditions and parameters for carrying out hybridization methods in general are well known and disclosed, for example, in Sambrook J, Fritsch E F and Maniatis T, *Molecular Cloning: A Laboratory Manual*, Cold Spring Harbor Laboratory: Cold Spring Harbor, NY (1989); Silhavy T J, Bennan M L and Enquist L W, *Experiments with Gene Fusions*, Cold Spring Harbor Laboratory: Cold Spring Harbor, NY (1984); Ausubel F M et al., *Current Protocols in Molecular Biology*, published by Greene Publishing Assoc. and Wiley-Interscience, Hoboken, NJ (1987); and Innis M A, Gelfand D H, Sninsky J J and White T J (Editors), *PCR Protocols: A Guide to Methods and Applications*, Academic Press, Inc., San Diego, CA (1990).

Identifying a parent glucosyltransferase as disclosed above can optionally be performed via a method comprising a protein sequencing step. Such a protein sequencing step can comprise one or more procedures such as N-terminal amino acid analysis, C-terminal amino acid analysis, Edman degradation, or mass spectrometry, for example.

Identifying a parent glucosyltransferase as disclosed above can optionally be performed via a method comprising a protein binding step. Such a protein binding step can be performed using an antibody that binds to a motif or epitope within SEQ ID NO:4 (e.g., within positions 55-960 of SEQ ID NO:4), for example.

A polynucleotide identified in step (a) (i.e., before its modification in step [b]) can, in some aspects, encode a glucosyltransferase comprising an amino acid sequence that is identical to, or at least 90%, 91%, 92%, 93%, 94%, 95%, 96%, 97%, 98%, or 99% identical to, the amino acid sequence of any glucosyltransferase disclosed in Table 1. An alpha-glucan as produced by such a glucosyltransferase can be as disclosed herein, for example.

A method of preparing a polynucleotide sequence encoding a non-native glucosyltransferase herein comprises step (b) of modifying the polynucleotide sequence (encoding a parent glucosyltransferase) identified in step (a). Such modification substitutes at least two or three amino acids of the parent glucosyltransferase at positions corresponding with amino acid residues Gln-588, Phe-607 and/or Arg-741 of SEQ ID NO:62. The non-native glucosyltransferase (encoded by the modified polynucleotide sequence) resulting from such substitutions can be optionally characterized as a "child glucosyltransferase" herein.

A parent glucosyltransferase enzyme herein can comprise an amino acid sequence that is at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:4 (optionally without start methionine thereof) or positions 55-960 of SEQ ID NO:4 (approximate catalytic domain), for example. It is noted simply for reference purposes that SEQ ID NO:4 without its start methionine is a subsequence of SEQ ID NO:62.

A suitable modification of a polynucleotide in step (b) can be made following any DNA manipulation technique known in the art. Modifying step (b) can optionally be performed in silico, followed by synthesis of the polynucleotide sequence encoding a non-native glucosyltransferase. For example, a polynucleotide sequence identified in step (a) can be manipulated in silico using a suitable sequence manipulation program/software (e.g., VECTOR NTI, Life Technologies, Carlsbad, CA; DNAStrider; DNASTAR, Madison, WI). Following such virtual manipulation, the modified polynucleotide sequence can be artificially synthesized by any suitable technique (e.g., annealing-based connection of oligonucleotides, or any technique disclosed in Hughes et al., *Methods Enzymol.* 498:277-309, which is incorporated herein by reference). It should be appreciated that the foregoing methodology is not believed to necessarily rely on having a pre-existing polynucleotide (encoding a parent glucosyltransferase) in hand.

Modifying step (b) can optionally be performed using a physical copy of a polynucleotide sequence identified in step (a) encoding a parent glucosyltransferase. As an example, such a polynucleotide can serve as a template for amplification using primers designed in a manner such that the amplified product encodes a non-native glucosyltransferase herein (e.g., refer to Innis et al., ibid.).

The amino acid substitutions in this method can be any of those combinations of substitutions as disclosed herein. Essentially any non-native glucosyltransferase as presently disclosed can be encoded by a polynucleotide as prepared by this method, for instance, and consequently can have the higher alpha-glucan yield and/or lower leucrose yield profiles disclosed herein.

Non-limiting examples of compositions and methods disclosed herein include:

1. A non-native glucosyltransferase comprising at least two or three amino acid substitutions at positions corresponding with amino acid residues Gln-588, Phe-607, and/or Arg-741 of SEQ ID NO:62, wherein the non-native glucosyltransferase synthesizes alpha-glucan comprising 1,3-linkages, and wherein the non-native glucosyltransferase has: (i) an alpha-glucan yield that is higher than the alpha-glucan yield of a second glucosyltransferase that only differs from the non-native glucosyltransferase at the substitution positions, and/or (ii) a leucrose yield that is lower than the leucrose yield of the second glucosyltransferase.
2. The non-native glucosyltransferase of embodiment 1, wherein the glucosyltransferase comprises amino acid substitutions at positions corresponding with amino acid residues Gln-588, Phe-607 and Arg-741 of SEQ ID NO:62.
3. The non-native glucosyltransferase of embodiment 1 or 2, wherein: (i) the amino acid substitution at the position corresponding with amino acid residue Gln-588 is with a Leu, Ala, or Val residue; (ii) the amino acid substitution at the position corresponding with amino acid residue Phe-607 is with a Trp, Tyr, or Asn residue; and/or (iii) the amino acid substitution at the position corresponding with amino acid residue Arg-741 is with a Ser or Thr residue.
4. The non-native glucosyltransferase of embodiment 1, 2, or 3, wherein the glucosyltransferase further comprises at least one amino acid substitution at a position corresponding with amino acid residue Ala-510 and/or Asp-948 of SEQ ID NO:62; optionally wherein: (i) the amino acid substitution at the position corresponding with amino acid residue Ala-510 is with an Asp, Glu, Ile, or Val residue; and/or (ii) the amino acid substitution at the position corresponding with amino acid residue Asp-948 is with a Gly, Val, or Ala residue.
5. The non-native glucosyltransferase of embodiment 1, 2, 3, or 4, wherein the glucosyltransferase further comprises at least one amino acid substitution at a position corresponding with amino acid residue Ser-631, Ser-710, Arg-722, and/or Thr-877 of SEQ ID NO:62; optionally wherein: (i) the amino acid substitution at the position corresponding with amino acid residue Ser-631 is with a Thr, Asp, Glu, or Arg residue; (ii) the amino acid substitution at the position corresponding with amino acid residue Ser-710 is with a Gly, Ala, or Val residue; (iii) the amino acid substitution at the position corresponding with amino acid residue Arg-722 is with a His or Lys residue; and/or (iv) the amino acid substitution at the position corresponding with amino acid residue Thr-877 is with a Lys, His, or Arg residue.
6. The non-native glucosyltransferase of embodiment 1, 2, 3, 4, or 5, wherein the glucosyltransferase further comprises at least one amino acid substitution at a position corresponding with amino acid residue Val-1188, Met-1253, and/or Gln-957 of SEQ ID NO:62; optionally wherein: (i) the amino acid substitution at the position corresponding with amino acid residue Val-1188 is with a Glu or Asp residue; (ii) the amino acid substitution at the position corresponding with amino acid residue Met-1253 is with an Ile, Leu, Ala, or Val residue; and/or (iii) the amino acid substitution at the position corresponding with amino acid residue Gln-957 is with a Pro residue.
7. The non-native glucosyltransferase of embodiment 1, 2, 3, 4, 5, or 6, wherein the alpha-glucan produced by the non-native glucosyltransferase is insoluble and comprises at least about 50% alpha-1,3 linkages, and optionally wherein it has a weight average degree of polymerization ($DP_w$) of at least 100.
8. The non-native glucosyltransferase of embodiment 7, comprising a catalytic domain that is at least about 90% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.
9. The non-native glucosyltransferase of embodiment 7 or 8, comprising an amino acid sequence that is at least about 90% identical to SEQ ID NO:4, SEQ ID NO:65, SEQ ID NO:30, SEQ ID NO:28, or SEQ ID NO:20.
10. The non-native glucosyltransferase of embodiment 1, 2, 3, 4, 5, 6, 7, 8, or 9, wherein the non-native glucosyltransferase synthesizes insoluble alpha-1,3-glucan having at least about 90% (or at least 95%) alpha-1,3-linkages.
11. The non-native glucosyltransferase of embodiment 1, 2, 3, 4, 5, 6, 7, 8, 9, or 10, wherein the alpha-glucan yield is at least about 10% higher than the alpha-glucan yield of the second glucosyltransferase.
12. A polynucleotide comprising a nucleotide sequence encoding a non-native glucosyltransferase according to any one of embodiments 1-11, optionally wherein one or more regulatory sequences are operably linked to the nucleotide sequence, and preferably wherein the one or more regulatory sequences include a promoter sequence.
13. A reaction composition comprising water, sucrose, and a non-native glucosyltransferase according to any one of embodiments 1-11.
14. A method of producing alpha-glucan comprising: (a) contacting at least water, sucrose, and a non-native glucosyltransferase enzyme according to any one of embodiments 1-11, whereby alpha-glucan is produced; and (b) optionally, isolating the alpha-glucan produced in step (a).

15. A method of preparing a polynucleotide sequence encoding a non-native glucosyltransferase (e.g., of any one of embodiments 1-11), the method comprising: (a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes alpha-glucan comprising 1,3-linkages; and (b) modifying the polynucleotide sequence identified in step (a) to substitute at least two or three amino acids of the parent glucosyltransferase at positions corresponding with amino acid residues Gln-588, Phe-607, and/or Arg-741 of SEQ ID NO:62, thereby providing a polynucleotide sequence encoding a non-native glucosyltransferase that has: (i) an alpha-glucan yield that is higher than the alpha-glucan yield of the parent glucosyltransferase, and/or (ii) a leucrose yield that is lower than the leucrose yield of the parent glucosyltransferase.

16. The method of embodiment 15, wherein the identifying step is performed: (a) in silico, (b) with a method comprising a nucleic acid hybridization step, (c) with a method comprising a protein sequencing step, and/or (d) with a method comprising a protein binding step; and/or wherein the modifying step is performed: (e) in silico, followed by synthesis of the polynucleotide sequence encoding the non-native glucosyltransferase enzyme, or (f) using a physical copy of the polynucleotide sequence encoding the parent glucosyltransferase.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Analysis of Amino Acid Sites Affecting Glucosyltransferase Selectivity Toward Alpha-Glucan Synthesis This Example describes screening for glucosyltransferase variants with improved selectivity toward alpha-glucan synthesis from sucrose. Another aim of this screening was to identify glucosyltransferase variants that exhibit reduced synthesis of by-products such as leucrose and gluco-oligosaccharides. Variants having either or both of these yield properties were identified.

The amino acid sequence of the glucosyltransferase used to prepare amino acid substitutions in this Example was SEQ ID NO:4 (GTF 6855), which essentially is an N-terminally truncated (signal peptide and variable region removed) version of the full-length wild type glucosyltransferase (represented by SEQ ID NO:62) from *Streptococcus salivarius* SK126 (see Table 1). Substitutions made in SEQ ID NO:4 can be characterized as substituting for native amino acid residues, as each amino acid residue/position of SEQ ID NO:4 (apart from the Met-1 residue of SEQ ID NO:4) corresponds accordingly with an amino acid residue/position within SEQ ID NO:62. In reactions comprising at least sucrose and water, the glucosyltransferase of SEQ ID NO:4 typically produces alpha-glucan having about 100% alpha-1,3 linkages and a $DP_w$ of 400 or greater (e.g., refer to U.S. Pat. Nos. 8,871,474 and 9,169,506, and U.S. Pat. Appl. Publ. No. 2017/0002336, which are incorporated herein by reference). This alpha-glucan product, which is insoluble, can be isolated following enzymatic synthesis via filtration, for example.

To summarize this Example, GTF 6855 variants (each with a single amino acid substitution) from site evaluation libraries (SEL) were each bacterially expressed, purified, and normalized to a concentration of 100 ppm. Each enzyme preparation was then screened (in triplicate) using sucrose as substrate in alpha-1,3 glucan synthesis reactions. In addition to determining the amount of alpha-1,3 glucan polymer produced in each reaction, the soluble sugar products (fructose, glucose, leucrose, gluco-oligosaccharides) and residual sucrose of each reaction were analyzed by HPLC after about a 20-hour incubation.

Plasmids for individually expressing various single amino acid-substituted variants of GTF 6855 (SEQ ID NO:4) in a *Bacillus subtilis* host were prepared. Such plasmids were prepared as follows. A DNA expression cassette having (operably linked in 5'-to-3' order) the *B. subtilis* aprE promoter, a codon-optimized sequence encoding SEQ ID NO:4 (GTF 6855), and a BPN' terminator was synthesized. This expression cassette was cloned into the pHYT replicating shuttle vector (forming pHYT-GTF6855) and transformed into *B. subtilis* CBS12-1. The pHYT vector was derived from pHY300PLK (Takara) by adding a terminator sequence (SEQ ID NO:67) after the tetracycline resistance gene using the BstEII and EcoRI sites. The HindIII site in pHY300PLK had been removed by cloning a linker sequence (not shown) into the BamHI and HindIII sites. The pHYT-GTF6855 plasmid was amplified and used for generating SELs. The resulting plasmids encoding single-amino acid substituted GTFs were sequenced to verify each substitution.

To produce GTF 6855 (SEQ ID NO:4) and single amino acid-substituted variants thereof, *B. subtilis* individually transformed with pHYT-GTF6855 or mutated versions thereof were cultivated in Tryptone Soya Broth (Oxoid Ltd., UK) and Grant's II medium. Heart infusion agar plates (Difco Laboratories, MI) were used to select transformants. Plasmid integrity was maintained by the addition of 25 μg/mL tetracycline. Each GTF targeted for expression was detected in the growth medium after incubation for about 6 hours at 37° C. After centrifugation and filtration, culture supernatants with expressed GTF were obtained. GTF enzyme present in the supernatant was purified to apparent homogeneity by affinity chromatography using washed (2×MILLIQ 1×25 mM $NaH_2PO_4$ pH 5.7 with intermediate centrifugation steps 100×g) SUPERDEX 200 resin (GE Healthcare). Each GTF was eluted with a 15% solution of Dextran T1 (Pharmacosmos) in 25 mM $NaH_2PO_4$ pH 5.7 by centrifugation 100×g. Each purified GTF was dialyzed against 25 mM $NaH_2PO_4$ pH 5.7 buffer (at least 100×) using a Harvard Apparatus 96-well DISPODIALYZER (10000-Dalton MWCO).

After dialysis, GTF enzyme concentration was determined by OD280 using purified GTF 6855 as a standard. Normalization of each purified GTF to 100 ppm was achieved by diluting appropriately with 25 mM NaH$_2$PO$_4$ pH 5.7. Protein concentration for each sample was confirmed using an AGILENT 1200 (Agilent Technologies) HPLC equipped with an AGILENT BIO SEC3 guard-column column (3 μm 100 Å (4.6×50 mm). Five (5) μL of sample was injected onto the column for each determination. Compounds were eluted with isocratic flow of 25 mM KH$_2$PO$_4$ pH 6.8+0.1 M NaCl for 1.3 min at 0.5 mL/min flow rate.

Each GTF (GTF 6855 and each variant thereof) was entered into a reaction with sucrose to determine yield and selectivity. Each reaction was performed as follows: 37.5 μL of 100 ppm enzyme sample (ppm based on a BSA calibration curve) was added to 262.5 μL of 86 g/L sucrose (75 g/L final) in 20 mM Na$_2$HPO$_4$/NaH$_2$PO$_4$ pH 5.7 and incubated overnight (about 20 hours) at 30° C. After this incubation, each reaction was quenched by incubation for 1 hour at 80° C. A 200-μL aliquot of each quenched reaction was filtered in vacuo via a 0.45-μm filter plate (Millipore 0.45-μm Hydrophilic) and each filtrate was diluted 5×(10 μL sample+ 40 μL 20 mM Na$_2$HPO$_4$/NaH$_2$PO$_4$) in preparation for HPLC sugar analysis.

Sucrose, glucose, fructose, leucrose and relative oligosaccharide concentrations in each diluted filtrate were determined using an AGILENT 1200 (Agilent Technologies) HPLC equipped with a 150×7.80 mm PHENOMENEX REZEX RNM carbohydrate Na$^+$ 8% column PHENOMENX KRUDKATCHER 0.5-μm guard column. The column was operated at 80° C. with an isocratic flow-rate of 0.9 mL/min with 10 mM Na$_2$HPO$_4$/NaH$_2$PO$_4$ pH 6.7 (5 min per sample). Five μL of diluted sample was injected. Appropriate sucrose, glucose, fructose, and leucrose calibration curves were used to determine sugar concentrations. A mixture of purified gluco-oligosaccharides was used to determine oligomer concentration.

The profiles of reactions (~20 hours) as measured via the above methodology are provided in Table 3.

TABLE 3

Product Profiles of GTF 6855 (SEQ ID NO: 4) and Single Amino Acid-Substituted Variants thereof

| GTF | Sucrose (g/L)$^d$ | Leucrose (g/L)$^d$ | Glucose (g/L)$^d$ | Fructose (g/L)$^d$ | Oligomers (g/L)$^{d,e}$ | Alpha-1,3 Glucan$^f$ Yield$^i$ | Fructose Balance |
|---|---|---|---|---|---|---|---|
| Plate 1$^a$ | | | | | | | |
| 6855$^b$ | 1.6 | 21.1 | 6.3 | 28.9 | 9.1 | 31% | 97% |
| 6855$^b$ | 1.6 | 21.3 | 6.3 | 29.1 | 10.5 | 27% | 98% |
| 6855$^b$ | 1.6 | 21.2 | 6.3 | 29.3 | 10.0 | 29% | 98% |
| 6855$^b$ | 1.6 | 21.1 | 6.3 | 28.9 | 10.8 | 27% | 97% |
| V186A$^c$ | 1.6 | 21.3 | 6.4 | 28.8 | 10.7 | 27% | 97% |
| V186M | 1.6 | 21.4 | 6.4 | 28.7 | 10.6 | 27% | 97% |
| E194C | 1.6 | 21.2 | 6.3 | 29.0 | 9.4 | 30% | 98% |
| L434N | 1.9 | 22.7 | 7.1 | 28.4 | 12.7 | 18% | 99% |
| A472C | 31.0 | 2.6 | 2.5 | 23.8 | 4.6 | 38% | 99% |
| A472S | 5.3 | 2.8 | 13.9 | 36.5 | 9.1 | 31% | 97% |
| A510E | 8.5 | 5.4 | 5.5 | 34.5 | 5.6 | 53% | 100% |
| A510E | 1.9 | 6.5 | 5.6 | 36.7 | 6.1 | 58% | 98% |
| A510I | 4.3 | 6.8 | 5.4 | 35.2 | 5.4 | 57% | 98% |
| A510V | 1.7 | 9.5 | 6.4 | 35.6 | 6.8 | 51% | 99% |
| L513Y | 1.4 | 10.3 | 4.2 | 35.3 | 7.2 | 54% | 99% |
| M529L | 1.9 | 10.4 | 4.2 | 35.2 | 10.9 | 44% | 99% |
| K578M | 1.6 | 21.0 | 6.4 | 28.8 | 10.8 | 27% | 97% |
| Y605W | 6.1 | 8.0 | 2.6 | 33.3 | 5.4 | 59% | 97% |
| F607N | 8.4 | 11.4 | 4.1 | 30.5 | 7.1 | 45% | 98% |
| F607W | 9.1 | 4.6 | 3.8 | 33.9 | 8.6 | 49% | 98% |
| N613I | 4.5 | 7.7 | 6.4 | 35.8 | 14.8 | 29% | 101% |
| N613M | 2.7 | 11.0 | 5.3 | 34.6 | 12.1 | 37% | 100% |
| N613T | 1.7 | 10.3 | 4.6 | 35.0 | 7.1 | 53% | 98% |
| N613V | 2.8 | 0.0 | 6.3 | 37.3 | 12.1 | 48% | 92% |
| Q616E | 3.9 | 2.4 | 5.8 | 37.3 | 8.8 | 53% | 97% |
| K625A | 1.5 | 21.2 | 6.3 | 29.4 | 9.9 | 29% | 99% |
| K625M | 1.5 | 21.3 | 6.3 | 29.3 | 10.6 | 27% | 99% |
| S631T | 5.4 | 11.4 | 4.6 | 32.0 | 7.6 | 46% | 97% |
| T635H | 4.1 | 11.0 | 5.0 | 32.7 | 8.2 | 46% | 97% |
| T635W | 13.1 | 8.5 | 4.5 | 29.6 | 7.0 | 42% | 98% |
| I636H | 7.0 | 11.7 | 5.0 | 31.1 | 8.1 | 42% | 98% |
| D947G | 2.4 | 19.1 | 6.1 | 29.8 | 9.9 | 31% | 98% |
| F951Y | 4.0 | 1.5 | 9.9 | 38.0 | 15.4 | 28% | 97% |
| E849M | 1.4 | 20.7 | 6.2 | 29.5 | 10.4 | 29% | 98% |
| Q1007A | 1.4 | 19.4 | 6.2 | 30.2 | 10.1 | 31% | 98% |
| D1003G | 13.8 | 10.7 | 4.6 | 28.3 | 5.4 | 42% | 98% |
| A1022M | 1.7 | 20.6 | 6.2 | 29.3 | 12.2 | 24% | 98% |
| D1028L | 1.6 | 22.1 | 6.6 | 28.9 | 11.6 | 23% | 99% |
| D1028Q | 1.6 | 21.7 | 6.5 | 29.4 | 10.9 | 26% | 99% |
| A1057H | 1.5 | 21.4 | 6.4 | 29.2 | 10.6 | 27% | 98% |
| N1096A | 1.6 | 22.4 | 6.6 | 28.6 | 10.7 | 25% | 98% |
| E1132A | 1.5 | 21.4 | 6.4 | 29.2 | 10.6 | 27% | 98% |
| E1132H | 1.5 | 21.3 | 6.4 | 29.2 | 10.5 | 27% | 98% |
| E1132K | 1.5 | 21.4 | 6.4 | 29.2 | 10.4 | 27% | 98% |
| E1132R | 1.5 | 21.6 | 6.4 | 29.1 | 10.8 | 26% | 99% |
| L1212N | 1.5 | 20.9 | 6.3 | 29.5 | 10.4 | 28% | 98% |
| T1431M | 1.5 | 21.4 | 6.3 | 29.4 | 10.5 | 27% | 99% |

TABLE 3-continued

Product Profiles of GTF 6855 (SEQ ID NO: 4) and Single Amino Acid-Substituted Variants thereof

| GTF | Sucrose (g/L)[d] | Leucrose (g/L)[d] | Glucose (g/L)[d] | Fructose (g/L)[d] | Oligomers (g/L)[d,e] | Alpha-1,3 Glucan[f] Yield[i] | Fructose Balance |
|---|---|---|---|---|---|---|---|
| A1442R | 1.5 | 21.3 | 6.4 | 29.1 | 10.6 | 27% | 98% |
| Dead[g] | 79.4 | 0.0 | 0.0 | 0.0 | 0.0 | 0% | 100% |
| Blank[h] | 79.7 | 0.0 | 0.1 | 0.0 | 0.0 | 0% | 100% |
| Blank[h] | 80.1 | 0.0 | 0.0 | 0.0 | 0.0 | 0% | 100% |
| Plate 2[a] | | | | | | | |
| 6855[b] | 1.4 | 20.1 | 6.4 | 28.2 | 10.0 | 29% | 99% |
| 6855[b] | 1.4 | 20.1 | 6.4 | 28.2 | 10.1 | 28% | 99% |
| 6855[b] | 1.4 | 20.0 | 6.3 | 28.3 | 10.3 | 28% | 99% |
| 6855[b] | 1.5 | 20.2 | 6.3 | 28.2 | 10.0 | 29% | 100% |
| Y219C[c] | 1.5 | 20.6 | 6.5 | 27.7 | 10.7 | 25% | 99% |
| E243H | 1.4 | 20.3 | 6.3 | 28.2 | 10.1 | 28% | 100% |
| L373A | 2.4 | 11.3 | 11.2 | 27.4 | 21.6 | −7% | 87% |
| L373Q | 4.0 | 7.5 | 10.7 | 28.4 | 21.5 | −2% | 87% |
| L373V | 2.5 | 11.6 | 11.5 | 27.5 | 21.8 | −9% | 88% |
| A377I | 2.9 | 15.5 | 6.6 | 29.3 | 11.3 | 29% | 98% |
| D425Q | 1.8 | 15.3 | 5.3 | 30.3 | 9.6 | 39% | 99% |
| L428V | 5.3 | 10.5 | 6.2 | 30.8 | 8.2 | 42% | 98% |
| N475F | 6.1 | 26.8 | 20.5 | 24.9 | 7.2 | −16% | 106% |
| N475W | 1.5 | 61.8 | 7.5 | 9.1 | 1.9 | −8% | 106% |
| L513F | 1.0 | 10.9 | 4.6 | 33.3 | 7.1 | 55% | 99% |
| L513W | 1.3 | 11.5 | 4.9 | 32.4 | 8.9 | 48% | 98% |
| M529N | 3.5 | 11.6 | 4.8 | 31.6 | 7.6 | 49% | 99% |
| I608Y | 2.4 | 15.7 | 5.7 | 29.9 | 9.8 | 35% | 99% |
| N613G | 2.2 | 10.5 | 5.0 | 33.5 | 10.6 | 43% | 101% |
| N613L | 2.9 | 13.3 | 5.0 | 32.1 | 11.7 | 35% | 102% |
| D617E | 8.4 | 10.2 | 6.9 | 29.8 | 9.0 | 34% | 99% |
| E621T | 1.5 | 18.6 | 6.0 | 29.1 | 10.4 | 30% | 100% |
| I623H | 69.8 | 0.2 | 1.4 | 3.3 | 0.0 | 4% | 101% |
| I627W | 7.7 | 12.2 | 5.2 | 28.9 | 7.9 | 40% | 99% |
| S631D | 9.8 | 12.3 | 5.7 | 27.5 | 8.0 | 35% | 98% |
| S631E | 10.1 | 12.6 | 5.6 | 27.3 | 8.0 | 35% | 99% |
| S631R | 6.7 | 12.3 | 5.4 | 28.7 | 8.1 | 40% | 97% |
| G633W | 7.0 | 7.2 | 5.5 | 31.9 | 8.5 | 46% | 99% |
| F634A | 7.4 | 8.4 | 5.7 | 30.8 | 8.2 | 43% | 98% |
| T635E | 1.6 | 17.2 | 6.0 | 29.9 | 9.5 | 35% | 100% |
| T635I | 1.5 | 17.4 | 6.2 | 30.5 | 10.1 | 32% | 102% |
| T635Y | 13.8 | 8.0 | 4.6 | 28.0 | 6.7 | 43% | 99% |
| A510E | 2.5 | 5.9 | 5.5 | 34.8 | 4.3 | 66% | 99% |
| N904E | 5.7 | 6.9 | 12.6 | 32.5 | 13.5 | 15% | 98% |
| K930G | 1.4 | 19.8 | 6.2 | 28.4 | 10.0 | 30% | 99% |
| K930V | 1.4 | 19.6 | 6.3 | 28.6 | 10.0 | 30% | 100% |
| D947F | 1.4 | 20.3 | 6.2 | 27.8 | 9.9 | 29% | 99% |
| D947I | 1.4 | 19.9 | 6.3 | 28.6 | 10.7 | 27% | 100% |
| D947K | 1.4 | 19.9 | 6.2 | 28.6 | 9.7 | 30% | 100% |
| D947N | 1.4 | 20.5 | 6.3 | 27.9 | 10.0 | 28% | 99% |
| D947Q | 1.4 | 19.5 | 6.2 | 28.4 | 9.6 | 31% | 99% |
| D947S | 1.3 | 18.9 | 6.1 | 28.8 | 9.4 | 33% | 99% |
| D947V | 1.4 | 19.8 | 6.2 | 28.3 | 9.7 | 30% | 99% |
| D947Y | 1.4 | 20.7 | 6.3 | 28.1 | 10.0 | 28% | 100% |
| Q1007S | 1.3 | 18.3 | 6.1 | 29.1 | 9.6 | 33% | 99% |
| D1003N | 3.6 | 13.1 | 5.7 | 30.5 | 9.8 | 38% | 99% |
| I1026H | 1.4 | 19.4 | 6.2 | 28.7 | 9.7 | 31% | 100% |
| D1028A | 1.5 | 20.1 | 6.5 | 28.4 | 10.8 | 26% | 100% |
| D1028M | 1.5 | 20.4 | 6.6 | 28.1 | 11.1 | 24% | 100% |
| V1037A | 1.5 | 20.2 | 6.4 | 28.4 | 10.3 | 28% | 100% |
| K1041A | 4.3 | 19.6 | 6.5 | 27.0 | 10.7 | 23% | 99% |
| K1041M | 1.5 | 20.5 | 6.4 | 28.0 | 10.5 | 26% | 100% |
| D1080M | 1.4 | 20.0 | 6.4 | 28.3 | 10.1 | 29% | 99% |
| F1244P | 1.4 | 19.6 | 6.3 | 28.6 | 9.9 | 30% | 100% |
| F1244Q | 1.4 | 19.7 | 6.4 | 28.6 | 9.9 | 30% | 100% |

TABLE 3-continued

Product Profiles of GTF 6855 (SEQ ID NO: 4) and Single Amino Acid-Substituted Variants thereof

| GTF | Sucrose (g/L)$^d$ | Leucrose (g/L)$^d$ | Glucose (g/L)$^d$ | Fructose (g/L)$^d$ | Oligomers (g/L)$^{d,e}$ | Alpha-1,3 Glucan$^f$ Yield$^i$ | Fructose Balance |
|---|---|---|---|---|---|---|---|
| T1431Q | 1.4 | 20.0 | 6.2 | 28.5 | 8.9 | 33% | 100% |
| G1484P | 1.5 | 20.1 | 6.3 | 28.5 | 9.2 | 31% | 100% |
| W1437N | 1.4 | 19.5 | 6.0 | 28.9 | 8.4 | 35% | 100% |
| Dead$^g$ | 75.5 | 0.0 | 0.0 | 0.0 | 0.0 | 0% | 100% |
| Blank$^h$ | 75.5 | 0.0 | 0.0 | 0.0 | 0.0 | 0% | 100% |
| Blank$^h$ | 76.0 | 0.0 | 0.0 | 0.0 | 0.5 | -2% | 100% |

$^a$Glucan synthesis reactions were run in microtiter plate format (two plates).
$^b$GTF 6855, SEQ ID NO: 4. Reactions with this GTF were run in quadruplicate per plate.
$^c$Each listed GTF with a substitution is a version of GTF 6855 comprising a substitution at a respective position, where the position number is in correspondence with the residue numbering of SEQ ID NO: 62. The wild type residue is listed first (before residue position number) and the substituting residue is listed second (after the residue position number) (this "wild type residue-position number-variant residue" annotation format applies throughout the present disclosure).
$^d$Sucrose, leucrose, glucose, fructose and oligomers were measured as present in filtrate prepared post reaction.
$^e$"Oligomers", gluco-oligosaccharides (believed to all or mostly be of DP ≤ 7 or 8).
$^f$Insoluble alpha-1,3 glucan product.
$^g$GTF with destroyed activity was entered into the reaction.
$^h$No GTF was added to the reaction.
$^i$Alpha-glucan yield based on glucosyl.

Based on the data in Table 3, it is apparent that certain single amino acid substitutions in GTF 6855 (SEQ ID NO:4) can increase this enzyme's yield of alpha-1,3-glucan and/or decrease its leucrose yield in glucan synthesis reactions, for example.

Example 2

Analysis of the Effects of Single Amino Acid Substitutions on Other Glucosyltransferases This Example describes the effects of certain single amino acid substitutions on the activities of glucosyltransferases other than GTF 6855 (SEQ ID NO:4). In general, it appears that substitutions corresponding to (or similar to) those observed in Example 1 having a significant effect on alpha-glucan and/or leucrose yields may be useful for imparting similar effects to different glucosyltransferases.

Phe-607-Tyr

Example 1 demonstrated, for example, that substitutions in GTF 6855 (SEQ ID NO:4) at the position corresponding to position 607 of SEQ ID NO:62 affected enzyme activity (Table 3). In particular, substitutions of the Phe residue with an Asn or Trp residue both had significant effects on alpha-1,3 glucan yield (increased) and leucrose yield (decreased) compared to the respective yields of the non-substituted enzyme.

To test whether a similar substitution could similarly affect yields in a different GTF, a substitution was made at a position in GTF 7527 (GTFJ, SEQ ID NO:65) corresponding to position 607 of SEQ ID NO:62, exchanging a Phe for a Tyr residue. GTF 7527 (SEQ ID NO:65) essentially is an N-terminally truncated (signal peptide and variable region removed) version of the full-length wild type glucosyltransferase (represented by SEQ ID NO:60) from *Streptococcus salivarius* (see Table 1). Substitutions made in SEQ ID NO:65 can be characterized as substituting for native amino acid residues, as each amino acid residue/position of SEQ ID NO:65 (apart from the Met-1 residue of SEQ ID NO:65) corresponds accordingly with an amino acid residue/position within SEQ ID NO:60. In reactions comprising at least sucrose and water, the glucosyltransferase of SEQ ID NO:65 typically produces alpha-glucan having about 100% alpha-1,3 linkages and a DP$_w$ of 400 or greater (e.g., refer to U.S. Pat. Nos. 8,871,474 and 9,169,506, and U.S. Pat. Appl. Publ. No. 2017/0002336, which are incorporated herein by reference). Glucan synthesis reactions were prepared as follows using GTF 7527 (SEQ ID NO:65) or a version thereof comprising a Phe-to-Tyr substitution at the position corresponding to position 607 of SEQ ID NO:62: vessel, 250-mL indented shake flask agitated at 100 rpm; initial pH, 5.5; reaction volume, 50 mL; sucrose, 100.1 g/L; GTF, 100 U/L; KH$_2$PO$_4$, 25 mM; temperature, 25° C.; time, 20 hours. The profiles of each reaction (as measured via methodology similar to that disclosed in Example 1), which were run in duplicate, are provided in Table 4.

TABLE 4

Product Profiles of GTF 7527 (SEQ ID NO: 65) and a Single Amino Acid-Substituted Variant thereof

| GTF | Sucrose Conv. | Yield Alpha-Glucan$^d$ based on Glucosyl | Leucrose Yield | Glucose Yield | Oligomer$^c$ Yield | Fructose balance |
|---|---|---|---|---|---|---|
| 7527$^a$ | 99.7% | 29.24% | 42% | 4.20% | 28% | 105.62% |
| 7527 | 99.8% | 22.21% | 43% | 6.26% | 29% | 109.02% |
| F607Y$^b$ | 99.8% | 64.92% | 16% | 3.33% | 15% | 102.73% |
| F607Y | 99.8% | 62.97% | 17% | 3.35% | 17% | 109.17% |

$^a$GTF 7527, SEQ ID NO: 65.
$^b$F607Y, version of GTF 7527 (SEQ ID NO: 65) comprising a Phe-to-Tyr substitution at the position corresponding to position 607 of SEQ ID NO: 62.
$^c$"Oligomer", gluco-oligosaccharides (believed to all or mostly be of DP ≤ 7 or 8).
$^d$"Alpha-Glucan", insoluble alpha-1,3 glucan.

Based on the data in Table 4, it is apparent that the F607Y substitution in GTF 7527 (SEQ ID NO:65) can increase this enzyme's yield of alpha-1,3-glucan and/or decrease its leucrose yield in glucan synthesis reactions, for example.

Ala-510-Glu, Ala-510-Val, or Ala-510-Cys

Example 1 demonstrated, for example, that substitutions in GTF 6855 (SEQ ID NO:4) at the position corresponding to position 510 of SEQ ID NO:62 affected enzyme activity (Table 3). In particular, substitutions of the Ala residue with a Glu, Ile, or Val residue all had significant effects on alpha-1,3 glucan yield (increased) and leucrose yield (decreased) compared to the respective yields of the non-substituted enzyme.

To test whether these or similar substitutions could similarly affect yields in different GTFs, substitutions were made at positions in GTFs 2919 (SEQ ID NO:28), 0427 (SEQ ID NO:26), 5926 (SEQ ID NO:14), 0847 (SEQ ID NO:2), 0544 (SEQ ID NO:12), 2379 (SEQ ID NO:6), 5618 (SEQ ID NO:18), 4297 (SEQ ID NO:16), 1366 (SEQ ID NO:24), and 6907 (SEQ ID NO:36) corresponding to position 510 of SEQ ID NO:62, exchanging an Ala for a Glu, Val, or Cys residue. Each of these GTFs essentially is an N-terminally truncated (signal peptide and variable region removed) version of a full-length wild type glucosyltransferase (e.g., refer to respective GENBANK annotation information, such as that listed in Table 1). Substitutions made in each of SEQ ID NOs:28, 26, 14, 2, 12, 6, 18, 16, 24 and 36 can be characterized as substituting for native amino acid residues, as each amino acid residue/position of these sequences (apart from the Met-1 residues of each) corresponds accordingly with an amino acid residue/position within each respective full-length wild type glucosyltransferase counterpart. Table 2 lists the alpha-glucan typically produced by each of SEQ ID NOs:28, 26, 14, 2, 12, 6, 18, 16, 24 and 36 in reactions comprising at least sucrose and water.

Preparation of GTF 2919 (SEQ ID NO:28), 0427 (SEQ ID NO:26), 5926 (SEQ ID NO:14), 0847 (SEQ ID NO:2), 0544 (SEQ ID NO:12), 2379 (SEQ ID NO:6), 5618 (SEQ ID NO:18), 4297 (SEQ ID NO:16), 1366 (SEQ ID NO:24), or 6907 (SEQ ID NO:36), or versions thereof comprising a substitution at the position corresponding to position 510 of SEQ ID NO:62 was performed as follows. Codon-optimized (for *E. coli*) sequences encoding each of these GTFs were individually cloned into a suitable plasmid for bacterial expression. Each construct was then transformed into *E. coli* BL21-AI (Invitrogen, Carlsbad, CA). Transformed strains were grown in 10 mL auto-induction medium (10 g/L Tryptone, 5 g/L Yeast Extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose, 0.05% arabinose) containing 100 mg/L ampicillin at 37° C. for 20 hours under 200 rpm agitation. The cells were harvested by centrifugation at 8000 rpm at 4° C. and resuspended in 1 mL of 20 mM sodium phosphate buffer pH 6.0 with CelLytic™ Express (Sigma, St. Louise, MO) according to the manufacturer's instructions. In addition, resuspended cells were subjected to no less than one freeze-thaw cycle to ensure cell lysis. Lysed cells were centrifuged for 10 minutes at 12,000 g at room temperature. Each resulting supernatant was analyzed by SDS-PAGE to confirm expression of the particular GTF enzyme being expressed. Each supernatant was kept on ice at 4° C. until enzyme activity could be determined (within 1 hour), and/or stored at −20° C.

Glucan synthesis reactions were prepared, and the products thereof analyzed, largely according to the disclosure of U.S. Pat. Appl. Publ. No. 2014/0087431, which is incorporated herein by reference. Each reaction was run for 24-30 hours. The profiles of each reaction are provided in Table 5.

TABLE 5

Product Profiles of Various GTFs and Single Amino Acid-Substituted Variants thereof

| GTF | Sucrose Conv. | Yield Alpha-Glucan based on Glucosyl | Leucrose Yield | Glucose Yield | Oligomer Yield | Fructose balance |
|---|---|---|---|---|---|---|
| 2919[a] | 92% | 20% | 28% | 15% | 37% | 90% |
| A510E[b] | 98% | 40% | 13% | 15% | 31% | 93% |
| A510V[b] | 97% | 45% | 15% | 15% | 26% | 84% |
| A510C[b] | 95% | 35% | 19% | 15% | 32% | 87% |
| 0427[a] | 96% | 15% | 33% | 11% | 41% | 97% |
| A510E[b] | 96% | 1.0% | 40% | 16% | 43% | 104% |
| A510V[b] | | | poor conversion | | | |
| A510C[b] | 96% | 9% | 30% | 12% | 50% | 97% |
| 5926[a] | 97% | 12% | 37% | 11% | 41% | 93% |
| A510E[b] | 96% | 12% | 40% | 14% | 34% | 94% |
| A510V[b] | 97% | 25% | 31% | 14% | 31% | 81% |
| A510C[b] | 97% | −1% | 35% | 14% | 52% | 97% |
| 0847[a] | 97% | 18% | 33% | 11% | 38% | 92% |
| A510E[b] | 98% | 11% | 35% | 14% | 40% | 95% |
| A510V[b] | 80% | 32% | 21% | 16% | 31% | 80% |
| A510C[b] | 97% | 10% | 33% | 13% | 44% | 97% |
| 0544[a] | 99% | 37% | 22% | 8% | 33% | 86% |
| A510E[b] | 93% | 46% | 21% | 8% | 25% | 85% |
| A510V[b] | | | poor conversion | | | |
| A510C[b] | 92% | 39% | 16% | 9% | 37% | 90% |
| 2379[a] | 95% | 4% | 30% | 18% | 48% | 92% |
| A510E[b] | 97% | −2% | 23% | 23% | 56% | 93% |
| A510V[b] | 94% | 5% | 20% | 23% | 52% | 82% |
| A510C[b] | 93% | −10% | 37% | 21% | 53% | 101% |
| 5618[a] | 99% | 80% | 10% | 5% | 5% | 89% |
| A510E[b] | 94% | 82% | 5% | 4% | 9% | 93% |
| A510V[b] | 99% | 83% | 7% | 5% | 5% | 78% |
| A510C[b] | 98% | 83% | 9% | 4% | 4% | 96% |
| 4297[a] | 97% | 78% | 12% | 6% | 4% | 86% |
| A510E[b] | 99% | 84% | 7% | 4% | 5% | 83% |
| A510V[b] | 99% | 78% | 8% | 8% | 6% | 77% |
| A510C[b] | 80% | 71% | 8% | 9% | 7% | 84% |
| 1366[a] | 97% | 12% | 39% | 7% | 43% | 91% |
| A510E[b] | 99% | 9% | 39% | 16% | 36% | 89% |
| A510V[b] | 78% | 17% | 28% | 16% | 39% | 80% |

TABLE 5-continued

Product Profiles of Various GTFs and Single Amino Acid-Substituted Variants thereof

| GTF | Sucrose Conv. | Yield Alpha-Glucan based on Glucosyl | Leucrose Yield | Glucose Yield | Oligomer Yield | Fructose balance |
|---|---|---|---|---|---|---|
| A510C[b] | 97% | 1% | 39% | 12% | 48% | 96% |
| 6907[a] | 85% | 7% | 42% | 17% | 34% | 91% |
| A510E[b] | 89% | 14% | 35% | 25% | 26% | 94% |
| A510V[b] | | | poor conversion | | | |
| A510C[b] | | | poor conversion | | | | aGTF 2919 (SEQ ID NO: 28), 0427 (SEQ ID NO: 26), 5926 (SEQ ID NO: 14), 0847 (SEQ ID NO: 2), 0544 (SEQ ID NO: 12), 2379 (SEQ ID NO: 6), 5618 (SEQ ID NO: 18), 4297 (SEQ ID NO: 16), 1366 (SEQ ID NO: 24), or 6907 (SEQ ID NO: 36).
[b]A510E/V/C, version of listed GTF (footnote [a]) comprising a substitution with Glu, Val, or Cys at the position corresponding to position 510 of SEQ ID NO: 62.
[c]"Oligomer", gluco-oligosaccharides.

Based on the data in Table 5, it is apparent that some substitutions in various GTFs at the position corresponding to position 510 of SEQ ID NO:62 can increase a GTF's yield of alpha glucan and/or decrease its leucrose yield in glucan synthesis reactions, for example.

Example 3

Analysis of the Effects of Two or More Amino Acid Substitutions on Glucosyltransferase Selectivity Toward Alpha-Glucan Synthesis This Example describes the effects of introducing multiple amino acid substitutions to a glucosyltransferase and determining their effect on enzyme selectivity toward alpha-glucan synthesis.

Briefly, certain amino acid substitutions were made to SEQ ID NO:4 (GTF 6855, see Table 1 and Example 1 for description of this glucosyltransferase). These substitutions are listed in Table 6 below. Each variant enzyme was entered into a glucan synthesis reaction with parameters that were the same as, or similar to, the following: vessel, 250-mL indented shake flask agitated at 120 rpm; initial pH, 5.7; reaction volume, 50 mL; sucrose, 75 g/L; GTF, 1.5 mL lysate of *E. coli* cells heterologously expressing enzyme; KH$_2$PO$_4$, 20 mM; temperature, 30° C.; time, about 20-24 hours. The alpha-1,3 glucan yield of each reaction (as measured via methodology similar to that disclosed in Example 1) is provided in Table 6.

TABLE 6

Alpha-1,3 Glucan Yields of GTF 6855 (SEQ ID NO: 4) Variants with Multiple Amino Acid Substitutions

| GTF[a] | Alpha-1,3 Glucan[b] Yield[c] |
|---|---|
| A510D/F607Y/R741S | 72.6% |
| A510D/F607Y/N743S | 79.2% |
| A510D/F607Y/D948G | 88.2% |
| A510D/R741S/D948G | 74.5% |
| A510D/F607Y/R741S/D948G | 82.8% |
| A510E/F607Y/R741S/R1172C | 78.2% |
| A510D/F607Y/D820G/D948G | 87.8% |
| A510D/F607Y/D948G/R1172C | 88.6% |

TABLE 6-continued

Alpha-1,3 Glucan Yields of GTF 6855 (SEQ ID NO: 4) Variants with Multiple Amino Acid Substitutions

| GTF[a] | Alpha-1,3 Glucan[b] Yield[c] |
|---|---|
| A510D/F607Y/N743S/D948G/R1172C | 89.4% |
| A510D/F607Y/R741S/L784Q/F929L/R1172C | 79.3% |

[a]Each listed GTF is a version of GTF 6855 (SEQ ID NO: 4) comprising substitutions at respective positions, where each position number is in correspondence with the residue numbering of SEQ ID NO: 62.
[b]Insoluble alpha-1,3 glucan product.
[c]Alpha-1,3-glucan yield based on glucosyl.

Based on the data in Table 6, it is apparent that introduction of multiple amino acid substitutions to GTF 6855 (SEQ ID NO:4) can increase this enzyme's yield of alpha-1,3-glucan; for example, compare these yields to those of GTF 6855 (SEQ ID NO:4) without substitutions shown in Table 3. Each of the variant GTF enzymes listed in Table 6 also exhibited significant reductions in yields of leucrose, glucose and gluco-oligomers (data not shown).

It is apparent, for example, that a GTF with multiple substitutions such as at positions corresponding to positions 510 and/or 607 of SEQ ID NO:62 can increase a GTF's yield of alpha glucan.

Example 4

Analysis of the Effects of Additional Amino Acid Substitution Combinations on Glucosyltransferase Selectivity Toward Alpha-Glucan Synthesis This Example describes the effects of introducing multiple amino acid substitutions to a glucosyltransferase and determining their effect on enzyme selectivity toward alpha-glucan synthesis. While this analysis supplements the analysis disclosed above in Example 3, it is interesting to note that several of the additional amino acid substitution combinations provide modified glucosyltransferases with even higher alpha-1,3-glucan yields.

Briefly, certain combinations of amino acid substitutions were made to SEQ ID NO:4 (GTF 6855, see Table 1 and Example 1 for description of this glucosyltransferase) by site-directed mutagenesis of appropriate DNA templates contained in a plasmid. The plasmid sequences encoding each modified glucosyltransferase were individually sequenced to confirm the intended codon changes. Each combination of substitutions is listed in Table 7 below.

Expression plasmids encoding the modified glucosyltransferases were individually used to transform a *B. subtilis* strain containing nine protease deletions (amyE::xylRPxylAcomK-ermC, degUHy32, oppA, ΔspoIIE3501, ΔaprE, ΔnprE, Δepr, ΔispA, Δbpr, Δvpr, ΔwprA, Δmpr-ybfJ, ΔnprB). Transformed cells were spread onto LB plates supplemented with 5 μg/mL chloramphenicol. Colonies growing on these plates were streaked several times onto LB plates with 25 μg/mL chloramphenicol. Each resulting *Bacillus* strain for expressing a particular variant glucosyltransferase was then grown for 6-8 hours in LB medium containing 25 μg/mL chloramphenicol, and then subcultured into Grants II medium at 30° C. for 2-3 days. The cultures were spun at 15000 g for 30 minutes at 4° C., and the supernatants were filtered through 0.22-μm filters. The filtered supernatants, each of which contained an expressed secreted variant glucosyltransferase, were aliquoted and frozen at −80° C., and later used (below) for analyzing alpha-1,3-glucan synthesis activity.

The same amount of each variant enzyme, activity-wise, was entered into a glucan synthesis reaction with parameters that were the same as, or similar to, the following: vessel, 500-mL jacketed reactor with Teflon®-pitched blade turbine (45-degree angle) on a glass stir rod and agitated at 50-200 rpm; initial pH, 5.5; reaction volume, 500 mL; sucrose, 108 g/L; $KH_2PO_4$, 1 mM; temperature, 39° C.; time, about 18-24 hours; filtrate from a previous alpha-1,3-glucan synthesis reaction, 50 vol %. The alpha-1,3 glucan yield of each reaction (as measured via methodology similar to that disclosed in Example 1) is provided in Table 7.

TABLE 7

Alpha-1,3 Glucan Yields of GTF 6855 (SEQ ID NO: 4) Variants with Multiple Amino Acid Substitutions

| GTF[a] | | | | | | | | | | | | | Alpha-1,3-Glucan[b] Yield[c] |
|---|---|---|---|---|---|---|---|---|---|---|---|---|---|
| A510D | Q588L | F607Y | R741S | D948G |       |       |       | R722H | T877K |        | M1253I | K1277N |        | 88% |
| A510D | Q588L | F607Y | R741S | D948G |       |       |       | R722H | T877K | V1188E | M1253I | Q957P  |        | 92% |
| A510D | Q588L | F607Y | R741S | D948G |       |       |       |       | T877K | V1188E | M1253I | Q957P  |        | 91% |
| A510D | Q588L | F607Y | R741S | D948G |       |       |       |       |       |        | M1253I |        |        | 89% |
| A510D | Q588L | F607W | R741S | D948G |       |       |       |       |       |        |        |        |        | 91% |
|       | Q588L | F607Y | R741S | D948G |       |       |       |       |       |        |        |        |        | 91% |
| A510D | Q588L | F607Y | R741S | D948G | N628D | T635A |       |       | T877K |        | M1253I | F929L  | R1172C | 92% |
| A510D | Q588L | F607W | R741S | D948G | S631T | S710G |       | R722H | T877K | V1188E | M1253I |        |        | 94% |
| A510D | Q588L | F607W | R741S | D948G | S631T | S710G |       | R722H | T877K | V1188E |        |        |        | 93% |
| A510D | Q588L | F607W | R741S | D948G | S631T | S710G |       |       | T877K | V1188E | M1253I |        |        | 96% |
| A510D | Q588L | F607Y | R741S | D948G |       |       |       |       |       |        |        |        |        | 89% |
| A510D | Q588L | F607Y | R741S | D948G |       |       |       |       |       | V1188E |        |        |        | 88% |
| A510D | Q588L | F607W | R741S | D948G | S631T | S710G |       |       |       | V1188E |        |        |        | 96% |
| A510D | Q588L | F607W | R741S | D948G |       | S710G |       | R722H | T877K |        | M1253I |        |        | 96% |
| A510D | Q588L | F607Y | R741S | D948G | S631T |       |       | R722H | T877K | V1188E | M1253I |        |        | 96% |
| A510D | Q588L | F607W | R741S | D948G | S631T |       |       |       | T877K | V1188E | M1253I |        |        | 94% |
| A510D | Q588L | F607W | R741S | D948G | S631T |       |       |       |       | V1188E |        |        |        | 98% |
| A510D | Q588L | F607Y | R741S | D948G | S631T |       |       | R722H | T877K | V1188E | M1253I |        |        | 95% |
| A510D | Q588L | F607W | R741S | D948G |       |       |       |       |       | V1188E | M1253I |        |        | 93% |

[a]Each listed GTF is a version of GTF 6855 (SEQ ID NO: 4) comprising substitutions at respective positions, where each position number is in correspondence with the residue numbering of SEQ ID NO: 62.
[b]Insoluble alpha-1,3 glucan product.
[c]Alpha-1,3-glucan yield based on glucosyl.

Based on the data in Table 7, it is further apparent that introduction of multiple amino acid substitutions to GTF 6855 (SEQ ID NO:4) can increase this enzyme's yield of alpha-1,3-glucan; for example, compare these yields to those of GTF 6855 (SEQ ID NO:4) without substitutions shown in Table 3. Each of the variant GTF enzymes listed in Table 7 also exhibited significant reductions in yields of leucrose, glucose and gluco-oligomers (data not shown).

It is apparent, for example, that a GTF with multiple substitutions, including those at positions corresponding to positions 588, 607 and 741 of SEQ ID NO:62, can increase a GTF's yield of alpha glucan.

SEQUENCE LISTING

```
Sequence total quantity: 81
SEQ ID NO: 1           moltype = DNA   length = 4308
FEATURE                Location/Qualifiers
source                 1..4308
                       mol_type = other DNA
                       organism = Streptococcus sobrinus
SEQUENCE: 1
atggttgacg gcaaatacta ctattatgat caggacggta acgtaaagaa gaatttcgcg    60
gtgagcgttg gtgacaaaat ctactactcc gatgaaactg gtgcatataa ggataccagc   120
aaagtggacg ccgacaagag cagcagcgcg gttagccaaa acgcgaccat ctttgcggcg   180
aataaccgtg cgtacagcac ctctgcaaag aattttgaag cggtggataa ctacctgacc   240
```

```
gcagacagct ggtatcgtcc gaaatccatc ctgaaggacg gcaaaacctg gaccgagagc   300
ggtaaggatg atttccgtcc actgctgatg gcatggtggc ctgacaccga aactaagcgc   360
aactacgtga actatatgaa taaagtggtc ggtattgaca agacgtacac tgcggaaacg   420
tcgcaagcga atttgaccgc agcggcgagc tggttcaagc gcgtatcga gcagaagatt    480
accagcgaaa acaacaccaa atggctgcgc gaagcaatct ccgcgttcgt taagacgcag   540
cctcagtgga acggcgagtc cgaaaagccg tatgacgatc acttgcagaa cggtgcgctg   600
ctgtttgata accaaaccga cctgacgcca gacacccaaa gcaattaccg tttgctgaac   660
cgtacccgca ccaatcagac tggtagcctg atagccgtt ttacgtataa tccgaatgac    720
ccgttgggcg gctacgtttt cttgctggcg aacgacgttg acaatagcaa tccggtcgtc   780
caggctgaac agttgaactg gctgcattat ctgctgaact ttggctctat ttacgctaac   840
gatgccgacg ccaattttga cagcattcgc gttgatgccg tcgataatgt cgatgctgat   900
ctgctgcaaa tcagcagcga ttacctgaaa gcagcgtatg catcgacaa gaataacaag    960
aatgcgaaca accatgttag catcgtcgaa gcgtggagcg acaatgatac cccgtatttg  1020
cacgacgatg gcgataaatc tgatgaacatg gacaacacat ttcgcctgtc catgctgtgg  1080
agcctggcaa agccgctgga caaacgtagc ggtttgaacc cgctgattca caatagcctg  1140
gtggaccgcg aggtggacga tcgtgaagtg gaaaccgtgc cgtcctacag ctttgctcgt  1200
gcacatgata gcgaggtgca ggacatcatc cgtgacatta tcaaggctga gattaaccca  1260
aatagctttg gttatagctt cactcaagaa gagatcgaca agccttttaa gatttacaac  1320
gaggatttga agaaaacgga caagaaatac acccactaca atgtgccgct gagctacacc  1380
ctgctgctga ccaacaaggg cagcatcccg cgtgtgtact atggtgatat gttcaccgat  1440
gatggccaat acatggcaaa caagaccgtc aactacgacg caatcgagag cctgctgaaa  1500
gcccgtatga aatatgtcag cggtggccaa gcaatgcaga tatatcaaat tggtaatgac  1560
gagattttga ccagcgtgcg ctatggtaaa ggtgccctga gcagagcga taagggtgac  1620
gcgacgacgc gcactagcgg tgttggcgtg gttatgggta atcagccgaa cttctccctg  1680
gacggtaaag ttgtggccct gaatatgggt gcggcccatg cgaatcaaga ataccgtgca  1740
ctgatgctca gcactaaaga cggtgtggca acttacgcaa ccgatgctga cgcatccaaa  1800
gcgggcctgg tcaagcgtac cgacgagaac ggctacctgt acttcctgaa tgatgatctg  1860
aagggcgtcg cgaaccctca ggtttccggc ttcttgcaag tgtgggttcc agttggtgcc  1920
gccgatgacc aggacattcg cgtcgccgcc agcgacacgg cgagcacgga tggtaaaagc  1980
ctgcatcaag atgcggcgat ggacagccgc gtcatgtttg agggttttcag caattttcaa  2040
tccttcgcga ccaaagaaga agaatacacg aatgttgtta tcgcgaacaa tgtcgataag  2100
ttcgttagct ggggtatcac cgattttgaa atggctccgc agtatgttag cagcaccgac  2160
ggtcagttct tggacagcgt catccagaat ggctatgcgt ttactgatcg ctatgatctg  2220
ggtatgtcca aggcgaacaa cgtatgcacg gcagaccaac tggttaaggc aatcaaagcc  2280
ctgcacgcta aaggcctgaa agttatggcg gactgggtcc cggatcaaat gtacaccttt  2340
ccaaaacagg aagttgtgac cgttaccgc accgacaaat tcggtaaacc gatcgccggc  2400
tctcaaatca atcacagctt gtatgtgacc gacaccaaat ccagcggcga cgactaccaa  2460
gcgaagtacg gcggtgcctt cctggatgaa ctgaaagaa agtacccgga actgttcacg  2520
aaaaagcaaa ttagcacggg ccaagcgatt gatccgaccg tgaaatcaa gcagtggagc  2580
gcaaaatact tcaatggttc gaatatcctg ggtcgcggtg cggactatgt gctgagcgac  2640
caggtcagca ataagtattt caacgtgcg agcgacacct tgttcctgcc gtccagcctg  2700
ctgggcaagg tcgtggagag cggcattcgt tacgacggca agggttacat ctacaacagc  2760
tccgcaccgg gcgatcaggt caaagcgtct ttcattacgg aagccggtaa cctgtattac  2820
ttcggcaaag acggttacat ggttactggt gcccagacga ttaatggcgc caactacttc  2880
ttcctggaaa acggtacggc actgcgtaat acgatttaca ccgatgctca aggtaatagc  2940
cactattacg cgaatgatgg caaacgctat gaaaatggct atcaacagtt cggtaacgat  3000
tggcgctact ttaaagatgg taacatggca gtcggcctga gtccggttga tggcaactg  3060
caatactttg acaaagacgg cgtccaggca aaggataaga ttatcgtcac cgtgatggc   3120
aaggtccgtt acttcgatca gcacaacggt aacgcggcga ccaacacgtt cattgctgat  3180
aaaactggcc attggtatta cctgggtaaa gatgcgtcg cggtgactgg cgcccagacc  3240
gtcggcaaac aaaaactgta cttcgaggcc aacggtcaac aagttaaagg tgacttgtca  3300
acgtccgatg agggcaaact gtatttctat gacgttgatt ctggtgacat gtggacggac  3360
accttcatcg aggataaggc gggcaactgg ttctatttgg caaggatgg tgcggcagtt  3420
acgggtgccc aaacgattcg cggtcagaag ctgtacttca aggccaatgg tcaacaggtc  3480
aagggtgaca ttgttaaggg caccgacggt aaaatccgct actatgcgc aaaatcgggt  3540
gaacaggtgt tcaacaaaac ggtgaaagct gcggatgcaa aaacgtatgt tatcggtaat  3600
gatggtgtcg cggtggaccc tagcgtggtt aaaggtcaaa cctttaagga cgcttcgggc  3660
gctctgcgtt tctacaactt gaagggtcaa ctggtcactg gcagcggctg gtatgaaacc  3720
gcgaaccatg actgggttta cattcagtcc ggcaaggcac tgaccggcga acagaccatt  3780
aacggtcaac acctgtattt caaagaagat ggtcaccaag tcaaggcta gttggtcacg  3840
ggcaccgatg gtaaagtgcg ttactatgac gccaacagcg gtgaccaagc attcaacaag  3900
agcgtcactg tgaatggtaa aacctatac tttggcaacg atggtacggc cagactgct    3960
ggcaacccga gggtcagac gttcaaggat ggctccgaca tccgtttta ctctatggaa    4020
ggcaactgg tgaccggctc gggttggtac gagaacggca aaggccagtg gctgtaatg   4080
aaaaacggta aggtgctgac tggtctgcaa accgttggca gccagcgtgt ttacttcgac  4140
gagaatggta ttcaggccaa gggcaaagca gtgcgtacca gcgatggcaa aattcgttat  4200
ttcgacgaaa acagcggcag catgatcacg aatcaatgga agttcgtcta tggtcagtat  4260
tactactttg gtaacgacgg tgcacgtatt taccgtggtt ggaactaa               4308

SEQ ID NO: 2              moltype = AA   length = 1435
FEATURE                   Location/Qualifiers
source                    1..1435
                          mol_type = protein
                          organism = Streptococcus sobrinus
SEQUENCE: 2
MVDGKYYYYD QDGNVKKNFA VSVGDKIYYF DETGAYKDTS KVDADKSSSA VSQNATIFAA   60
NNRAYSTSAK NFEAVDNYLT ADSWYRPKSI LKDGKTWTES GKDDFRPLLM AWWPDTETKR  120
NYVNYMNKVV GIDKTYTAET SQADLTAAAE LVQARIEQKI TSENNTKWLR EAISAFVKTQ  180
PQWNGESEKP YDDHLQNGAL LFDNQTDLTP DTQSNYRLLN RTPTNQTGSL DSRFTYNPND  240
```

-continued

```
PLGGYDFLLA NDVDNSNPVV QAEQLNWLHY LLNFGSIYAN DADANFDSIR VDAVDNVDAD  300
LLQISSDYLK AAYGIDKNNK NANNHVSIVE AWSDNDTPYL HDDGDNLMNM DNKFRLSMLW  360
SLAKPLDKRS GLNPLIHNSL VDREVDDREV ETVPSYSFAR AHDSEVQDII RDIIKAEINP  420
NSFGYSFTQE EIEQAFKIYN EDLKKTDKKY THYNVPLSYT LLLTNKGSIP RVYYGDMFTD  480
DGQYMANKTV NYDAIESLLK ARMKYVSGGQ AMQNYQIGNG EILTSVRYGK GALKQSDKGD  540
ATTRTSGVGV VMGNQPNFSL DGKVVALNMG AAHANQEYRA LMVSTKDGVA TYATDADASK  600
AGLVKRTDEN GYLYFLNDDL KGVANPQVSG FLQVWVPVGA ADDQDIRVAA SDTASTDGKS  660
LHQDAAMDSR VMFEGFSNFQ SFATKEEEYT NVVIANNVDK FVSWGITDFE MAPQYVSSTD  720
GQFLDSVIQN GYAFTDRYDL GMSKANKYGT ADQLVKAIKA LHAKGLKVMA DWVPDQMYTF  780
PKQEVVTVTR TDKFGKPIAG SQINHSLYVT DTKSSGDDYQ AKYGGAFLDE LKEKYPELFT  840
KKQISTGQAI DPSVKIKQWS AKYFNGSNIL GRGADYVLSD QVSNKYFNVA SDTLFLPSSL  900
LGKVVESGIR YDGKGYIYNS SATGDQVKAS FITEAGNLYY FGKDGYMVTG AQTINGANYF  960
FLENGTALRN TIYTDAQGNS HYYANDGKRY ENGYQQFGND WRYFKDGNMA VGLTTVDGNV 1020
QYFDKDGVQA KDKIIVTRDG KVRYFDQHNG NAATNTFIAD KTGHWYYLGK DGVAVTGAQT 1080
VGKQKLYFEA NGQQVKGDFV TSDEGKLYFY DVDSGDMWTD TFIEDKAGNW FYLGKDGAAV 1140
TGAQTIRGQK LYFKANGQQV KGDIVKGTDG KIRYYDAKSG EQVFNKTVKA ADGKTYVIGN 1200
DGVAVDPSVV KGQTFKDASG ALRFYNLKGQ LVTGSGWYET ANHDWVYIQS GKALTGEQTI 1260
NGQHLYFKED GHQVKGQLVT GTDGKVRYYD ANSGDQAFNK SVTVNGKTYY FGNDGTAQTA 1320
GNPKGQTFKD GSDIRFYSME GQLVTGSGWY ENAQGQWLYV KNGKVLTGLQ TVGSQRVYFD 1380
ENGIQAKGKA VRTSDKIRY  FDENSGSMIT NQWKFVYGQY YYFGNDGARI YRGWN      1435

SEQ ID NO: 3          moltype = DNA   length = 4026
FEATURE               Location/Qualifiers
source                1..4026
                      mol_type = other DNA
                      organism = Streptococcus salivarius
SEQUENCE: 3
atgatcgacg gcaaatacta ttatgttaat gaggacggta gccacaaaga aaactttgcg   60
attacggtta atggtcaact gctgtatttc ggtaaggacg gcgcactgac ctctagcagc  120
acttacagct ttaccccagg tacgacgaac atcgtggatg gcttttctat caacaaccgc  180
gcgtatgact ccagcgaagc gtcctttgaa ctgattgatg gctacttgac tgccgactcc  240
tggtatcgtc cggcttccat catcaaggac ggtgtcacgt ggcaggccag caccgcagag  300
gactttcgcc gctgctgat  ggcgtggtgg ccaaacgtgg ataccaggt  gaactatctg  360
aactacatgt ctaaagtgtt taacctggac gcaaagtata gcagcaccga taaacagtgg  420
actctgaagg ttgcagctaa ggatattcag attaagatcg agcagaaaat tcaggcggag  480
aaaagcaccc aatggctgcg cgaaacgatc agcgcttttg tgaaaaccca accacagtgg  540
aacaaagaga ctgagaatta ctcgaaaggt ggtggtgagg atcatctgca aggcggtgca  600
ctgctgtacg tgaatgatag ccgtaccccg tgggcaaata gcgattatcg ccgcctgaac  660
cgcaccgcta ccaatcaaac gggtacgatt gacaagtcca ttctgacgga gcagagcgac  720
ccaaatcaca tgggcggttt cgacttcctg ctgcgaatg  atgttgacct gtccaacccg  780
gttgtgcagg cagagcagct gaaccagatt cactacttga tgaattgggg ctctatcgtg  840
atgggtgaca agacgcaaa  cttggatgg  atccgtgtcg atgcagttga aacgtcgat   900
gccaactgta tgcaactgta taccaactac ttccgtgaat actacggtgt taacaaaagc  960
gaagcgaacg cactggcgca cattagcgtt ttggaagcgt ggagcttgaa tgataatcac 1020
tacaacgaca aaaccgatgg tgcagcattg gcgatggaga ataagcagcg tctggcgctg 1080
ctgtttagcc tggctaaacc gattaaagag cgcacccggg cagtgagccc gctgtataac 1140
aacaccttca atacgaccca acgcgatgag aaaaccgatg gatcaataa  agacggttct 1200
aaggcctata cgaggatgg  tactgtgaag cagagcacca ttggtaagta caatgaaaaa 1260
tatggtgatg catcgggcaa ttatgtgttc atccgtgccc atgataacaa tgtccaagac 1320
atcattgcgc agatcattaa gaaagaaatc aacccgaaaa gcgatggttt caccatcact 1380
gacgccgaaa tgaaacaagc gttcgagatt tacaataagg acatgctgag cagcgacaag 1440
aagtacaccc tgaataacat cccggcagct tatgccgtga tgttcagaa  catgcaaacg 1500
attcccgtg  tctattatgg tgacctgtac accgacgacg ccactacat  ggaaaccaag 1560
tccccgtatt acgacaccat cgttaacctg atgaaaagcc gtatcaagta cgtcagcggt 1620
ggcaggcc   aacgtagcta ctggctgccg accgacggaa tagcgacgtt 1680
gagctgtatc gcaccaacga agtgtatacc agcgtccgtt acggtaaaga cattatgacc 1740
gcgaacgata ccgagggtag caagtacagc cgcaccagcg gccaggtcac cctggttgca 1800
aacaacccga agctgaccct ggaccagagc gcgaagctga atgtgaaat  gggtaagat  1860
cacgcgaatc agaaatacc  tgccctgatt gtgggcacgg ctgccggtat caagaattc  1920
accagcgacg cagatgctat cgcggcaggc tacgtgaaag aaaccgactc caatgcgtt  1980
ctgacttttg cgctaatga  catcaaaggt tatgaaacct cgacatgtc  cggctttgtt 2040
gctgtttggg tgccggtcgg cgcgagcgat gatcaggaca ttcgtgtcgc tcctagcact 2100
gaggccaaga aagagggtga attgaccctg aaagcgaccg aagcatacga ttcccagctg 2160
atctatgaag gttttagcaa ttttcaaacc atcccgtacg gtacgaccc  gagcgtgtga 2220
accaatcgca agatcgcaga gaacgtggac ctgttcaagt cctggggtgt tacctcgttt 2280
gaaatggcac cgcagttcgt ttccgcagat gatggcactt ttctggactc tgtgatccaa 2340
aacggctatg cgtttgccga tcgttacgat ttggcgatga gcaagaacaa caatacggc  2400
agcaaagagg acttgcgtga cgcgctgaaa gccctgcata aagcaggcat ccgtgcgatt 2460
gcagactgtg tcccggacca gatttatcag ttgccgacga aagaagtggt cacggcgact 2520
cgcaccgacg gcgcaggccg taaaatcgcg gacgcgatca ttgatcatag cctgtacgtt 2580
gcgaacacta gagcagcgg  caaagattac caggcgaagt acggtggtga gttcttggcg 2640
gagctgaagg ccaagtaccc ggagatgttc aaagtgaaca tgatttctac cggcaaaccg 2700
attgatgaca gcgtcaaact gaaacagtgg aaagcagaat actttaacgg caccaacgtc 2760
ttggagacgg gtgtgggtta tgtcctgagc gatgaagcca cgggtaaata cttaccgtc  2820
acgaaggatg gcaacttcat tccgttgcag ctgacgggta tgagaaagt  cgtgaccggc 2880
tttagcaatg atgcaaagg  tatcacctac ttcggtacga gcggcactca agcgaaatct 2940
gcgttcgtta cgtcaatgg  taatacttac tattttgacg ctcgtggtca catggttacg 3000
aacgcgagt  attcgccgaa cggtaaggat gtttaccgtt tcctgccgaa tggtattatg 3060
ctgtctaacg cttttttacgt tgatgcaaat ggtaacacgt acctgtacaa cagcaagggc 3120
```

-continued

```
caaatgtaca aaggcggtta caccaaattt gacgttaccg aaacggacaa agatggtaag  3180
gaaagcaagg tggtgaagtt tcgttacttt acgaacgaag gtgtcatggc aaaaggcgtt  3240
accgtgattg acggcttcac gcaatacttt ggtgaagatg gtttccaagc gaaagacaag  3300
ctggtcacgt tcaagggcaa gacgtactac ttcgatgcac acaccggcaa tgcgatcaag  3360
gacacctggc gtaatatcaa tggcaagtgg tatcatttcg acgaacgga cgttgcagcg  3420
accggcgctc aggtcatcaa tggccaaaaa ctgtatttca acgaggacgg cagccaagtg  3480
aaaggcggtg ttgtcaaaaa cgcggacggt acgtattcta aatacaaaga gggttctggt  3540
gaactggtta ccaacgagtt cttcacgacg gatggcaatg tttggtacta cgcaggcgcg  3600
aatggcaaga ccgttacggg tgcccaggtg attaacggcc aacacctgta cttcaatgcg  3660
gacggttcgc aagtgaaggg cggtgtggtc aagaacgcgg atggcaccta tagcaaatat  3720
gatgcgtcta ccggcgaacg cctgaccaat gagtttttca ccacgggtga taacaactgg  3780
tactacattg gcgcaaacgg caagagcgtg acgggcgagg tcaagatcgg tgacgatacc  3840
tatttctttg ccaaagatgg caagcaagtt aagggtcaaa ctgtcagcgc gggtaacggt  3900
cgtattagct actactatgg tgatagcggt aagcgtgcgg tgagcacttg gatcgaaatc  3960
caaccgggtg tttatgtcta cttcgacaag aacggcattg cctatccgcc tcgtgtgctg  4020
aattaa                                                            4026

SEQ ID NO: 4          moltype = AA   length = 1341
FEATURE               Location/Qualifiers
source                1..1341
                      mol_type = protein
                      organism = Streptococcus salivarius
SEQUENCE: 4
MIDGKYYYVN EDGSHKENFA ITVNGQLLYF GKDGALTSSS TYSFTPGTTN IVDGFSINNR   60
AYDSSEASFE LIDGYLTADS WYRPASIIKD GVTWQASTAE DFRPLLMAWW PNVDTQVNYL  120
NYMSKVFNLD AKYSSTDKQE TLKVAAKDIQ IKIEQKIQAK KSTQWLRETI SAFVKTQPQW  180
NKETENYSKG GGEDHLQGGA LLYVNDSRTP WANSDYRRLN RTATNQTGTI DKSILDEQSD  240
PNHMGGFDFL LANDVDLSNP VVQAEQLNQI HYLMNWGSIV MGDKDANFDG IRVDAVDNVD  300
ADMLQLYTNY FREYYGVNKS EANALAHISV LEAWSLNDNH YNDKTDGAAL AMENKQRLAL  360
LFSLAKPIKE RTPAVSPLYN NTFNTTQRDE KTDWINKDGS KAYNEDGTVK QSTIGKYNEK  420
YGDASGNYVF IRAHDNNVQD IIAEIIKKEI NPKSDGFTIT DAEMKQAFEI YNKDMLSSDK  480
KYTLNNIPAA YAVMLQNMET ITRVYYGDLY TDDGHYMETK SPYYDTIVNL MKSRIKYVSG  540
GQAQRSYWLP TDGKMDNSDV ELYRTNEVYT SVRYGKDIMT ANDTEGSKYS RTSGQVTLVA  600
NNPKLTLDQS AKLNVEMGKI HANQKYRALI VGTADGIKNF TSDADAIAAG YVKETDSNGV  660
LTFGANDIKG YETFDMSGFV AVWVPVGASD DQDIRVAPST EAKKEGELTL KATEAYDSQL  720
IYEGFSNFQT IPDGSDPSVY TNRKIAENVD LFKSWGVTSF EMAPQFVSAD DGTFLDSVIQ  780
NGYAFADRYD LAMSKNNKYG SKEDLRDALK ALHKAGIQAI ADWVPDQIYQ LPGKEVVTAT  840
RTDGAGRKIA DAIIDHSLYV ANTKSSGKDY QAKYGGEFLA ELKAKYPEMF KVNMISTGKP  900
IDDSVKLKQW KAEYFNGTNV LERGVGYVLS DEATGKYFTV TKDGNFIPLQ LTGNEKVVTG  960
FSNDGKITY FGTSGTQAKS AFVTFNGNTY YFDARGHMVT NGEYSPNGKD VYRFLPNGIM  1020
LSNAFYVDAN GNTYLYNSKG QMYKGGYTKF DVTETDKDGK ESKVVKFRYF TNEGVMAKGV  1080
TVIDGFTQYF GEDGFQAKDK LVTFKGKTYY FDAHTGNAIK DTWRNINGKW YHFDANGVAA  1140
TGAQVINGQK LYFNEDGSQV KGGVVKNADG TYSKYKEGSS ELVTNEFFTT DGNVWYYAGA  1200
NGKTVTGAQV INGQHLYFNA DGSQVKGGVV KNADGTYSKY DASTGERLTN EFFTTGDNNW  1260
YYIGANGKSV TGEVKIGDDT YFFAKDGKQV KGQTVSAGNG RISYYYGDSG KRAVSTWIEI  1320
QPGVYVYFDK NGIAYPPRVL N                                          1341

SEQ ID NO: 5          moltype = DNA   length = 3744
FEATURE               Location/Qualifiers
source                1..3744
                      mol_type = other DNA
                      organism = Streptococcus salivarius
SEQUENCE: 5
atgccaagcc acattaagac catcaacggc aaacaatact acgtggagga tgacggtacg    60
attcgcaaga attacgtcct ggagcgtatc ggtggcagcc aatactttaa tgcagaaacc   120
ggtgaactgt ctaatcagaa agagtatcgt ttcgacaaaa atggtggtac tggtagcagc   180
gcggacagca cgaacaccaa cgtgactgtg aacggtgaca aaaacgcatt ttacggtacc   240
acggacaaag acattgagct ggtcgacggc tatttcaccg cgaacacctg gtatcgcccg   300
aaagaaatcc tgaaagacgg caaagaatgg accgccagca cggagaacga taaacgccag   360
ctgctgaccg tctcggtggc ctagcaaagca atccaggcgt cttatctgaa ctacatgaaa   420
gagcaaggcc tgggtaccaa ccaaacgtac acgagcttct ccagccaaac ccaaatggat   480
caagcagccc tggaagtgca aaagcgtatt gaagagcgca tcgcacgcga gggcaatacc   540
gactggctgc gcacgaccat caagaacttc gtgaaaaccc aacgggttg gaacagcacc   600
tctgaaaatc tggacaataa tgatcatctg caaggtgcgc cctgctgta caataacgac   660
tcccgcacga gccacgcgaa cagcgactat cgcctgctga atcgtacgcc gaccagccag   720
accggcaaac acaatccgaa ataccacaaa gataccagca atggtggttt cgaatttctg   780
ctggcgaacg acatcgataa ctctaatccg gcggttcaag cagagcaact gaactggctg   840
cattacatta tgaacatcgg taccatcacg gcggttctg aggatgaaaa cttcgacggc   900
gttcgtgttg acgctgtgga taatgtgaat gcggatctgc tgcaaatcgc tgacgactat   960
ttcaaagcaa aatacggtgc tgatcaaagc caagatcagg cgatcaaaca cttgagcatc  1020
ctggaagcgt ggtcccataa cgacgcctac tataacgaag ataccaaagg cgcgcagttg  1080
ccgatggatg atccgatgca cctggctctg gtctactcgc tgctgcgtcc gatcggcaat  1140
cgcagcggtg tggaaccgct gatttccaac agcctgaatg accgtagcga gtccggtaag  1200
aacagcgtga acagcgtgaa ctacgcgttc ataccgaagg atgcgaagtt cctttcactgg  1260
attattggcc agatcatcaa aaacgagatc aatccgcaaa gcaccggtaa tacgttcacc  1320
ctggatgaga tgaagaaagc gtttgagatt tacaacaaga atatgcgtag cgcgaataag  1380
cagtatacgc agtacaacat cccgagcgcg tatgcgttga tgctgaccca aggatacc  1440
gttccgcgtg tgtattacgg tgatatgtat acggacgacg tcagtacat ggcgcaaaag  1500
agcccatact atgatgcgat cgaaacgctg ctgaaaggtc gcatccgcta tgccgcaggt  1560
```

-continued

```
ggtcaggaca tgaaggtcaa ctatattggt tacggtaaca ctaacggctg ggatgctgcg    1620
ggcgtgctga ccagcgtacg ttatggcacg ggcgcaaata cgccagcga tacgggtacc    1680
gccgaaacgc gtaatcaagg tatggcagtg attgttagca accaccggc gctgcgtctg    1740
actagcaatt tgaccattaa catgggtgcc gcacaccgta atcaggctta ccgtccgctg    1800
ctgctgacga ccaacgatgg cgtcgcgacc tatttgaacg atagcgatgc gaatggtatc    1860
gttaagtaca ccgacggtaa tggtaatctg accttctccg caaacgagat tcgtggcatc    1920
cgtaacccgc aagttgatgg ctatctggcc gtctgggttc cggtaggtgc gtcggagaat    1980
caggatgttc gtgtggcgcc gagcaaagag aagaacagct ccggtctggt ttacgagagc    2040
aatgctgccc tggatagcca agttatctac gaaggcttca gcaacttcca ggacttcgtt    2100
cagaatccga gccagtatac caacaaaaag attgcagaga atgcaaatt gttcaaatcc    2160
tggggtatta ccagctttga atttgcgccg cagtacgtga gctcggatga tggtagcttc    2220
ctggacagcg ttattcagaa cggttatgcg tttacggacc gctacgacat tggtatgagc    2280
aaagacaaca aatatggttc gctggcggat ttgaaggcag cactgaagag cttgcatgcc    2340
gttggtatta gcgcaatcgc ggattgggtt cctgatcaga tctacaatct gccaggcgac    2400
gaggtcgtca ccgcaacccg cgttaacaac tacggcgaaa ccaaagatgg tgcaatcatt    2460
gatcactctt tgtacgcggc caaaacccgt acttttggta acgactacca gggtaagtat    2520
ggtggtcgct tcctggacga gctgaaacgt ctgtatccgc agatctttga ccgcgttcag    2580
atttctaccg gtaagcgcat gaccacggac gagaagatca cccaatggtc tgcaaagtat    2640
atgaacggta cgaacatctt ggaccgtggc tctgaatacg tttttgaagaa tggtctgaat    2700
ggttactatg gcaccaatgg tggcaaagtt tcgctgccga agttgtggg tagcaatcaa    2760
agcacgaatg gcgacaatca aaacggcgac ggtagcggca gtttgaaaaa gcgtctgttc    2820
agcgtcgatt accgttataa caatggccag tacgcgaaaa atgcctttat caaagataac    2880
gacggcaatg tttactattt cgacaatagc ggtcgtatgg ctgtcggtga gaaaacgatt    2940
gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg gtgcaattcg ctactatgac gcgaatagcg gtgagatggc acgcaatcgt    3300
ttcgcggaga ttgaaccggg cgtctgggca tactttaaca atggcgacgt cgcagtgaag    3360
ggttctcaga atatcaatgg tcaagacctg tacttcgacc agaacggtcg tcaggtcaag    3420
ggtgcgctgg ccaatgttga tggcaacctg cgctattacg acgttaacag cggtgagctg    3480
taccgtaatc gtttccacga aatcgacggc agctggtatt actttgatgg taacggtaat    3540
gcggtcaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagccag gttggtgggt ttactttgac    3720
ggtgaaggtc gtggtcagat ctaa                                          3744
```

```
SEQ ID NO: 6         moltype = AA   length = 1247
FEATURE              Location/Qualifiers
source               1..1247
                     mol_type = protein
                     organism = Streptococcus salivarius
SEQUENCE: 6
MPSHIKTING KQYYVEDDGT IRKNYVLERI GGSQYFNAET GELSNQKEYR FDKNGGTGSS     60
ADSTNTNVTV NGDKNAFYGT TDKDIELVDG YFTANTWYRP KEILKDGKEW TASTENDKRP    120
LLTVWWPSKA IQASYLNYMK EQGLGTNQTY TSFSSQTQMD QAALEVQKRI EERIAREGNT    180
DWLRTTIKNF VKTQPGWNST SENLDNNDHL QGGALLYNND SRTSHANSDY RLLNRTPTSQ    240
TGKHNPKYTK DTSNGGFEFL LANDIDNSNP AVQAEQLNWL HYIMNIGTIT GGSEDENFDG    300
VRVDAVDNVN ADLLQIASDY FKAKYGADQS QDQAIKHLSI LEAWSHNDAY YNEDTKGAQL    360
PMDDPMHLAL VYSLLRPIGN RSGVEPLISN SLNDRSESGK NSKRMANYAF VRAHDSEVQS    420
IIGQIIKNEI NPQSTGNTFT LDEMKKAFEI YNKDMRSANK QYTQYNIPSA YALMLTHKDT    480
VPRVYYGDMY TDDGQYMAQK SPYYDAIETL LKGRIRYAAG GQDMKVNYIG YGNTNGWDAA    540
GVLTSVRYGT GANSASDTGT AETRNQGMAV IVSNQPALRL TSNLTINMGA AHRNQAYRPL    600
LLTTNDGVAT YLNDSDANGI VKYTDGNGNL TFSANEIRGI RNPQVDGYLA VWVPVGASEN    660
QDVRVAPSKE KNSSGLVYES NAALDSQVIY EGFSNFQDFV QNPSQYTNKK IAENANLFKS    720
WGITSFEFAP QYVSSDDGSF LDSVIQNGYA FTDRYDIGMS KDNKYGSLAD LKAALKSLHA    780
VGISAIADWV PDQIYNLPGD EVVTATRVNN YGETKDGAII DHSLYAAKTR TFGNDYQGKY    840
GGAFLDELKR LYPQIFDRVQ ISTGKRMTTD EKITQWSAKY MNGTNILDRG SEYVLKNGLN    900
GYYGTNGGKV SLPKVVGSNQ STNGDQNGD GSGKFEKRLF SVRYRYNNGQ YAKNAFIKDN    960
DGNVYYFDNS GRMAVGEKTI DGKQYFFLAN GVQLRDGYRQ NRRGQVFYYD QNGVLNANGK   1020
QDPKPDNNNN ASGRNQFVQI GNNVWAYYDG NGKRVTGHQN INGQELFFDN NGVQVKGRTV   1080
NENGAIRYYD ANSGEMARNR FAEIEPGVWA YFNNDGTAVK GSQNINGQDL YFDQNGRQVK   1140
GALANVDGNL RYYDVNSGEL YRNRFHEIDG SWYYFDGNGN AVKGMVNING QNLLFDNNGK   1200
QIKGHLVRVN GVVRYFDPNS GEMAVNRWVE VSPGWWVYFD GEGRGQI                 1247
```

```
SEQ ID NO: 7         moltype = DNA   length = 4434
FEATURE              Location/Qualifiers
source               1..4434
                     mol_type = other DNA
                     organism = Streptococcus salivarius
SEQUENCE: 7
atggacgaaa cgcaggataa gaccgtgacg cagagcaaca gcggcaccac cgcttccctg     60
gtcactgcc ctgaagcac gaaagaggcg gacaaacgca gaacactaa agaggccgac    120
gttctgacgc ctgcaaaaga aacgaacgca gtcgagactg cgaccaccac taacacccag    180
gcgacggcgg aggccgccac gaccgcgacc accgcggacg tcgcggtggc tgcggtgccg    240
aacaaagaag cggtcgttac cacgcgatgct ccggcggtca cgaccgagaa gcggaagaa    300
cagccggcta ccgttaaagc agaagtcgtc aatacggaag tgaaagcgcc ggaagcggct    360
ctgaaagaca gcgaggttga ggcagcgctg agcctgaaga acatcaagaa cattgatggc    420
```

-continued

```
aagtattact atgttaatga ggatggcagc cacaaagaga atttcgctat taccgtgaat    480
ggccagctgc tgtactttgg taaagacggt gcgctgacgt cctctagcac gtattctttt    540
accccaggca ctaccaatat cgtgacggt tttagcatta caaccgcgc ttacgacagc     600
agcgaggcga gctttgagct gatcgacggt tacttgaccg cagacagctg gtatcgtccg    660
gctagcatca tcaaagatgg tgttacgtgg caagcgtcca ccgccgagga ttttcgtccg    720
ctgctgatgg catggtggcc gaatgtggat acgcaggtga actatttgaa ttacatgtcc    780
aaagttttca acctggacgc gaaatactct agcaccgaca acaggaaaac cctgaaagtg    840
gcagcaaaag acattcaaat caagattgaa caaaagattc aagcggagaa gagcacgcag    900
tggctgcgtg aaactatcag cgcctttgtg aaaacccagc cgcagtggaa caaagaaacc    960
gagaattaca gcaagggtgg tggtgaggac cacctgcaag gtggcgcact gctgtatgtt   1020
aacgacagcc gtacccttg ggcgaatagc gattaccgtc gtctgaatcg caccgcaacc   1080
aatcagacgg gcacgatcga taagtctatt ctggacgagc agtctgaccc aaaccacatg   1140
ggcggtttcg actttctgct ggcgaacgac gtcgacctga gcaatccggt cgtgcaggct   1200
gagcagctga atcaaatcca ctatctgatg aattgggggtt ccattgtgat gggtgacaag   1260
gatgcgaact ttgacggcat tcgtgtcgat gcagttgaca acgttggacgc ggacatgttg   1320
caactgtata ccaattactt ccgtgagtac tacggtgtga caagagcga agctaacgca   1380
ctggctcaca tcagcgttct ggaggcgtgg agcctgaatg ataatcatta caatgacaag   1440
accgatggtg cggcactggc aatggagaat aagcaacgtc tggcgctgtt gttttcgttg   1500
gcgaaaccga tcaaagagcg taccccggca gtgagcccgc tgtataacaa caccttcaat   1560
accaccagc gtgatgaaaaa gaccgattgg attaacaaag acgtagcaa ggcttacaac   1620
gaagatggca cggtcaaaca atcgaccatc ggtaagtaca acgagaaata cggtgacgca   1680
tccggtaact acgttttcat ccgtgcccac gataacaacg tccagacat catcgccgag   1740
atcatcaaga aagagatcaa cccgaaaagc gacggcttca ccatcaccga cgccgaaatg   1800
aagcaagcct tgaaatcta acaaagat atgctgtcga gcgacaaaaa gtataccctg     1860
aataacattc cggcagcgta tgccgtgatg ttgcagaata tggaaacgat taccccgcgtc   1920
tattacggta atctgtatac ggacgacggt cactacatgg aaaccaaatc tccgtattac   1980
gataccatcg tgaatttgat gaagagccgt atcaagtatg tttcgggtgg ccaggcgcaa   2040
cgtagctatt ggctgccgac cgacggtaag atggacaata gcgacgttga gctgtaccgc   2100
acgaatgagg tttacacgag cgtgcgctat ggtaaggata tcatgaccgc taatgatacc   2160
gaaggctcta gtattcccg caccagcggc caagtcacct tggtcgcgaa caatcccgaag   2220
ctgaatctgg accaaagcgc caagttgaat gtggagatgg gcaaaatcca tgcgaatcag   2280
aagtatcgcg cactgattgt cggcactgcg gacggcatta gaactttac ttccgacgcg   2340
gacgccattg cagcgggtta tgtgaaagaa accgatagca acggcgtgct gaccttcggt   2400
gctaacgaca ttaagggcta cgaaacgttt gatatgagcg gtttcgtggc ggtgtgggtt   2460
ccggtgggtg catctgcaa tcaggacatt cgtgttgcgc cgagcaccga ggcaaagaaa   2520
gaaggtgagc tgaccttgaa ggcgacggaa gcgtatgata gccagctgat ttacgaaggc   2580
tttagcaatt tccagacgat cccagatggc agcgatccgt ccgtgtatac gaaccgcaag   2640
attgcggaga acgtggatct gttcaaaagc tggggtgtca ccagctttga gatggcaccg   2700
caatttgtct cggcggatga tggcacctt ctggatagcg ttattcagaa tggctacgcc   2760
ttcgccgacc gttatgacct ggccatgtcc aagaacaaca agtatggtag caaagaggac   2820
ctgcgtgatg cactgaaagc actgcataag gcgggtattc aagctatcgc agactgggtt   2880
ccagaccaga tctaccagct gccgggcaaa gaagttgtca ccgccacccg tacggatggt   2940
gctgccgta agatcgcaga cgcgattatc gaccattctc tgtatgttgc aaacagcaaa   3000
agcagcggca agattatca gcaaagtac ggtggcgagt tcctggccga gctgaaagcc   3060
aaatacccgg aaatgttcaa agttaacatg attagcacgg gtaagccgat tgatgactcc   3120
gtgaaattga agcaatggaa agccgagtac ttcaatggca ccaacgtttt ggaacgtggt   3180
gtcggctatg ttctgagcga cgaggcgacc ggtaagtatt cacaaagaagc aattcattc   3240
aatttcattc cgctgcaact gacgggtaaa gagaaagtta tcacgggttt ctccagcgat   3300
ggtaagggta tcacctattt cggtacgagc ggtacgcagg cgaagtctgc gtttgttacc   3360
ttcaatggta acacctacta tttcgacgcg cgtgccaca tggttaccaa tagcgaatac   3420
agcccgaatg gcaaggacgt ctaccgtttt ctgccgaacg gtatcatgct gagcaatgcg   3480
ttttacattg atgcgaacgg taataccac ctgtacaact ctaagggtca aatgtacaaa   3540
ggcggttaca cgaaattcga tgtttctgaa acggataagg acggtaaaga gtccaaggtc   3600
gtcaagttcc gctactttac gaacgaaggc gtcatggcca agggtgttac cgtcattgat   3660
ggttttaccc aatacttcgg tgaggacggc tttcaagcga aggataagct ggtcaccttc   3720
aagggcaaga cgtattactt cgacgcacac actggtaatg gtatcaaaga tacctgcgc   3780
aatatcaatg gtaaatggta ctatttcgac gcgaatggcg ttgctgcgac cggtgcgcag   3840
gtgattaacg ccagaaact gtacttcaac gaggatggct cccaagtcaa aggcggcgtg   3900
gttaagaacg cagacggcac ctatagacaa tacaaagaag gttttggtga gctggttact   3960
aacgagtttt tcacgactga tggcaatgtt tggtactacg ccggtgcaaa tggtaaaacc   4020
gttaccggtg cacaagtgat caacggccaa catttgtact tcaatgcgga cggttcccag   4080
gtgaagggtg gcgttgtcaa gaacgcggat ggcacctaca gcaagtacaa tgctagcact   4140
ggtgaacgtc tgacgaacga gttcttacg accggtgata caattggta ttcattggc   4200
gcaaacggta agagcgtgac gggtgaggtc aagattgata ctacttta ctttttcgtg   4260
aaggatggca aacaagttaa aggtcaaacc gtcagcgccg taatggtcg cattagctac   4320
tactacggtg acagcggcaa gcgtgcggtt agcacctgga ttgagattca gccgggtgtt   4380
tatgtgtatt tcgacaaaaa cggtttggcg tacccctccgc gtgttctgaa ttaa       4434
```

SEQ ID NO: 8        moltype = AA   length = 1477
FEATURE             Location/Qualifiers
source              1..1477
                    mol_type = protein
                    organism = Streptococcus salivarius
SEQUENCE: 8
```
MDETQDKTVT QSNSGTTASL VTSPEATKEA DKRTNTKEAD VLTPAKETNA VETATTTNTQ    60
ATAEAATTAT TADVAVAAVP NKEAVVTTDA PAVTTEKAEE QPATVKAEVV NTEVKAPEAA   120
LKDSEVEAAL SLKNIKNIDG KYYYVNEDGS HKENFAITVN GQLLYFGKDG ALTSSSTYSF   180
TPGTTNIVDG FSINNRAYDS SEASFELIDG YLTADSWYRP ASIIKDGVTW QASTAEDFRP   240
LLMAWWPNVD TQVNYLNYMS KVFNLDAKYS STDKQETLKV AAKDIQIKIE QKIQAEKSTQ   300
```

```
WLRETISAFV KTQPQWNKET ENYSKGGGED HLQGGALLYV NDSRTPWANS DYRRLNRTAT    360
NQTGTIDKSI LDEQSDPNHM GGFDFLLAND VDLSNPVVQA EQLNQIHYLM NWGSIVMGDK    420
DANFDGIRVD AVDNVDADML QLYTNYFREY YGVNKSEANA LAHISVLEAW SLNDNHYNDK    480
TDGAALAMEN KQRLALLFSL AKPIKERTPA VSPLYNNTFN TTQRDEKTDW INKDGSKAYN    540
EDGTVKQSTI GKYNEKYGDA SGNYVFIRAH DNNVQDIIAE IIKKEINPKS DGFTITDAEM    600
KQAFEIYNKD MLSSDKKYTL NNIPAAYAVM LQNMETITRV YYGDLYTDDG HYMETKSPYY    660
DTIVNLMKSR IKYVSGGQAQ RSYWLPTDGK MDNSDVELYR TNEVYTSVRY GKDIMTANDT    720
EGSKYSRTSG QVTLVANNPK LNLDQSAKLN VEMGKIHANQ KYRALIVGTA DGIKNFTSDA    780
DAIAAGYVKE TDSNGVLTFG ANDIKGYETF DMSGFVAVWV PVGASDNQDI RVAPSTEAKK    840
EGELTLKATE AYDSQLIYEG FSNFQTIPDG SDPSVYTNRK IAENVDLFKS WGVTSFEMAP    900
QFVSADDGTF LDSVIQNGYA FADRYDLAMS KNNKYGSKED LRDALKALHK AGIQAIADWV    960
PDQIYQLPGK EVVTATRTDG AGRKIADAII DHSLYVANSK SSGKDYQAKY GGEFLAELKA   1020
KYPEMFKVNM ISTGKPIDDS VKLKQWKAEY FNGTNVLERG VGYVLSDEAT GKYFTVTKEG   1080
NFIPLQLTGK EKVITGFSSD GKGITYFGTS GTQAKSAFVT FNGNTYYFDA RGHMVTNSEY   1140
SPNGKDVYRF LPNGIMLSNA FYIDANGNTY LYNSKGQMYK GGYTKFDVSE TDKDGKESKV   1200
VKFRYFTNEG VMAKGVTVID GFTQYFGEDG FQAKDKLVTF KGKTYYFDAH TGNGIKDTWR   1260
NINGKWYYFD ANGVAATGAQ VINGQKLYFN EDGSQVKGGV VKNADGTYSK YKEGFGELVT   1320
NEFFTTDGNV WYYAGANGKT VTGAQVINGQ HLYFNADGSQ VKGGVVKNAD GTYSKYNAST   1380
GERLTNEFFT TGDNNWYYIG ANGKSVTGEV KIGDDTYFFA KDGKQVKGQT VSAGNGRISY   1440
YYGDSGKRAV STWIEIQPGV YVYFDKNGLA YPPRVLN                            1477

SEQ ID NO: 9            moltype = DNA   length = 4311
FEATURE                 Location/Qualifiers
source                  1..4311
                        mol_type = other DNA
                        organism = Streptococcus downei
SEQUENCE: 9
atggttgacg gcaaatacta ctactacgat caggacggca acgtaaagaa aaacttcgcg     60
gttagcgtgg gcgagaaaat ctattacttt gacgaaactg gcgcctacaa agacaccagc    120
aaagttgagg cggacaaaag cggcagcgac attagcaagg aagagactac cttcgcggca    180
aacaaccgcg cctacagcac cagcgcggag aattttgagg cgatcgacaa ttatctgacc    240
gcggactcct ggtatcgtcc taaatccatc ctgaaggatg caaaacgtg acggaaagc     300
agcaaagatg actttcgtcc gctgctgatg cgtggtggc cggataccga aacgaagcgc    360
aattacgtga actacatgaa caaagttgtt ggcatcgaca agacctatac cgcgaaacc    420
agccaggccg acttgaccgc tgcggcggaa ctggtgcaag cacgcattga gcagaagatc    480
acgaccgaac agaacacgaa atggctgcgt gaggcaatct cggcatttgt aaaacgcaa    540
ccgcagtgga acggtgaaag cgagaagccg tacgacgatc acctgcaaaa cggtgctctg    600
aaatttgata atcagagcga cctgaccccg gatacgcaaa gcaactaccg tctgttgaac    660
cgtacccccga ctaatcagac gggtacgctg gacagccgct tcacttataa ccgcaacgac    720
cctttgggcg gttatgagct gctgctggca aatgacgtcg ataacagcaa tccgatcgtg    780
caggcggagc agctgaactg gctgcattac ctgctgaatt tggtacgat ctacgccaaa     840
gatgccgacg ctaacttcga tagcattcgt gtggacgcgg ttgataacgt cgatgcggat    900
ctgctgcaaa ttagcagcga ttacctgaaa gcagcgact gcattgataa gaataacaaa    960
aacgcgaaca accacgtgag cattgtcgaa gcctggagcg ataatgatac cccgtacctg   1020
catgacgatg tgacaaacct gatgaatatg ataacaaat tcgcctgtc catgctgtgg     1080
tcgctggcca accgctgga caagcgtagc ggtctgaacc cgctgattca taacagcttg   1140
gtggatcgtg aagttgatga ccgcgaggtt gaaacgggttc cgagctattc ttttgcacgt   1200
gcgcatgata gcgaggtcca ggacttgatc cgtgacatca tcaaggcaga gatcaatccg   1260
aacgcattcg gttatagctt tacccaagac gagattgacc aggcctttaa gatttacaat   1320
gaggatctga agaaaacgga taagaaatac cccactata atgtgccgtt gagctacacc   1380
ctgctgctga cgaataaggg tagcatccca cgtgtctact atggtgatat gtttaccgac   1440
gatggtcagt atatggcgaa caaaaccgtc aactatacg ccattgaatc tctgctgaaa    1500
gcgcgtatga agtatgtcgc tggcggtcaa gcaatgcaga actaccaaat cggtaatggt   1560
gagatcctga ccagcgttcg ttatggtaag ggtgccctga acagagcga caaaggtgat   1620
gcgaccacgc gcaccagcgg cagtcggtgtc gttatgggca atcagccaac ctttagcttg   1680
gacggcaaag tggtggctct gaacatgggc gcagctcatg cgaatcagga gtatcgtgcg   1740
ctgatggtta gcacgaaaga cggtgttgcc acgtatgcga ccgatgcaga tgcgagcaaa    1800
gccggtctgt caaacgtac cgacgaaaac ggctacctgt atttcctgaa tgacgacctg    1860
aagggtgtgg ccaatcctca ggtgagcggt ttcttgcagg tgtgggttcc ggtgggtgcc   1920
gcggatgatc aagatatccg tgttgcagct agcgatacgg catccaccga tggcaagagc   1980
ctgcaccaag acgccgcgat ggatagccgt gttatgcctg aaggcttctc taacttcag    2040
tcctttgcca cgaaagaaga ggaatatacc aacgtcgtta tcgccaacaa tgtggataag   2100
ttcgttagct ggggtatcac ggatttcgag atggccccac aatatgttc cagcaccgac    2160
ggtcaattcc tggactctgt cattcagaac ggttatgctt ttacggaccg ttatgacttg    2220
ggcatgtcta aggcaaacaa atcggcacg gccgatcaac tggtaaggc cattaaggcc    2280
ctgcacgcga agggcctgaa ggtatggca gattgggtgc cggatcagat gtataccttc    2340
ccgaaacagg aagtcgtgac cgttacccgt accgacaaat ttggcaaacc gatcgcaggt    2400
tcccaaatca atcatagcct gtatgttacc gataccaagt ccaacggcga tgactatcag    2460
gccaaatatg tggtggcgtt tctggacgag ctgaaggaga aaatccgga gctgttcacg    2520
aagaaacaaa tcagcacggg tcaagctatt gacccgagcg tgaaaatcaa acagtggtct    2580
gctaagtatt tcaatggctc caacatcctg ggtcgcggtg cggactacgt actgtcggat    2640
caggcgagca caaatacct gaacgtgtct gacgataaac tgttcctgcc gaaaaccttg    2700
ctgggccaag ttgtcgagag cggtatccgc tttgacggca ctggttatgt gtacaactct    2760
agcactacgg gtgaaaagt taccgattcc ttcattacgg aggcagtaa tctgtactac     2820
ttcggtcaag acggctatat ggtgaccggc gcacagaaca ttaagggcag caactactac    2880
ttcctggcca atggtgcggc cctgcgtaac accgtttaca ccgatgcgca aggtcagaat    2940
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt tcgataaaga tggtgtccag gccaaggata agatcattgt cacccgcgat    3120
```

-continued

```
ggcaaagtcc gctatttcga ccagcacaac ggtaatgcgg ttactaacac gttcgttgcg   3180
gacaagacgg gtcactggta ctatctgggc aaagacggcg tcgcggttac cggtgcgcag   3240
actgtgggta acagcatttt gtactttgaa gcgaacggtc aacaagtcaa gggtgacttc   3300
gtgacggcta agacggtaa actgtacttc tatgatgtgg acagcggcga catgtggacc   3360
aataccttta tcgaggataa agcgggtaat tggttctacc tgggtaagga cggtgcggcc   3420
gtcaccggtg cacagacgat caaaggccag aaattgtatt tcaaagccaa cggtcagcaa   3480
gttaaaggtg acattgtcaa ggacgcggac ggtaagatcc gttattacga cgctcagacc   3540
ggtgaacagg tctttaacaa gtccgttagc gtcaacggta agacctacta tttcggtagc   3600
gacggcaccg cgcaaaccca ggcgaatccg aaaggccaaa cctttaagga tggtagcggc   3660
gttctgcgtt tctacaattt ggagggccag tatgtctcgg gcagcggctg gtacgaaacg   3720
gccgagcacg agtgggtata tgtgaaatcc ggtaaagttc tgaccggtgc ccagacgatt   3780
ggtaatcaac gtgtttactt caaggacaat ggtcaccagg tgaaaggcca gctggtcacg   3840
ggtaatgacg gtaaattgcg ttactacgac gcgaacagcg gtgatcaagc attcaacaaa   3900
tccgtcacgg ttaacggtaa aacctactac tttggcagcg atggtacggc cgcagcgcag   3960
gctaatccta agggtcagac cttcaaagat ggtagcggcg tgctgcgttt ttacaacttg   4020
gaaggccaat acgtgtctgg cagcggttgg tacaagaatg cgcagggcca gtggctgtac   4080
gtgaaagatg gcaaggtcct gaccggtctg caaacggtcg gcaatcagaa ggtctacttc   4140
gacaaaaatg gcatccaagc aaagggtaag gccgttcgca cgtccgatgg taaagtgcgc   4200
tactttgatg agaatagcgg tagcatgatt acgaaccaat ggaagttcgt ttacggtcaa   4260
tactattact tcggttctga cggcgcagcg gtttaccgtg gttggaacta a           4311
```

SEQ ID NO: 10        moltype = AA   length = 1436
FEATURE                  Location/Qualifiers
source                   1..1436
                         mol_type = protein
                         organism = Streptococcus downei
SEQUENCE: 10

```
MVDGKYYYYD QDGNVKKNFA VSVGEKIYYF DETGAYKDTS KVEADKSGSD ISKEETTFAA   60
NNRAYSTSAE NFEAIDNYLT ADSWYRPKSI LKDGKTWTES SKDDFRPLLM AWWPDTETKR   120
NYVNYMNKVV GIDKTYTAET SQADLTAAAE LVQARIEQKI TTEQNTKWLR EAISAFVKTQ   180
PQWNGESEKP YDDHLQNGAL KFDNQSDLTP DTQSNYRLLN RTPTNQTGSL DSRFTYNAND   240
PLGGYELLLA NDVDNSNPIV QAEQLNWLHY LLNFGTIYAK DADANFDSIR VDAVDNVDAD   300
LLQISSDYLK AAYGIDKNNK NANNHVSIVE AWSDNDTPYL HDDGDNLMNM DNKFRLSMLW   360
SLAKPLDKRS GLNPLIHNSL VDREVDDREV ETVPSYSFAR AHDSEVQDLI RDIIKAEINP   420
NAFGYSFTQD EIDQAFKIYN EDLKKTDKKY THYNVPLSYT LLLTNKGSIP RVYYGDMFTD   480
DGQYMANKTV NYDAIESLLK ARMKYVAGGQ AMQNYQIGNG EILTSVRYGK GALKQSDKGD   540
ATTRTSGVGV VMGNQPNFSL DGKVVALNMG AAHANQEYRA LMVSTKDGVA TYATDADASK   600
AGLVKRTDEN GYLYFLNDDL KGVANPQVSG FLQVWVPVGA ADDQDIRVAA SDTASTDGKS   660
LHQDAAMDSR VMFEGFSNFQ SFATKEEEYT NVVIANNVDK FVSWGITDFE MAPQYVSSTD   720
GQFLDSVIQN GYAFTDRYDL GMSKANKYGT ADQLVKAIKA LHAKGLKVMA DWVPDQMYTF   780
PKQEVVTVTR TDKFGKPIAG SQINHSLYVT DTKSSGDDYQ AKYGGAFLDE LKEKYPELFT   840
KKQISTGQAI DPSVKIKQWS AKYFNGSNIL GRGADYVLSD QASNKYLNVS DDKLFLPKTL   900
LGQVVESGIR FDGTGYVYNS STTGEKVTDS FITEAGNLYY FGDGYMVTG AQNIKGSNYY   960
FLANGAALRN TVYTDAQGQN HYYGNDKRY ENGYQQFGND SWRYFKNGVM ALGLTTVDGH   1020
VQYFDKDGVQ AKDKIIVTRD GKVRYFDQHN GNAVTNTFVA DKTGHWYYLG KDGVAVTGAQ   1080
TVGKQHLYFE ANGQQVKGDF VTAKDGKLYF YDVDSGDMWT NTFIEDKAGN WFYLGKDGAA   1140
VTGAQTIKGQ KLYFKANGQQ VKGDIVKDAD GKIRYYDAQT GEQVFNKSVS VNGKTYYFGS   1200
DGTAQTQANP KGQTFKDSGS VLRFYNLEGQ YVSGSGWYET AEHEWVYVKS GKVLTGAQTI   1260
GNQRVYFKDN GHQVKGQLVT GNDGKLRYYD ANSGDQAFNK SVTVNGKTYY FGSDGTAQTQ   1320
ANPKGQTFKD SGSVLRFYNL EGQYVSGSGW YKNAQGQWLY VKDGKVLTGL QTVGNQKVYF   1380
DKNGIQAKGK AVRTSDGKVR YFDENSGSMI TNQWKFVYGQ YYYFGSDGAA VYRGWN       1436
```

SEQ ID NO: 11        moltype = DNA   length = 3942
FEATURE                  Location/Qualifiers
source                   1..3942
                         mol_type = other DNA
                         organism = Streptococcus mutans
SEQUENCE: 11

```
atgattgacg gcaaatacta ctactatgac aacaacggca aagtacgcac caatttcacg   60
ttgatcgcgg acggtaaaat cctgcatttt gatgaaactg gcgcgtacac cgacactagc   120
attgataccg tgaacaagga tattgtcacg acgcgtagca acctgtataa gaatacaatt   180
caagtgtatg atcgcagcgc gcagagcttc gagcatgttg atcactacct gacggcggaa   240
tcttggtacc gtccgaaata cattctgaaa gatggcaaga cctggaccca gagcaccgag   300
aaggacttcc gtcctctgct gatgacctgg tggccgagca gggaaacgca cgaacagatt   360
gtcaacttca tgaacgccca gttgggtatc aacaaaacgt acgacgacac cagcaatcag   420
ctgcaattga acatcgctgc tgcaacgatc aagcaaaga tcgaagccaa aatcacgacg   480
ctgaagaaca ccgattggct gcgtcaaacg atcagcgcgt cgtcaaaac ccaaagcgct   540
tggaatagcg acagcgaaaa gccgtttgat gaccatctgc aaaacggtgc ggttctgtat   600
gataacgaag gtaaattgac gccgtatgcc aatagcaact atcgtattct gaaccgcacg   660
ccgaccaacc agaccggtaa gaaggacccg cgttataccc cgacaacac gatcggcggc   720
tacgagtttc gctgccaa cgacgtggat aatagcaacc cggtggttca ggccgagcag   780
ctgaactggc tgcacttcct gatgaactt ggtaatatct acgcaaacga ccctgacgct   840
aacttcgact ccatccgcgt tgacgctgtc gataatgtgg acgccgatct gttacagatc   900
gcgggtgact tctgtgaaag gcaaagggc atccataaa atgacaacga gcgaacgaa   960
cacctgtcca ttctggaagc gtggagcgac aatgacactc cgtatctgca tgatgatggc   1020
gacaacatga ttaacatgga taacaaactg cgcctgagcc tgctgttctc cctggcgaaa   1080
ccgctgaatc agcgtagcgg tatgaacccg ttgattacga acagcctggt caaccgtact   1140
gatgataatg ccgaaacggc ggcagtgcca agctactctt ttatccgtgc ccacgatagc   1200
gaggtccagg atttgattcg tgatatcatt aaggctgaga ttaaccccgaa cgtcgtcggt   1260
```

```
tacagcttca cgatggaaga gattaagaag gcatttgaga tctacaataa ggacctgttg  1320
gccacggaga agaagtatac ccactataac accgcattga gctacgcgtt gctgctgacg  1380
aacaagagca gcgtgccgcg tgtctactat ggtgatatgt ttacggacga tggtcaatac  1440
atggcccaca agaccattaa ctacgaggca atcgaaaccc tgctgaaagc acgtatcaag  1500
tacgtgtccg gtggtcaggc tatgcgcaac cagcaagtcg gtaattcgga gatcatcacc  1560
agcgtgcgtt acggtaaagg tgcgctgaag gcgatggata cgggtgaccg cactacccgt  1620
acctctggtg tggcggtcat tgagggcaac aacccgagct tgcgcctgaa ggcttctgat  1680
cgtgtggttg tgaatatggg tgcggcccac aaaaatcaag cctatcgccc gctgctgttg  1740
acgaccgata acggcattaa ggcctatcac agcgaccaag ccgaggcagg cctggtgcgc  1800
tacaccaacg accgtggcga actgatcttt accgcagccg acattaaggg ctacgcaaat  1860
ccgcaagtta gcggctacct gggcgtctgg gtccctgttg gcgcagcagc tgatcaggac  1920
gttcgtgttg cggcgagcac cgcgccaagc acggacggca agagcgttca ccagaacgcg  1980
gctctggaca gccgtgtgat gttcgagggt ttctcgaact tccaggcatt tgctaccaag  2040
aaagaagat ataccaatgt ggtcatcgct aagaatgtgg ataagttcgc ggagtggggt  2100
gtcaccgatt tcgagatggc tccgcaatac gtttctagca ccgacggtag cttttttggat  2160
agcgtgattc aaaacggtta tgcttttacc gaccgttacg acctgggcat cagcaagccg  2220
aacaaatatg gcaccgcgga cgatctggtt aaagcgatta ggcattgca cagcaaaggc  2280
atcaaagtta tggcggattg ggttccggac cagatgtatg ccctgccgga aaaagaggtt  2340
gtgacggcaa cccgtgttga caaatacggt acgccggtag ctggcagcca gatcaaaaac  2400
acgctgtacg tggtcgatgg taaatctagc ggtaaggacc agcaggcgaa gtacggtggt  2460
gccttcctgg aagagctgca agcgaagtat ccggaactgt tcgcgcgcaa acagattagc  2520
accggtgttc cgatggaccc gagcgtcaag attaagcaat gggcgcaaa atacttcaac  2580
ggcacgaata tcctgggtcg tggtgctggt tacgtgctga agatcaggc aaccaacacc  2640
tactttaaca tcagcgacaa taagagatc aatttcctgc caaagacgtt gctgaaccag  2700
gattctcaag ttggctttag ctacgacggt aagggctatg tgtactacag cacctcgggc  2760
taccaggcta aaaacacgtt catcagcgag ggtgacaagt ggtattactt cgacaataac  2820
ggttatatgg ttaccggcgc acagagcatt aatggtgtga actattactt cctgccgaat  2880
ggtttacagc tgcgtgatgc gattctgaaa atgaggacg tacgtacgc gtattatggc  2940
aatgatggtc gccgctacga gaatggctat tatcagttta tgagcggtgt ttggcgccat  3000
ttcaataatg gcgagatgtc cgttggtctg accgtcattg accgttcaagt tcaatacttt  3060
gacgagatgg gttaccaggc gaaaggcaaa ttcgttacca ccgcggatgg taagatccgt  3120
tacttcgata gcagagcgg caatatgtat cgtaatcgtt tcattgagaa cgaagagggc  3180
aaatggctgt acctgggtga ggacggcgcg gcagtcaccg tagccagac gatcaatggt  3240
cagcacctgt attttcgtgc taacggcgtt caggttaagg gtgagttcgt gaccgatcgt  3300
catggccgca tctcttatta cgacggcaac agcggtgatc agatccgcaa ccgtttcgtc  3360
cgcaatgcgc aaggccagtg gttttacttt gacaacaatg gctatgcagt aactggtgct  3420
cgtacgatca acggccagca cctgtatttc cgcgcgaacg gtgttcaggt aaaaggtgag  3480
tttgttacgg accgccacgg ccgcattagc tattatgatg gtaatagcgg tgaccaaatt  3540
cgcaatcgtt tcgtgcgtaa tgcacaggt cagtggttcc acttcgacaa taatggttat  3600
gcagtcacgg gtgcacgtac cattaacggc caacaccgt actttcgcgc caatggtgtg  3660
caagtgaaag cgaatttgt tactgatcgt tatggtcgta tcagctacta tgatggcaat  3720
tctggcgacc aaattcgcaa tcgctttgtt cgtaacgccc aaggtcaatg gttctatttc  3780
gacaacaacg gttacgcggt gaccgctgcc cgcacgatta atggtcaaca cttgtacttc  3840
cgtgccaacg gtgtccaggt gaagggtgaa tttgtgaccg accgctatgg tcgcatttct  3900
tactacgacg caaattccgg tgaacgcgtc cgtatcaatt aa  3942
```

```
SEQ ID NO: 12         moltype = AA   length = 1313
FEATURE               Location/Qualifiers
source                1..1313
                      mol_type = protein
                      organism = Streptococcus mutans
SEQUENCE: 12
MIDGKYYYD  NNGKVRTNFT  LIADGKILHF  DETGAYTDTS  IDTVNKDIVT  TRSNLYKKYN   60
QVYDRSAQSF  EHVDHYLTAE  SWYRPKYILK  DGKTWTQSTE  KDFRPLLMTW  WPSQETQRQY  120
VNFMNAQLGI  NKTYDDTSNQ  LQLNIAAATI  QAKIEAKITT  LKNTDWLRQT  ISAFVKTQSA  180
WNSDSEKPFD  DHLQNGAVLY  DNEGKLTPYA  NSNYRILNRT  PTNQTGKKDP  RYTADNTIGG  240
YEFLLANDVD  NSNPVVQAEQ  LNWLHFLMNF  GNIYANDPDA  NFDSIRVDAV  DNVDADLLQI  300
AGDYLKAAKG  IHKNDKAAND  HLSILEAWSD  NDTPYLHDDG  DNMINMDNKL  RLSLLFSLAK  360
PLNQRSGMNP  LITNSLVNRT  DDNAETAAVP  SYSFIRAHDS  EVQDLIRDII  KAEINPNVVG  420
YSFTMEEIKK  AFEIYNKDLL  ATEKKYTHYN  TALSYALLLT  NKSSVPRVYY  GDMFTDDGQY  480
MAHKTINYEA  IETLLKARIK  YVSGGQAMRN  QQVGNSEIIT  SVRYGKGALK  AMDTGDRTTR  540
TSGVAVIEGN  NPSLRLKASD  RVVVNMGAAH  KNQAYRPLLL  TTDNGIKAYH  SDQEAAGLVR  600
YTNDRGELIF  TAADIKGYAN  PQVSGYLGVW  VPVGAAADQD  VRVAASTAPS  TDGKSVHQNA  660
ALDSRVMFEG  FSNFQAFATK  KEEYTNVVIA  KNVDKFAEWG  VTDFEMAPQY  VSSTDGSFLD  720
SVIQNGYAFT  DRYDLGISKP  NKYGTADDLV  KAIKALHSKG  IKVMADWVPD  QMYALPEKEV  780
VTATRVDKYG  TPVAGSQIKN  TLYVVDGKSS  GKDQQAKYGG  AFLEELQAKY  PELFARKQIS  840
TGVPMDPSVK  IKQWSAKYFN  GTNILGRGAG  YVLKDQATNT  YFNISDNKEI  NFLPKTLLNQ  900
DSQVGFSYDG  KGYVYYSTSG  YQAKNTFISE  GDKWYYFDNN  GYMVTGAQSI  NGVNYYFLPN  960
GLQLRDAILK  NEDGTYAYYG  NDGRRYENGY  YQFMSGVWRH  FNNGEMSVGL  TVIDGQVQYF 1020
DEMGYQAKGK  FVTTADGKIR  YFDKQSGNMY  RNRFIENEEG  KWLYLGEDGA  AVTGSQTING 1080
QHLYFRANGV  QVKGEFVTDR  HGRISYYDGN  SGDQIRNRFV  RNAQGWFYF  DNNGYAVTGA 1140
RTINGQHLYF  RANGVQVKGE  FVTDRHGRIS  YYDGNSGDQI  RNRFVRNAQG  QWFYFDNNGY 1200
AVTGARTING  QHLYFRANGV  QVKGEFVTDR  YGRISYYDGN  SGDQIRNRFV  RNAQGQWFYF 1260
DNNGYAVTGA  RTINGQHLYF  RANGVQVKGE  FVTDRYGRIS  YYDANSGERV  RIN        1313

SEQ ID NO: 13         moltype = DNA   length = 3972
FEATURE               Location/Qualifiers
source                1..3972
                      mol_type = other DNA
```

```
                     organism = Streptococcus dentirousetti
SEQUENCE: 13
atggttgacg gcaaatacta ctactacgat gcagacggca acgtaaagaa aaacttcgcg    60
gttagcgttg gcgatgccat tttctatttt gatgaaacgg gtgcctacaa agataccagc   120
aaagttgatg cggataagac cagctctagc gtcaatcaga ccacggaaac gttcgcagcg   180
aataaccgtg cgtatagcac cgcagccgag aactttgaag cgattgataa ctacctgact   240
gcggatagct ggtatcgtcc gaagtctatc ttgaaagatg gtacgacgtg gaccgaaagc   300
accaaggatg attttcgccc gctgctgatg gcgtggtggc cggataccga accaaacgt    360
aactacgtga actatatgaa caaggtggtc ggtatcgaca aaacgtacac cgccgaaacg   420
tcccaagctg acctgacggc ggcagccgaa ctggtgcagg cgcgtatcga gcagaaaatc   480
actagcgaaa agaatacgaa gtggctgcgt gaggcgattt ccgcgttcgt taagactcaa   540
ccgcagtgga atggcgagag cgagaaacct tatgatgacc acctgcaaaa tggtgcgctg   600
aagttcgaca atgaaaccag cctgaccccg gatacgcaga gcggctatcg catcctgaac   660
cgtaccccga cgaatcaaac cggtcagcct gacccgcgta tcacctttaa tcagaatgac   720
ccgctgggtg gttatgagta tttgctggct aatgatgtcg ataacagcaa cccggtcgtt   780
caggccgaga gcctgaactg gctgcattac ctgctgaatt tggtagcatt tacgcgaat   840
gatccggagg ccaatttcga cagcatccgt gtggacgcgg tggacaatgt tgacgcagac   900
ctgctgcaaa ttagctcgga ttacctgaaa tcggcgtaca aaattgacaa gaacaacaaa   960
aatgcgaacg accacgttag catcgtcgag gcgtggagcg acaatgatac cccgtacctg  1020
aatgatgatg gcgacaatct gatgaacatg gataacaagt ttcgtctgag catgctgtgg  1080
agcctggcga agccaaccaa tgtccgtagc ggcttgaatc cgctgatcca acacagcgtg  1140
gttgaccgtg aggtggacga ccgtgaagtt gaggctaccc cgaattacag ctttgcacgt  1200
gcacacgaca gcgaagttca agatttgatt cgcgacatca tcaaagctga gatcaaccca  1260
aacagcttcg gttatagctt taccaagag gaaatcgacc aggccttcaa gatctacaat  1320
gaggatttga agaaaaccaa taagaagtat acccactaca acgtcccgct gagctacacc  1380
ctgctgctga cgaacaaggg cagcattcca cgcatttact acggtgacat gtttacggat  1440
gacggtcagt atatggccaa caaaaccgtt aactatacg ccattgagag cctgctgaaa  1500
gcacgtatga agtatgttag cggtggccaa gcgatgcaga attacaacat cggcaacggc  1560
gagattctga ccagcgtccg ttacggtaag ggtgccctga acagagcga caaaggcgat  1620
aagactactc gtaccagcgg tattggcgtt gtgatgggta accagacgaa tttcagcctg  1680
gagggcaagg tggtggccct gaatatgggg gcaacgcata ccaaacagaa gtatcgtgca  1740
ttgatggtgt ctacggaaac cggcgtggcg atttacaata gcgatgaaga agcagaggca  1800
gcaggcctga tcaaaacgac cgatgagaat ggttatttgt acttctgaa tgacgatctg  1860
aagggcgtgg ctaacccgca ggtcagcggc ttcctgcaaa tgtgggttcc ggttggtgca  1920
ccggctgacc aggacattcg tgtggcggcg accgatgcag cttctaccga cggtaagagc  1980
ctgcatcagg acgcagctct ggattctcgc gtcatgtttg aaggtttcag caacttccag  2040
agcttcgcaa ccaaggaaga ggaatacacc aacgttgtta ttgcaaagaa cgtggataag  2100
ttcgtgagct ggggtatcac cgacttcgag atggcaccgc agtacgttag ctctaccgat  2160
ggcaccttc tggatagcgt gattcaaaat ggctatgcct ttacggaccg ttacgacctg  2220
ggtatgagca aagcaaacaa gtatggtact gctgaccaac tggtggccgc gattaaagcc  2280
ctgcatgcga agggtctgcg tgtgatggcg gattgggtcc cagatcaaat gtacactttc  2340
cctaagaagg aagtggttac cgttacccgt acggacaaat ttggcaatcc agtggcaggc  2400
agccaaatca accacacctt gtacgtcact gatactaagg ttgacggtga cgactaccag  2460
gcgaagtacg gtggcgcatt cctggatgaa ctgaaagaaa agtacccgga gctgtttacc  2520
aagaagcaaa tcagcaccgg tcaggcaatc gacccgagcg tgaaaatcaa gcagtggagc  2580
gcgaagtact tcaacggtag caatatcttg ggtcgcggtg cgaactacgt gctgtccgac  2640
caggcgtcta acaagtactt taacgtgcc gaaggtaagg tcttctgcc agcggcgtgg  2700
ctgggtaagg tcgtcgagag cggtatccgt ttcgacggta aaggttatat ctataacagc  2760
agcaccactg gcgaacaagt gaaggacagc ttcattaccg aagcgggtaa cttgtactat  2820
tttggcaaag atggttatat ggtcatgggt gcacagaata tccagggtgc taactactac  2880
ttcttggcga atggtgcggc cctgcgcaat agcatcctga cggatcagga tggcaaaagc  2940
cactatatg caaatgacgg caagcgttat gagaacggct actatcaatt cggtaacgac  3000
tcctggcgct attttgaaaa cggcgttatg gccgttggtt tgacgcgcgt tgcgggccac  3060
gaccaatact ttgataagga tggtatccaa gcgaagaata agatcattgt tacgcgtgac  3120
ggtaaggtcc gctacttcga cgaacacaac ggcaatgctc ccacgaatac gtttatcagc  3180
gatcaagccg gccattggta ctacctgggt aaagatggtg tcgccgtgac gggtgcgcag  3240
accgttggca agcaacacct gtacttgag gctaacggcc aacaagtaaa aggcgatttt  3300
gttaccgcca aggacggtaa gttgtatttt ctggacggtg actctggcga catgtggacc  3360
gatccttcg tccaggataa ggctggtcat tggttctatc tgggcaaaga cggtgcggcg  3420
gtaaccggtg cccagaccgt ccgtggtcag aagctgtact tcaaagcgaa tggccagcag  3480
gttaagggtg acattgtgaa aggcgcggat ggtaaaatcc gttactatga tgcaaattcc  3540
ggtgaccagg tttacaatcg cacggtgaaa ggctccgacg gcaagaccta tcattggt   3600
aatgacggcg tcgcaatcac gcaaaccatc gccaaggcc agaccatcaa ggatggcagc  3660
gttctgcgct tctatagcat ggagggtcag ctggtgaccg gcggctg gtattcgaac  3720
gcgaaaggtc aatggttgta tgtcaagaac ggtcaagtcc tgacgggttt cgcagacggtg  3780
ggcagcagc gtgtgtactt tgacgcaaat ggtattcaag cgaaaggtaa agcagtgcgt  3840
acctccgatg caaactgcg ttacttcgat gcgaacagcg gcagcatgat caccaatcag  3900
tggaaagaag ttaatggtca gtactactat ttcgacaaca acggtgttgc gatctatcgc  3960
ggttggaact aa                                                    3972

SEQ ID NO: 14        moltype = AA  length = 1323
FEATURE              Location/Qualifiers
source               1..1323
                     mol_type = protein
                     organism = Streptococcus dentirousetti
SEQUENCE: 14
MVDGKYYYD ADGNVKKNFA VSVGDAIFYF DETGAYKDTS KVDADKTSSS VNQTTETFAA    60
NNRAYSTAAE NFEAIDNYLT ADSWYRPKSI LKDGTTWTES TKDDFRPLLM AWWPDTETKR  120
NYVNYMNKVV GIDKTYTAET SQADLTAAAE LVQARIEQKI TSEKNTKWLR EAISAFVKTQ  180
```

```
PQWNGESEKP YDDHLQNGAL KFDNETSLTP DTQSGYRILN RTPTNQTGSL DPRFTFNQND    240
PLGGYEYLLA NDVDNSNPVV QAESLNWLHY LLNFGSIYAN DPEANFDSIR VDAVDNVDAD    300
LLQISSDYLK SAYKIDKNNK NANDHVSIVE AWSDNDTPYL NDDGDNLMNM DNKFRLSMLW    360
SLAKPTNVRS GLNPLIHNSV VDREVDDREV EATPNYSFAR AHDSEVQDLI RDIIKAEINP    420
NSFGYSFTQE EIDQAFKIYN EDLKKTNKKY THYNVPLSYT LLLTNKGSIP RIYYGDMFTD    480
DGQYMANKTV NYDAIESLLK ARMKYVSGGQ AMQNYNIGNG EILTSVRYGK GALKQSDKGD    540
KTTRTSGIGV VMGNQSNFSL EGKVVALNMG ATHTKQKYRA LMVSTETGVA IYNSDEEAEA    600
AGLIKTTDEN GYLYFLNDDL KGVANPQVSG FLQVWVPVGA PADQDIRVAA TDAASTDGKS    660
LHQDAALDSR VMFEGFSNFQ SFATKEEEYT NVVIAKNVDK FVSWGITDFE MAPQYVSSTD    720
GTFLDSVIQN GYAFTDRYDL GMSKANKYGT ADQLVAAIKA LHAKGLRVMA DWVPDQMYTF    780
PKKEVVTVTR TDKFGNPVAG SQINHTLYVT DTKGSGDDYQ AKYGGAFLDE LKEKYPELFT    840
KKQISTGQAI DPSVKIKQWS AKYFNGSNIL GRGANYVLSD QASNKYFNVA EGKVFLPAAM    900
LGKVVESGIR FDGKGYIYNS STTGEQVKDS FITEAGNLYY FGKDGYMVMG AQNIQGANYY    960
FLANGAALRN SILTDQDGKS HYYANDGKRY ENGYYQFGND SWRYFENGVM AVGLTRVAGH   1020
DQYFDKDGIQ AKNKIIVTRD GKVRYFDEHN GNAATNTFIS DQAGHWYYLG KDGVAVTGAQ   1080
TVGKQHLYFE ANGQQVKGDF VTAKDGKLYF LDGDSGDMWT DTFVQDKAGH WFYLGKDGAA   1140
VTGAQTVRGQ KLYFKANGQQ VKGDIVKGAD GKIRYYDANS GDQVYNRTVK GSDGKTYIIG   1200
NDGVAITQTI AKGQTIKDGS VLRFYSMEGQ LVTGSGWYSN AKGQWLYVKN GQVLTGLQTV   1260
GSQRVYFDAN GIQAKGKAVR TSDGKLRYFD ANSGSMITNQ WKEVNGQYYY FDNNGVAIYR   1320
GWN                                                                1323

SEQ ID NO: 15          moltype = DNA  length = 4047
FEATURE                Location/Qualifiers
source                 1..4047
                       mol_type = other DNA
                       organism = Streptococcus oralis
SEQUENCE: 15
atgatcgacg gcaaaaacta ctacgtacag gatgatggca cggtaaagaa gaatttcgcg     60
gtagaactga atggtcgtat cctgtatttt gatgcagaaa ccggcgctct ggttgatagc    120
aacgtgtatc agttccaaca gggtacgagc agcctgacta atgaattttc tcagaagaat    180
gcattctatg gtacgaccga taaggatatt gagactgtgg atggctacct gaccgcagat    240
agctggtatc gcccgaaatt catcctgaag gatggcaaga cgtggaccgc gagcacggaa    300
acggatctgc gtccgctgtt gatggcatgg tggccggaca agcgtaccca aatcaactat    360
ctgaactaca gggtctgggt gcgggtcgct ttgagaacaa agtggagcag    420
gccctgctga cgggtgcaag ccaacaggta caacgcaaga tcgaagagaa gattggtaaa    480
gagggtgata ccaagtggct gcgcaccctg atgggtgcgt tcgtgaaaac gcaaccaaac    540
tggaatatca aaaccgagtc tgaaacgacc ggcacgaaaa aggaccatct gcaaggcggt    600
gcactgctgt atacgaacaa cgagaaatcc ccgcacgcgg acagcaaatt tcgtctgctg    660
aatcgtaccc cgaccagcca aaccggcacg ccgaagtatt tcatcgacaa gtctaacgat    720
ggctacgaat ttctgctggc gaacgatttt gacaatagca atcctgcggt acaagctgag    780
cagctgaatt ggctgcacta catgatgaac tttggcagca ttgttgcgaa tgatccgacc    840
gcgaatttcg acggcgttcg tgtggatgct gttgataacg tcaatgcgga cttgttgcaa    900
attgcaagcg attactttaa gagccgttac aaagtcggtg agagcgaaga gaaagcgatc    960
aagcaccgtg tccatcctgg agcatggagc gataacgacc cggactacaa caaagatacc   1020
aagggtgcac agttggcgat tgataacaaa ctgcgcctga gcctgctgta ctctttcatg   1080
cgtaatctga gcatccgtag cggtgttgaa ccgacgatta ccaatagcct gaatgaccgt   1140
tccagcgaaa agaagaacgg cgagcgtatg caaaattaca tcttcgtgcg tgcccacgat   1200
agcgaggtcc aaacggtgat cgccgacatc attcgcgaaa acatcaatcc gaacaccgac   1260
ggcctgacgt ttacgatgga cgagctgaag caggcattca agatttacaa cgaggacatg   1320
cgcaaggcgg acaaaaagta tacccagttt aacattccta ccgcacacgc gctgatgctg   1380
tctaataagg attctattac ccgcgtgtac tatggtgatc tgtatactga cgatggtcag   1440
tacatggaga agaaaagccc gtatcacgat gcgattgacg ctctgctgcg tgcacgtatt   1500
aaatacgtcg cgggtggcca ggatatgaaa gtgacctata tgggcgtgcc gcgtgaagcg   1560
gataagtgga gctataacgg cattctgacc agcgtgcgct atggcacggg cgctaacgaa   1620
gccacggatg agggcactgc ggaaacgcgc acgcaaggta tggcagtgat tgcgagcaat   1680
aatccaaatc tgaaactgaa tgaatgggac aagttgcaag tcaacatggg tgcggcgcat   1740
aagaatcaat attccgtcc ggttctgctg accactaagg acggtatcag ccgttatctg   1800
accgatgaag aagtgcctca gagcctgtgg aaaaagacgg acgcaaacgg tattctgacc   1860
ttcgacatga atgatattgc tggctacagc aacgtgcaaa ttagcggtta cctggccgtc   1920
tgggtcccgg tcggtgcgaa ggcggatcaa gatgcgcgca cgaccgcatc caagaagaaa   1980
aatgcgtcgg gtcaggtgta cgaaagcagc gcggctctgg atagccagct gatttacgaa   2040
ggtttcagca actttcaaga ctttgccact cgcgatgatc agtacacgaa caaggtcatt   2100
gcgaaaaacg tgaatctgtt caaagaatgg ggtgtgacca gcttcgagct gccgccgcag   2160
tacgtgacga gccaagatga cacctttctg gacagcatta tccaaaacgg ctatgctttt   2220
gaagaccgtt acgatatggc gatgagcaag aataacaagt atggtagcct gaaagacctg   2280
ttgaacgcgc tgcgcgcact gcacagcgtc aacattcaag caatcgccga ttgggtgccg   2340
gaccaaattt caacttgcc gggcaaagag gtggtgaccg caactcgtgt caacaactac   2400
ggcacctacc gtgagggtgc tgaaatcaaa gaaaagcgtg atgtcgccaa tagcaagac   2460
aacgaaaccg atttccaagg taaatacggt ggtcgcttcc tggatgcgt gaaggcgaag   2520
tacccggaga ttttcgagcg tgtccaaatc agcaacggcc aaaagatgac taccgatgaa   2580
aagatcacca aatggagcgc gaaatacttt aatgcacca atattctggg tcgtggcgcg   2640
tactatgtcc tgaaagattg ggccagcaat gattacctga cgaaccgtaa cggcgagatt   2700
gtttttgccga agcaactggt taacaagaat agctataccg gctttgtcag cgacgcgaac   2760
ggcacgaagt tctattctac cctgtggctac caggcgaaga cgatcatt tcaagcgaa    2820
aacggtaatt ggtattactt tgacaaacgt ggttatctgg ttacgggcgc acacgagatt   2880
gatggcaagc atgtctactt cctgaaaaac ggtatccaac tgcgtgacag catccgtgag   2940
gatgagaacg gtaatcaata ctattacgac cagaccggcg cacaagtgct gaaccgttac   3000
tacacgacgg acggtcagaa ttggcgctat ttcgatgcga aagtgttat ggcacggcgc    3060
ctggtaaaga ttggtgacgg ccaacagttt ttcgatgaaa acggttacca ggtcaagggc   3120
```

```
aagattgtta gcgcaaaaga cggcaagctg cgctactttg ataaagactc tggcaatgct  3180
gtcattaatc gtttcgcgca gggtgacaat ccgagcgact ggtactattt cggtgtggaa  3240
tttgctaaac tgacgggttt gcaaaagatc ggccagcaga cgctgtattt tgaccaagac  3300
ggtaagcaag tcaaaggtaa gatcgtaact ctgtcggaca aaagcattcg ttacttcgat  3360
gccaacagcg gtgaaatggc ggttgcaag ttcgcggaag gtgcaaagaa tgagtggtat  3420
tatttcgata aaaccggcaa agcggttact ggtttgcaga aaattggtaa gcagaccctg  3480
tactttgacc aggacggtaa acaggttaaa ggcaaggttg tcacgctggc tgataaaagc  3540
atccgctact tcgacgcaga ctccggcgag atggcggtcg gtaagtttgc agagggtgcg  3600
aagaacgagt ggtactattt tgatcagact ggcaaggccg tgactggttt gcaaaagat  3660
gacaagcaaa ccttgtactt cgaccaggac ggtaaacaag tcaagggtaa gattgtgacg  3720
ttgagcgaca agtcgatccg ttactttgat gctaatagcg gtgagatggc tactaacaaa  3780
tccgtcgagg gctcgcagaa tgaatggtac tacttcgatc aagcgggtaa ggctgttacg  3840
ggcttgcaac aggtcggtca gcaaactctg tacttcaccc aggatggtaa gcaagtgaag  3900
ggtaaggtcg tggacgtgaa cggtgtttct cgttatttcg acgcaaactc cggtgacatg  3960
gctcgttcta aatggattca actgaagat ggcagctgga tgtatttcga ccgtgacggt  4020
cgtggccaga attttggccg taactaa                                      4047

SEQ ID NO: 16             moltype = AA   length = 1348
FEATURE                   Location/Qualifiers
source                    1..1348
                          mol_type = protein
                          organism = Streptococcus oralis
SEQUENCE: 16
MIDGKNYYVQ DDGTVKKNFA VELNGRILYF DAETGALVDS NEYQFQQGTS SLNNEFSQKN   60
AFYGTTDKDI ETVDGYLTAD SWYRPKFILK DGKTWTASTE TDLRPLLMAW WPDKRTQINY  120
LNYMNQQGLG AGAFENKVEQ ALLTGASQQV QRKIEEKIGK EGDTKWLRTL MGAFVKTQPN  180
WNIKTESETT GTKKDHLQGG ALLYTNNEKS PHADSKFRLL NRTPTSQTGT PKFYIDKSNG  240
GYEFLLANDF DNSNPAVQAE QLNWLHYMMN FGSIVANDPT ANFDGVRVDA VDNVNADLLQ  300
IASDYFKSRY KVGESEEEAI KHLSILEAWS DNDPDYNKDT KGAQLAIDNK LRLSLLYSFM  360
RNLSIRSGVE PTITNSLNDR SSEKKNGERM ANYIFVRAHD SEVQTVIADI IRENINPNTD  420
GLTFTMDELK QAFKIYNEDM RKADKKYTQF NIPTAHALML SNKDSITRVY YGDLYTDDGQ  480
YMEKKSPYHD AIDALLRARI KYVAGGQDMK VTYMGVPREA DKWSYNGILT SVRYGTGANE  540
ATDEGTAETR TQGMAVIASN NPNLKLNEWD KLQVNMGAAH KNQYYRPVLL TTKDGISRYL  600
TDEEVPQSLW KKTDANGILT FDMNDIAGYS NVQVSGYLAV WVPVGAKADQ DARTTASKKK  660
NASGQVYESS AALDSQLIYE GFSNFQDFAT RDDQYTNKVI AKNVNLFKEW GVTSFELPPQ  720
YVSSQDGTFL DSIIQNGYAF EDRYDMAMSK NNKYGSLKDL LNALRALHSV NIQAIADWVP  780
DQIYNLPGKE VVTATRVNNY GTYREGAEIK EKLYVANSKT NETDFQGKYG GAFLDELKAK  840
YPEIFERVQI SNGQKMTTDE KITKWSAKYF NGTNILGRGA YYVLKDWASN DYLTNRNGEI  900
VLPKQLVNKN SYTGFVSDAN GTKFYSTSGY QAKNSFIQDE NGNWYYFDKR GYLVTGAHEI  960
DGKHVYFLKN GIQLRDSIRE DENGNQYYYD QTGAQVLNRY YTTDGQNWRY FDAKGVMARG 1020
LVKIGDGQQF FDENGYQVKG KIVSAKDGKL RYFDKDSGNA VINRFAQGDN PSDWYYFGVE 1080
FAKLTGLQKI GQQTLYFDQD GKQVKGKIVT LSDKSIRYFD ANSGEMAVGK FAEGAKNEWY 1140
YFDKTGKAVT GLQKIGKQTL YFDQDGKQVK GKVVTLADKS IRYFDADSGE MAVGKFAEGA 1200
KNEWYYFDQT GKAVTGLQKI DKQTLYFDQD GKQVKGKIVT LSDKSIRYFD ANSGEMATNK 1260
FVEGSQNEWY YFDQAGKAVT GLQQVGQQTL YFTQDGKQVK GKVVDVNGVS RYFDANSGDM 1320
ARSKWIQLED GSWMYFDRDG RGQNFGRN                                    1348

SEQ ID NO: 17             moltype = DNA   length = 4047
FEATURE                   Location/Qualifiers
source                    1..4047
                          mol_type = other DNA
                          organism = Streptococcus sanguinis
SEQUENCE: 17
atgattgatg gtaaaaagta ttacgtacag gacgacggca cggttaagaa gaatttcgcg   60
gttgagctga atggcaagat cctgtacttc gatgcagaga ctggtgcgtt gattgacagc  120
gcggagtatc aattccaaca aggcaccagc agcctgaata atgagttcac tcaaaagaac  180
gccttttacg gtacgaccga taaggatgtg gaaaccattg atggttactt gaccgccgat  240
tcctggtatc gtccgaagtt cattctgaaa gatggcaaaa cctggacggc gagcacggaa  300
attgacttgc gtccgttgtt gatggcgtgg tggccggaca aacagaccca ggttagctac  360
ctgaattaca tgaaccagca aggcttgggt gcaggcgcct tcgaaaacaa agtagagcag  420
gcaattctga ccggtgcgtc ccaacaggta caacgtaaaa tcgaagaacg catcggtaaa  480
gagggtgata ccaagtggct gcgtaccctg atgggtgcat ttgtaaagac ccagccgaac  540
tggaacatta agaccgagtc cgaaaccact ggcacgaata aagatcatct gcaaggtggc  600
gcactgtgt atagcaattc cgacaagacg agccatgccc actctaagta ccgtatcctg  660
aaccgcaccc cgaccaacca aacgggcacg ccgaaatact ttattgacaa gagcaatggt  720
ggttatgaat tcctgctggc gaatgacttt gacaatagca atccggcagt gcaagcggaa  780
cagctgaact ggttgcactt tatgatgaat tttggctcca tcgttgcaaa tgatccgacg  840
gccaacttcg acggcgtccg cgttgacgct gtggataaag tgaatgcgga tctgttgcaa  900
attgcgagcg actatttcaa gagccgctat aaagtcgagg aaagcgaaga aggccatc   960
aagcacctgt ccatcctgga agcgtggagc gacaacgacc cggactacaa caaggatact 1020
aaaggtgccc aactgccgat cgacaacaaa ctgcgtctga gcctgctgta ctccttcatg 1080
cgtaagctga gcatccgtag cggcgtcgag ccgaccatca ccaactctct gaatgatcgc 1140
agcacggaga agaagaatgg tgagcgtatg caaactata tcttcgttcg tgcacatgat 1200
agcgaggtgc aaacggtcat cgccgacatt atccgtgaga acatcaatcc gaataccgac 1260
ggcctgacgt tcacgatgga tgaactgaag caggccttta aaatttacaa taggatatg 1320
cgtaaagccg acaaaaagta cacgcagttc aatatcccga ccgcgcacgc gctgatgctg 1380
agcaacaaag attctatcac ccgcgtttac tacggtgacc tgtatacgga tgacggtcag 1440
tatatggaaa agaaaagccc gtatcacgac gccattgacg ctctgctgcg tgcgcgtatc 1500
aaatatgttg cgggtggtca ggacatgaag gtgacctata tgggcgtgcc cgcgtgaggca 1560
```

```
gataaatgga gctataacgg catcctgacc agcgttcgtt atggtacggg tgccaacgag    1620
gcaaccgacg agggtacggc agaaacccgt acccagggca tggccgtcat tgccagcaac    1680
aatccgaacc tgaaactgaa cgagtgggac aagttgcagg tcaacatggg tgcagctcac    1740
aaaaaccaat actatcgtcc ggtgctgctg accaccaagg acggcatctc gcgctacctg    1800
accgacgaag aagtcccgca gagcctgtgg aaaaagacag atgcgaacgg catcttgacg    1860
tttgacatga atgatattgc gggttacagc aacgtccaag tgagcggtta tctggccgtc    1920
tgggttcctg tgggtgcgaa ggcggaccag gacgctcgtg ttacggcatc taagaagaaa    1980
aatgcctctg gccaagttta cgaaagcagc gcagccctgg actcccagct gatctatgag    2040
ggcttcagca attttcagga ctttgccacc cgtgacgacc agtacactaa caaggttatc    2100
gcgaaaaacg tcaatctgtt taaagagtgg ggcgtcacca gcttcgaatt gccgccacag    2160
tatgtgagca gccaagacgg tacgttcctg gatagcatca tccagaatgg ttatgcattc    2220
gaagatcgct atgatatggc gatgagcaaa aacaataagt acggtagctt gaacgacctg    2280
ttgaacgcct tgcgtgcact gcatagcgtg aatatccaag cgattgcgga ttgggtgccg    2340
gaccagattt acaatctgcc gggtaaagaa gttgtcactg caacccgtgt taacaattat    2400
ggcacgtatc gtgagggtag cgagattaaa gagaacctgt acgttgctaa caccaaaacc    2460
aatggtacgg actaccaagg taagtatggt ggtgcgttct tggacgagct gaaagccaaa    2520
taccctgaga ttttgagcg cgtccaaatc agcaacggcc agaagatgac caccgacgag    2580
aagattacga aatggtccgc caaacacttt aacggcacga acattctggg tcgtggtcga    2640
tattatgtgc tgaaagactg ggcgagcaac gagtacctga ataacaaaaa tggcgagatg    2700
gttctgccga gcagctggt taataaaaat gcatataccg gcttcgtcag cgacgcgagc    2760
ggcaccaaat actattctac cagcggctat caggctcgta atagctttat tcaagatgaa    2820
aatgctaatt ggtactactt caataaccgt ggttatttgg tgacgggtgc acaggaaatc    2880
gacggtaagc aactgtattt cctgaaaaac ggcattcagc tgcgtgattc tctgcgtgag    2940
gacgaaaacg gcaaccagta ttactatgat aagacgggtg cgcaagttct gaatcgttat    3000
tacactacga cggccaaaa ttggcgctac ttcgacgtta aaggcgtcat ggcccgtggt    3060
ctggtcacga tgggtggtaa ccaacaattc tttgaccaaa acggttacca ggttaaaggc    3120
aaaattgcgc gtgcaaaaga cggtaaactg cgttacttcg ataaagacag cggtaatgcg    3180
gcagctaacc gtttcgccca aggcgataac cctagcgact ggtactattt cggtgcagat    3240
ggtgttgcgg ttacgggcct gcaaaaggtt ggtcagcaaa ctctgtactt tgatcaggac    3300
ggcaagcagg tgaaaggtaa agttgttacc ttggcgcaaa aaagcattcg ttatttcgat    3360
gcaaacagcg gcgagatggc ggtgaacaag tttgtggaag tgctaagaa cgtgtggtac    3420
tacttcgatc aagcaggcaa agcggtgacc ggcctgcaaa ccatcaataa acaagtgctg    3480
tatttcgacc aggatggtaa acaagtcaaa ggtaaggtgg tcacgctggc tgataagtct    3540
atccgctact tcgacgcgaa caacgaagaa atggcagtgg caaattcgc cgaaggcgca    3600
aagaatgagt ggtattactt tgaccaggcg gcaaggctg ttaccggtct gcaaaagatc    3660
ggccaacaga cgctgtattt cgaccagaac ggtaaacagg ttaagggtaa agtggtcacc    3720
ctggcggata gagcatccg ctatttcgac gctaactctg gcgaaatggc aagcaataag    3780
ttcgttgagg gtgccaaaaa tgaatggtac tatttcgatc aggctggcaa ggcagtacg    3840
ggtctgcaac aaattggcca gcagaccctg tattttgacc aaatggcaa acaggtgaag    3900
ggtaagattg tgtatgttaa tggtgcgaat cgctactttg atgccaatag cggtgaaatg    3960
gcgcgtaaca gtggattcga gctggaagat ggcagctgga tgtattttga ccgcaatggt    4020
cgtggtcgtc gtttcggttg gaactaa                                      4047
```

```
SEQ ID NO: 18          moltype = AA   length = 1348
FEATURE                Location/Qualifiers
source                 1..1348
                       mol_type = protein
                       organism = Streptococcus sanguinis
SEQUENCE: 18
MIDGKKYYVQ DDGTVKKNFA VELNGKILYF DAETGALIDS AEYQFQQGTS SLNNEFTQKN    60
AFYGTTDKDV ETIDGYLTAD SWYRPKFILK DGKTWTASTE IDLRPLLMAW WPDKQTQVSY   120
LNYMNQQGLG AGAFENKVEQ AILTGASQQV QRKIEERIGK EGDTKWLRTL MGAFVKTQPN   180
WNIKTESETT GTNKDHLQGG ALLYSNSDKT SHANSKYRIL NRTPTNQTGT PKYFIDKSNG   240
GYEFLLANDF DNSNPAVQAE QLNWLHFMMN FGSIVANDPT ANFDGVRVDA VDNVADLLQ    300
IASDYFKSRY KVGESEEEAI KHLSILEAWS DNDPDYNKDT KGAQLPIDNK LRLSLLYSFM   360
RKLSIRSGVE PTITNSLNDR STEKKNGERM ANYIFVRAHD SEVQTVIADI IRENINPNTD   420
GLTFTMDELK QAFKIYNEDM RKADKKYTQF NIPTAHALML SNKDSITRVY YGDLYTDDGQ   480
YMEKKSPYHD AIDALLRARI KYVAGGQDMK VTYMGVPREA DKWSYNGILT SVRYGTGANE   540
ATDEGTAETR TQGMAVIASN NPNLKLNEWD KLQVNMGAAH KNQYYRPVLL TTKDGISRYL   600
TDEEVPQSLW KKTDANGILT FDMNDIAGYS NVQVSGYLAV WVPVGAKDQ DARVTASKKK   660
NASGQVYESS AALDSQLIYE GFSNFQDFAT RDDQYTNKVI AKNVNLFKEW GVTSFELPPQ   720
YVSSQDGTFL DSIIQNGYAF EDRYDMAMSK NNKYGSLNDL LNALRAHSV NIQAIADWVP   780
DQIYNLPGKE VVTATRVNNY GTYREGSEIK ENLYVANTKT NGTDYQGKYG GAFLDELKAK   840
YPEIFERVQI SNGQKMTTDE KITKWSAKHF NGTNILGRGA YYVLKDWASN EYLNNKNGEM   900
VLPKQLVNKN AYTGFVSDAS GTKYYSTSGY QARNSFIQDE NGNWYYFNNR GYLVTGAQEI   960
DGKQLYFLKN GIQLRDSLRE DENGNQYYYD KTGAQVLNRY YTTDGQNWRY FDVKGVMARG  1020
LVTMGGNQQF FDQNGYQVKG KIARAKDGKL RYFDKDSGNA AANRFAQGDN PSDWYYFGAD  1080
GVAVTGLQKV GQQTLYFDQD GKQVKGKVVT LADKSIRYFD ANSGEMAVNK FVEGAKNVWY  1140
YFDQAGKAVT GLQTINKQVL YFDQDGKQVK GKVVTLADKS IRYFDANSGE MAVGKFAEGA  1200
KNEWYYFDQA GKAVTGLQKI GQQTLYFDQN GKQVKGKVVT LADKSIRYFD ANSGEMASNK  1260
FVEGAKNEWY YFDQAGKAVT GLQQIGQQTL YFDQNGKQVK GKIVYVNGAN RYFDANSGEM  1320
ARNKWIQLED GSWMYFDRNG RGRRFGWN                                     1348

SEQ ID NO: 19          moltype = DNA   length = 4023
FEATURE                Location/Qualifiers
misc_feature           1..4023
                       note = unknown Streptococcus sp. C150
source                 1..4023
                       mol_type = other DNA
```

```
                     organism = unidentified
SEQUENCE: 19
atgatcgacg gcaaatacta ctacgtaaac gaggacggca gccacaaaga gaatttcgcg    60
atcacggtta atggtcaact gctgtatttt ggtaaggatg gcgcgctgac cagcagcagc   120
acgtacagct tcacccaagg cactaccaat atttgtggacg gttttagcat taacaaccgt   180
gcgtatgact ccagcgaggc ctctttcgag ctgattgacg gttatctgac tgcggactct   240
tggtaccgtc cggcgagcat tatcaaagac ggtgtgacgt ggcaagcatc caccgccgag   300
gacttccgcc cgttgctgat ggcgtggtgg ccgaacgttg atactcaggt gaactacctg   360
aactacatgt ccaaagtctt taatctggat gctaaataca gctcgactga taaacaggaa   420
accctgaagg tggcggcgaa agatatccag atcaaaattg aacaaaagat tcaggcggaa   480
aagtccacgc aatggctgcg tgaaacgatc agcgcctttg taaaaaccca gccgcaatgg   540
aacaaagaga ctgagaacta cagcaagggc ggtggtgagg accatctgca aggtggtgcc   600
ctgctgtatg ttaatgactc tcgtaccccg tgggcgaaca gcaactatcg tttgctgaac   660
cgcacggcga ccaaccagac cggtacgatc gacaagagca tcctgacga cagagcgat   720
ccgaatcaca tgggtggttt tgatttcttg ctggctaatg acgttgactt gagcaatccg   780
gtcgtccagg cggaacaact gaatcagatc cactacctga tgaattgggg ttctattgtc   840
atgggtgata agacgcgaa ttttgacggt attcgtgtag acgcggtgga taatgttgat   900
gcggacatgc tgcaattgta caccaactat ttccgcgaat actatggtgt caacaaaagc   960
gaggcaaacg cgctggcgca cattagcgtc ctggaagcct ggagcctgaa tgacaaccat  1020
tacaatgata gactgatgt tgcggcgctc gcaatggaga ataagcagcg cttggcactg  1080
ttgtttagcc tggcgaaacc gattaaagaa cgcacgcctg ccgtgtctcc gctgtacaac  1140
aatacgttta acaccactca gcgtgatgaa aagacgact ggatcaataa agatggttcg  1200
aaagcctaca atgaggatgg cactgtcaag aaaagcacca tcggcaagta taacgagaag  1260
tatggtgatg ctagcggcaa ctacgttttc atccgcgctc acgacaataa cgtgcaagac  1320
atcatcgcg agatcattaa gaaagagatt aacgagaaat ctgacggttt taccattacg  1380
gattcggaa tgaagcgtgc atttgagatc tataacaaag acatgctgtc taatgacaaa  1440
aagtacacgc tgaataacat cccggcggc tacgcggtta tgctgcaaaa catggaaacg  1500
attacccgcg tgtattacgg cgatctgtac acggacgacg gtaattacat ggaagcgaaa  1560
agcccgtact acgatacgat tgttaacttg atgaagtctc gcatcaaata cgtgagcggt  1620
ggccaggcga agcgcagcta ctggctgccg accgatgtga agatggataa gtcggatgtt  1680
gagctgtacc gtacgaacga agtgtacacg agcgtccgtt acggcaaaga cattatgacc  1740
gccgatgaca cgcaaggtag caaatacagc cgtaccagcg gtcaggtgac cctggtcgtc  1800
aacaacccaa aactgacctt ggaccaaagc gcaaagctga acgtggttat gggcaagatt  1860
catgctaatc agaagtaccg cgcactgatt gtcggtaccc cgaacggtat taagaatttc  1920
accagcgacg cagaggctat tgccgcaggc tatgtcaaag aaaccgatgg caatggcgtg  1980
ctgaccttcg gtgcaaacga catcaagggt tatgaaactt tcgatatgag cggcttcgtc  2040
gctgtttggg ttccggtcgg tgcgagcgac gaccaagata ttcgtgtggc ggcgtctacg  2100
gcagcaaaga aagagggtga gctgacgctg aaagcgaccg aagcctatga ctcccaactg  2160
atctatgaag gctttagcaa tttccagacc atcccagatg gcgatcc ttctgtttat  2220
accaatcgta agatcgcgga aaatgttgat tgttcaaga gctggggtgt cacgagcttc  2280
gaaatggctc cgcagttcgt ttctgcggac gatggcacgt ttctggacag cgtcattcaa  2340
aacggctatg cgttcgcaga ccgttatgat ctggccatga gcaaaacaa taagtacggt  2400
agcaaagaag atctgcgtaa cgcgctgaag gcactgcaa caggcat tcaggcgatt  2460
gcagattggg tgccagacca aatctaccag ctgcctggca agaagttgt tactgccacc  2520
cgcacggacg gtgctggtcg caaaatcagc gatgcaatca tcgatcattc cctgtacgtt  2580
gcgaactcca agagctccgg taaggactac caagcgaagt acggtggcga gttcttggcg  2640
gaactgaagg cgaaataccc ggaaatgttc aaagtgaaca tgattagcac cggcaaaccg  2700
attgatgata gcgtgaaact gaagcagtgg aaagcagaat acttcaacgg caccaatgtg  2760
ctggatcgcg tgtcggtta tgttctgagc gatgaggcaa ccggtaagta tttcaccgtt  2820
accaaagagg gtaactttat cccgttgcag ctgaagggta caagaaggt gattaccggc  2880
ttttccagcg acggtaaggg cattacctat ttcggtacta gcggtaacca agctaaattc  2940
gcgttcgtca cttttaacgg taacacgtac tacttcgacg cacgtggcca catggttacc  3000
aacggtgagt actcgccgaa tggtaaagat gtgtatcgtt ttctgccgaa cggcattatg  3060
ctgagcaacg cgttctatgt tgacggcaat ggcaacacct acctgtacaa ctccaaaggc  3120
caaatgtata aagtggcta tagcaaattt gactctcacgg aaacgaaagc cggtaaagag  3180
agcaaagttg tcaagttccg ctactttacg aacgagcgcg tgatggcgaa aggtgtcacg  3240
gttgtggatg cgttcactca gtactttaac gaggatggca ttcaaagcaa agacgagctg  3300
gtcacttaca atggcaagac ctattacttc gaagcacaca cggcaatgc cattaagaat  3360
acgtggcgta atatcaaggg caaatggtac catttgatg ctaacggtgt cgcggctact  3420
ggcgcacagg ttatcaacgg tcagcacctg tacttcaatg aagatggctc tcaagtaaaa  3480
ggtagcatcg tcaaaaacgc tgatggtacg ttcagcaagt acaaggacag ctctggcgat  3540
ctggtggtga acgagttttt cacgacgggt gataacgtct ggtactatgc tggtgccaat  3600
ggcaaaacgg ttactggtgc acaggtgatt aatggccagc acttgttctt caagagggat  3660
ggcagccagg tcaagggcga ctttgtgaag aatagcgacg tgcacctact caagtatgac  3720
gctgcgagcg cgaacgtctc gaccaacgag ttcttcacta cgggcgacaa tcattggtac  3780
tatattggcg ccaacggtaa gaccgttacc ggtgaagtta agattggtga cgacacgtat  3840
ttcttcgcaa aagacggtaa gcaactgaaa ggtcaaatcg ttaccacccg tagcggtcgt  3900
atcagctact actttggtga tagcggtaag aaggctatta gcacgtgggt ggagatccag  3960
ccgggtgtgt ttgttttctt cgacaaaaac ggcctggctt acccaccgga gaatatgaac  4020
tga                                                                4023
SEQ ID NO: 20            moltype = AA  length = 1340
FEATURE                  Location/Qualifiers
REGION                   1..1340
                         note = unknown Streptococcus sp. C150
source                   1..1340
                         mol_type = protein
                         organism = unidentified
SEQUENCE: 20
```

```
MIDGKYYYVN EDGSHKENFA ITVNGQLLYF GKDGALTSSS TYSFTQGTTN IVDGFSINNR    60
AYDSSEASFE LIDGYLTADS WYRPASIIKD GVTWQASTAE DFRPLLMAWW PNVDTQVNYL   120
NYMSKVFNLD AKYSSTDKQE TLKVAAKDIQ IKIEQKIQAE KSTQWLRETI SAFVKTQPQW   180
NKETENYSKG GGEDHLQGGA LLYVNDSRTP WANSNYRLLN RTATNQTGTI DKSILDEQSD   240
PNHMGGFDFL LANDVDLSNP VVQAEQLNQI HYLMNWGSIV MGDKDANFDG IRVDAVDNVD   300
ADMLQLYTNY FREYYGVNKS EANALAHISV LEAWSLNDNH YNDKTDVAAL AMENKQRLAL   360
LFSLAKPIKE RTPAVSPLYN NTFNTTQRDE KTDWINKDGS KAYNEDGTVK KSTIGKYNEK   420
YGDASGNYVF IRAHDNNVQD IIAEIIKKEI NEKSDGFTIT DSEMKRAFEI YNKDMLSNDK   480
KYTLNNIPAA YAVMLQNMET ITRVYYGDLY TDDGNYMEAK SPYYDTIVNL MKSRIKYVSG   540
GQAQRSYWLP TDGKMDKSDV ELYRTNEVYT SVRYGKDIMT ADDTQGSKYS RTSGQVTLVV   600
NNPKLTLDQS AKLNVVMGKI HANQKYRALI VGTPNGIKNF TSDAEAIAAG YVKETDGNGV   660
LTFGANDIKG YETFDMSGFV AVWVPVGASD DQDIRVAAST AAKKEGELTL KATEAYDSQL   720
IYEGFSNFQT IPDGSPSVY TNRKIAENVD LFKSWGVTSF EMAPQFVSAD DGTFLDSVIQ   780
NGYAFADRYD LAMSKNNKYG SKEDLRNALK ALHKAGIQAI ADWVPDQIYQ LPGKEVVTAT   840
RTDGAGRKIS DAIIDHSLYV ANSKSSGKDY QAKYGGEFLA ELKAKYPEMF KVNMISTGKP   900
IDDSVKLKQW KAEYFNGTNV LDRGVGYVLS DEATGKYFTV TKEGNFIPLQ LKGNKKVITG   960
FSSDGKGITY FGTSGNQAKS AFVTFNGNTY YFDARGHMVT NGEYSPNGKD VYRFLPNGIM  1020
LSNAFYVDGN GNTYLYNSKG QMYKGGYSKF DVTETKDGKE SKVVKFRYFT NEGVMAKGVT  1080
VVDGFTQYFN EDGIQSKDEL VTYNGKTYYF EAHTGNAIKN TWRNIKGKWY HFDANGVAAT  1140
GAQVINGQHL YFNEDGSQVK GSIVKNADGT FSKYKDSSGD LVVNEFFTTG DNVWYYAGAN  1200
GKTVTGAQVI NGQHLFFKED GSQVKGDFVK NSDGTYSKYD AASGERLTNE FFTTGDNHWY  1260
YIGANGKTVT GEVKIGDDTY FFAKDGKQLK GQIVTTRSGR ISYYFGDSGK KAISTWVEIQ  1320
PGVFVFFDKN GLAYPPENMN                                             1340

SEQ ID NO: 21          moltype =     length =
SEQUENCE: 21
000

SEQ ID NO: 22          moltype =     length =
SEQUENCE: 22
000

SEQ ID NO: 23          moltype =     length =
SEQUENCE: 23
000

SEQ ID NO: 24          moltype =     length =
SEQUENCE: 24
000

SEQ ID NO: 25          moltype = DNA   length = 4308
FEATURE                Location/Qualifiers
source                 1..4308
                       mol_type = other DNA
                       organism = Streptococcus sobrinus
SEQUENCE: 25
atggttgacg gcaaatacta ctattatgat caggatggca acgttaagaa gaatttcgcg    60
gttagcgttg gtgacaagat ctactacttt gacgagactg gtgcctacaa agacacctct   120
aaagtggacg cggacaagtc tagcagcgcc gttagccaaa atgcgacgat ctttgcggct   180
aacaatcgtg cgtatagcac ctctgctgag aactttgagg ccgttgataa ctatctgacg   240
gcagatagct ggtatcgtcc taaatctatt ctgaaagatg gcaagacgtg gaccgagtcg   300
ggtaaggacg acttccgtcc gctgctgatg gcgtggtggc cggacacgga gactaaacgc   360
aattacgtga attacatgaa cctggttgtc ggcatcgaca agacgtacac cgcggaaacc   420
tctcaagcag atttgaccgc agcggcggag ctggtccagg cgcgtattga acagaaaatc   480
accacggaac agaatacgaa atggctgcgc gaggcgatct ctgctttcgt caagacccag   540
ccgcagtgga atggtgaaag cgagaagccc tatgacgacc cctgcaaaa cggtgctctg   600
aaattcgata tcagagcga cctgaccccg gacacccaga gcaactatcg cctgctgaat   660
cgcacccccg ctaaccagac tggcagcctg acagccgtt tcacctataa tgcgaacgat   720
ccgttgggtg gctacgaatt tctgctggct aacgacgtgg ataatagcaa ccctgtggtg   780
caggcagaac aactgaactg gttgcattac ctgttgaatt ttggtagcat ttacgcgaaa   840
gatgcggatg caacttcga ttccatccgt gtgacgccg tggacaacgt cgatgcagat   900
ctgttcagaa ttagcagcga ttacctgaag gcagcctatg gcattgacaa gaacaataag   960
aacgcgaaca accatgttag cattgttgag gcttggagcg ataacgatac gccgtacctg  1020
cacgatgcg gtgataacct gatgaacatg gacaatagt tccgcttgg catgctggat  1080
agcctggcca agccgctgga caagcgcagc ggtctgaatc ctctgattca taacagcctg  1140
gtggaccgtg aggttgatga ccgtgaagtg gaaacggttc cgagctactc ttttgcgcgt  1200
gcgcatgatt ccgaggtcca agacattatc cgcgacatta tcaaggccga aatcaacccg  1260
aatagcttg gttatagctt cacccaagaa gagattgacc aggcgtttaa gatctataat  1320
gaagatctga agaaaaccga caagaaatac acccactaca atgtcccgtt gagctatact  1380
ttgctgctga cgaataaagg ttcgattccg cgtgtgtatt acggtgatat gttcaccgat  1440
gatggtcaat acatgcgaa caaaacggtt aactatgatg ccattgagtc gctgctgaaa  1500
gcgcgcatga agtacgttag cggcggtcaa gcgatgcaaa actatcaaat cggcaatggt  1560
gagattctga ccagcgttcg ttatggtaag ggtgcattga gcaatccga caagggtgac  1620
gcgaccacga gtacgtccga tgtgggcgtc ggcagccagc catttagcctg  1680
gacggcaagg tggtgcatt gaacatgggt gccgctcatg caaatcagga gtatcgtgcg  1740
ctgatggtga gcaccaagga tggcgttgcc acgtatgcca ccgacgcgga cgcaagcaag  1800
gcaggtctgt caaacgcac cgatgaaaat ggttatttgt actttctgaa cgacgatctg  1860
aagggtgtgg caaacccaca agtcagcggt tccttgcagg tgtgggtccc agtgggtgcg  1920
gctgacgatc aggacattcg tgttgcagcg agcgacacgg ctagcacgga cggtaagtcc  1980
```

```
ctgcatcaag atgcggcaat ggatagccgt gttatgtttg agggttttag caacttccag    2040
agctttgcaa ccaaagaaga agagtacacc aacgtagtta ttgcgaacaa cgtggacaaa    2100
ttcgttagct ggggtattac cgactttgag atggcaccgc aatatgtcag ctccaccgat    2160
ggccagtttc tggatagcgt tatccagaat ggttacgcgt tcaccgaccg ttatgatctg    2220
ggtatgagca aagccaacaa atacggtacc gcggatcagc tggttaaagc aatcaaagcg    2280
ttgcacgcga agggtctgaa ggtgatggcg gactgggttc cagaccagat gtacacgttt    2340
ccgaagcagg aagttgtcac tgtcacgcgc accgacaaat ttggtaagcc gattgcgggc    2400
agccaaatca tcacagcct gtacgtgacg gacaccaaat ccagcggtga tgattaccag    2460
gccaaatatg gtggtgcgtt cctggatgag ctgaaagaga aatacccgga gcttgttcac    2520
aaaaagcaga tctcgaccgg tcaggcgatc gacccgagcg tgaagattaa gcagtggagc    2580
gcgaaatact ttaatggtag caacattctg ggtcgtggtg ccgactacgt cctgtccgat    2640
caagttagca acaagtattt caatgtggcc agcgacacgc tgtttctgcc gtctagcctg    2700
ttgggtaagg ttgtcgaaag cggtattcgt tacgatggca aaggttatat ctataacagc    2760
agcgcgactg gcgaccaagt caaggcgtct tttatcacgg aagcaggcaa tctgtactac    2820
ttcggcaaag acggttacat ggttactggt gcgcagacca ttaacggtgc gaattacttc    2880
ttcttggaaa atggtacggc cctgcgtaat accatctaca ccgatgcaca gggcaactcc    2940
cactattatg ctaatgatgg caagcgttac gagaacggtt accagcagtt cggcaacgat    3000
tggcgttact tcaaagatgg taacatggcc gtcggtctga ccacggtgga tggtaacgtt    3060
cagtatttcg acaaggacgg tgtccaagct aaagacaaga ttattgtgac cgcgatggt     3120
aaggtgcgct actttgatca acacaatggc aacgcggtca cgaataccttt atcgccgac    3180
aagaccggtc actggtacta cctgggcaaa gatggcgtcg cggtcaccgg cgctcaaacc    3240
gtcggtaagc aaaaactgta ttttgaggcg aacggtagcg aggtaaaagg cgactttgtg    3300
actagccatg aaggcaaact gtacttttat gatgttgaca gcggcgacat gtggaccgat    3360
accttcatcg aggataaggc cggcaactgg ttctacctgg gtaaagacgg cgcagcagtt    3420
agcggtgcac agaccattcg cggtcaaaag ctgtacttca aggcgtacgg tcaacaggtc    3480
aaaggtgaca tcgttaaagg caccgacggc aagatccgtt actacgatgc gaaatcgggc    3540
gagcaggttt tcaataagac ggtcaaagcc gctgatgcca aaacctatgt gatcggcaac    3600
aatggtgtgg cggtcgatcc gagcgttgtt aagggtcaga cgttcaaaga cgccagcggc    3660
gcactgcgtt tttacaatct gaaaggtcaa ctggttacgg gctccggttg gtatgaaacg    3720
gccaatcacg attgggtgta tattcagagc ggtaaagcac tgccggtga gcaaacctac    3780
aatggtcagc acctgtactt taaagaagat ggccaccaag ttaaaggtca gctggtcacc    3840
cgtacggacg gcaaagtgcg ttactatgac gcaaattctg gcgatcaagc gttcaacaag    3900
tccgtgacgg ttaacggcaa aacgtattac ttcggtaatg atggtaccgc gcaaaccgcg    3960
ggtaaccgga aaggccaaat cttcaaggac ggcagcgttc tgcgtttcta tagcatggaa    4020
ggccagctgg taattggcag cggctgtat tccaacgcgc aaggccaatg gctgtatgtg    4080
aagaatggta aagtgttgac cggtttgcag accgtcggtt cccagcgcgt gtactttgat    4140
gagaatggca ttcaagcaaa aggcaaagcg gttcgcacga gcgacggcaa aattcgctac    4200
ttcgacgaga acagcggtag catgatcacc aatcaatgga gtttgttta cggtcaatac    4260
tattactttg gtaatgacgg tgcggcaatc taccgtggtt ggaattaa                 4308
```

SEQ ID NO: 26          moltype = AA   length = 1435
FEATURE                Location/Qualifiers
source                 1..1435
                       mol_type = protein
                       organism = Streptococcus sobrinus
SEQUENCE: 26
```
MVDGKYYYD  QDGNVKKNFA  VSVGDKIYYF  DETGAYKDTS  KVDADKSSSA  VSQNATIFAA    60
NNRAYSTSAE  NFEAVDNYLT  ADSWYRPKSI  LKDGKTWTES  GKDDFRPLLM  AWWPDTETKR   120
NYVNYMNLVV  GIDKTYTAET  SQADLTAAAE  LVQARIEQKI  TTEQNTKWLR  EAISAFVKTQ   180
PQWNGESEKP  YDDHLQNGAL  KFDNQSDLTP  DTQSNYRLLN  RTPTNQTGSL  DSRFTYNAND   240
PLGGYEFLLA  NDVDNSNPVV  QAEQLNWLHY  LLNFGSIYAK  DADANFDSIR  VDAVDNVDAD   300
LLQISSDYLK  AAYGIDKNNK  NANNHVSIVE  AWSDNDTPYL  HDDGDNLMNM  DNKFRLSMLW   360
SLAKPLDKRS  GLNPLIHNSL  VDREVDDREV  ETVPSYSFAR  AHDSEVQDII  RDIIKAEINP   420
NSFGYSFTQE  EIDQAFKIYN  EDLKKTDKKY  THYNVPLSYT  LLLTNKGSIP  RVYYGDMFTD   480
DGQYMANKTV  NYDAIESLLK  ARMKYVSGGQ  AMQNYQIGNG  EILTSVRYGK  GALKQSDKGD   540
ATTRTSGVGV  VMGNQPNFSL  DGKVVALNMG  AAHANQEYRA  LMVSTKDGVA  TYATDADASK   600
AGLVKRTDEN  GYLYFLNDDL  KGVANPQVSG  FLQVWVPVGA  ADDQDIRVAA  SDTASTDGKS   660
LHQDAAMDSR  VMFEGFSNFQ  SFATKEEEYT  NVVIANNVDK  FVSWGITDFE  MAPQYVSSTD   720
GQFLDSVIQN  GYAFTDRYDL  GMSKANKYGT  ADQLVKAIKA  LHAKGLKVMA  DWVPDQMYTF   780
PKQEVVTVTR  TDKFGKPIAG  SQINHSLYVT  DTKSSGDDYQ  AKYGGAFLDE  LKEKYPELFT   840
KKQISTGQAI  DPSVKIKQWS  AKYFNGSNIL  GRGADYVLSD  QVSNKYFNVA  SDTLFLPSSL   900
LGKVVESGIR  YDGKGYIYNS  SATGDQVKAS  FITEAGNLYY  FGKDGYMVTG  AQTINGANYF   960
FLENGTALRN  TIYTDAQGNS  HYYANDGKRY  ENGYQQFGND  WRYFKDGNMA  VGLTTVDGNV  1020
QYFDKDGVQA  KDKIIVTRDG  KVRYFDQHNG  NAVTNTFIAD  KTGHWYYLGK  DGVAVTGAQT  1080
VGKQKLYFEA  NGEQVKGDFV  TSHEGKLYFY  DVDSGDMWTD  TFIEDKAGNW  FYLGKDGAAV  1140
SGAQTIRGQK  LYFKAYGQQV  KGDIVKGTDG  KIRYYDAKSG  EQVFNKTVKA  ADGKTYVIGN  1200
NGVAVDPSVV  KGQTFKDASG  ALRFYNLKGQ  LVTGSGWYET  ANHDWVYIQS  GKALTGEQTI  1260
NGQHLYFKED  GHQVKGQLVT  RTDGKVRYYD  ANSGDQAFNK  SVTVNGKTYY  FGNDGTAQTA  1320
GNPKGQIFKD  GSVLRFYSME  GQLVIGSGWY  SNAQGQWLYV  KNGKVLTGLQ  TVGSQRVYFD  1380
ENGIQAKGKA  VRTSDGKIRY  FDENSGSMIT  NQWKFVYGQY  YYFGNDGAAI  YRGWN       1435
```

SEQ ID NO: 27          moltype = DNA   length = 4023
FEATURE                Location/Qualifiers
source                 1..4023
                       mol_type = other DNA
                       organism = Streptococcus salivarius
SEQUENCE: 27
```
atgattgacg gcaaatacta ctacgtaaac aaagatggcg cgcacaaaga gaatttcgca     60
attaccgtga atggtcagtt gttgtatttc ggtaaggacg gtgcattgac gtctagcagc    120
```

```
acctacagct ttacgcaggg caccaccaac atcgttgatg ctttagcaa aaacaaccgt    180
gcgtacgatt ccagcgaggc gagctttgaa ctgatcgacg ttatctgac cgcggactcc    240
tggtatcgtc cggtgagcat tatcaaggac ggcgttacgt ggcaagccag caccaaagag    300
gactttcgcc cgctgctgat ggcctggtgg ccgaatgttg acacccaggt caactacctg    360
aattacatgt cgaaggtgtt taacctggac gcgaagtata cgagcaccga caacaggtt    420
gacctgaatc gcgcagccaa ggacattcag gttaagattg agcaaaagat tcaggccgaa    480
aagagcactc aatggctgcg tgaagcgatt tcggccttcg tcaaaaccca gccgcagtgg    540
aataaagaaa cggagaactt ctccaagggt ggtggtgagg atcatctgca aggtggtgca    600
ctgctgtacg ttaacgaccc gcgtaccccg tgggctaact ccaactaccg cctgctgaat    660
cgtactgcga ccaaccagac cggcacgacg ttctggacga acagagcgat    720
cctaaccaca tgggcggctt cgattttctg ctggcgaatg acgtcgatac cagcaatccg    780
gtggtgcagg cggaacaact gaatcagatc cactacctga tgaattgggg ttccattgtt    840
atgggcgaca aagatgcaaa cttcgatggt atccgcgtgg acgcggtcga taacgttgac    900
gcagatatgc tgcaactgta caccaactac tttcgtgagt attatggcgt gaacaaaagc    960
gaggcaaacg ctttggcgca catctcggtc ctggaagcgt ggagcttgaa tgataatcac   1020
tataatgaca agactgacgg tgcggccctg cgatggaga acaaacagcg tttggccctg   1080
ctgtttagct tggcgaaacc gatcaaagaa cgtaccccctg cggtgagccc gctgtacaac   1140
aacactttca acacgacgca gcgtgacgaa aagaccgatt ggattaacaa agacggtagc   1200
aaagcctata atgaggacgg caccgtcaag cagtccacca tcggcaagta caacgagaaa   1260
tacggcgacg cgtccggcaa ttatgtgttc attcgcgccc acgataacaa cgtccaagac   1320
attattgcag agatcattaa gaaagaaatc aatccgaaaa gcgacggttt caccattacc   1380
gacgccgaaa tgaaaaggc attcgaaatc tacaacaagc atatgctgtc ctctgataag   1440
aaatacaccc tgaacaacat cccagcggcc tacgcggtga tgctgcaaaa catggaaacc   1500
attactcgtg tgtattacgg cgatctgtat accgacgatg ccattacat ggaaaccaag   1560
agcccgtact acgacaccat tgtgaacctg atgaagaacc gtatcaaata cgtgtccggt   1620
ggtcaagcgc aacgttccta ttggctgccg accgacgta agatggataa aagcgatgtc   1680
gaactgtatc gcaccaacga ggtgtacacc agcgtccgtt acggtaagga catcatgact   1740
gccgatgaca cccaaggtag caagtacagc cgtaccagcg gtcaggtgac cctggtggtg   1800
aacaacccga agctgtcttt ggataagagc gcgaagctgg acgtcgaaat gggcaagatc   1860
catgcaaacc agaaataccg tgctctgatc gtgggtacgc cgaacggcat caaaaacttc   1920
acgagcgacg ccgaggcaat cgcggctggc tacgtgaaag aaaccgacgg caatggtgtg   1980
ctgaccttcg gtgcaaatga catcaaaggt tacgaaacgt ttgacatgag cggtttcgtt   2040
gcagtttggg ttccggtagg tgcaagcgat gatcaagaca tccgtgtcgc cgcaagcacc   2100
gcggcaaaga aagaaggtga gctgacttg aaggcaactg aggcgtatga ctctcagctg   2160
atttacgaag ttttttcgaa ttttcagacc attccggatg gtagcgatcc gagcgtttac   2220
accaatcgta agatcgcgga aaatgttgat tgttcaaga gctggggtgt gacctctttc   2280
gaaatggcgc cacagtttgt gagcgcagac gacggtacgt ttctggacag cgttatccag   2340
aacggctatg cgtttgcgga ccgttatgat ctggcgatgt ccaaaaacaa taagtacggt   2400
tcgaaagaag atctgcgtaa cgcgttgaag gctttgcaca aggccggcat ccaagccatt   2460
gcggactggg ttccggatca gatctaccaa ctgccgggca aagaagtagt gaccgccact   2520
cgtaccgatg gtgccggtcg taagattagc gatgcaatta tcgatcacag cctgtacgtc   2580
gcaaacagca agtcgtctgg caaagactat caagctaaat acggtggtga gttcctggcc   2640
gagctgaaag caagtaccc ggaaatgttt aaagtcaact gattagcac gggtaaaccg   2700
atcgacgact ctgtcaaact gaagcaatgg aaggcggagt actttaacgg tacgaatgtt   2760
ctggaccgtg tgttggtta cgtcctgagc gatgaggcga cggcaagta ctttaccgtt   2820
acgaaagagg gtaactttat cccactgcaa ttgaaaggta acgagaaagt tatcacgggc   2880
ttcagctctg acggcaaggg cattacctat ttccgcaact ttcggtaatca acgcaaaagc   2940
gcttttgtca cgttcaatgg taatccctac tattttgacg cgcgtggcca catggttacc   3000
aacggcgaat atagccctaa tggtaaggat gtgtatcgtt tcctgccgaa tggtattatg   3060
ttgagcaatg cattctacgt tgacggtaac ggcaatacct acctgtacaa ctccaagggc   3120
caaatgtaca aagtggtta tagcaaattc gacgttacgg aaaccaaaga tggtaaagag   3180
agcaaagtgg tgaaatttcg ctactttacc aatgaaggtg tgatggcaaa aggtgttacc   3240
gtggtgacg cttcactca atacttcaac gaagatggca ttcagagcaa ggacgaactg   3300
gtgacctaca atggtaaaac ctattacttc gaagcgcata ccggtaatgc gatcaaaaac   3360
acgtgcgca atatcaaggg taagtggtat cactttgatg cgaatggcgt ggcggcaacg   3420
ggtgcacagg ttatcaatgg tcagcacctg tactttaatg aggatggttc ccaggtgaag   3480
ggtggcgtcg tgaagaatgc ggatggtacc ttcagcaagt ataaagatgg ttccggtgac   3540
ctggtggtca atgagttctt cactactggt gataacgtgt ggtactacgc tggtgccaac   3600
ggcaaaactg tgacgggtgc ccaggtcatc aatggcaac acctgttttt caaagaggac   3660
ggtagccagg ttaagggtga tttcgttaag aacagcgacg tgacctactc taagtatgat   3720
gcggccagcg cgaacggcct gacgaatgag ttttcacga ccggtgacaa ccactgtac   3780
tatattggtg ccaatggcaa aaccgttacc ggcgaagtca agatcggtga tgatacgtac   3840
ttcttcgcaa aagatggcaa gcagctgaag gccagatctg tgacgacccg cagcggtcgt   3900
atcagctact acttcggcga ctctggtaag aaggcgatta gcacctgggt ggagattcag   3960
ccgggtgttt tcgtgttttt cgacaaaaat ggcctggcat atccgccgga aaacatgaat   4020
taa                                                                 4023

SEQ ID NO: 28           moltype = AA   length = 1340
FEATURE                 Location/Qualifiers
source                  1..1340
                        mol_type = protein
                        organism = Streptococcus salivarius
SEQUENCE: 28
MIDGKYYYVN KDGSHKENFA ITVNGQLLYF GKDGALTSSS TYSFTQGTTN IVDGFSKNNR    60
AYDSSEASFE LIDGYLTADS WYRPVSIIKD GVTWQASTKE DFRPLLMAWW PNVDTQVNYL   120
NYMSKVFNLD AKYTSTDKQV DLNRAAKDIQ VKIEQKIQAE KSTQWLREAI SAFVKTQPQW   180
NKETENFSKG GGEDHLQGGA LLYVNDPRTP WANSNYRLLN RTATNQTGTI DKSVLDEQSD   240
PNHMGGFDFL LANDVDTSNP VVQAEQLNQI HYLMNWGSIV MGDKDANFDG IRVDAVDNVD   300
ADMLQLYTNY FREYYGVNKS EANALAHISV LEAWSLNDNH YNDKTDGAAL AMENKQRLAL   360
```

```
LFSLAKPIKE RTPAVSPLYN NTFNTTQRDE KTDWINKDGS KAYNEDGTVK QSTIGKYNEK    420
YGDASGNYVF IRAHDNNVQD IIAEIIKKEI NPKSDGFTIT DAEMKKAFEI YNKDMLSSDK    480
KYTLNNIPAA YAVMLQNMET ITRVYYGDLY TDDGHYMETK SPYYDTIVNL MKNRIKYVSG    540
GQAQRSYWLP TDGKMDKSDV ELYRTNEVYT SVRYGKDIMT ADDTQGSKYS RTSGQVTLVV    600
NNPKLSLDKS AKLDVEMGKI HANQKYRALI VGTPNGIKNF TSDAEAIAAG YVKETDGNGV    660
LTFGANDIKG YETFDMSGFV AVWVPVGASD DQDIRVAAST AAKKEGELTL KATEAYDSQL    720
IYEGFSNFQT IPDGSDPSVY TNRKIAENVD LFKSWGVTSF EMAPQFVSAD DGTFLDSVIQ    780
NGYAFADRYD LAMSKNNKYG SKEDLRNALK ALHKAGIQAI ADWVPDQIYQ LPGKEVVTAT    840
RTDGAGRKIS DAIIDHSLYV ANSKSSGKDY QAKYGGEFLA ELKAKYPEMF KVNMISTGKP    900
IDDSVKLKQW KAEYFNGTNV LDRGVGYVLS DEATGKYFTV TKEGNFIPLQ LKGNEKVITG    960
FSSDGKGITY FGTSGNQAKS AFVTFNGNTY YFDARGHMVT NGEYSPNGKD VYRFLPNGIM   1020
LSNAFYVDGN GNTYLYNSKG QMYKGGYSKF DVTETKDGKE SKVVKFRYFT NEGVMAKGVT   1080
VVDGFTQYFN EDGIQSKDEL VTYNGKTYYF EAHTGNAIKN TWRNIKGKWY HPFDANGVAAT   1140
GAQVINGQHL YFNEDGSQVK GGVVKNADGT FSKYKDGSGD LVVNEFFTTG DNVWYYAGAN   1200
GKTVTGAQVI NGQHLFFKED GSQVKGDFVK NSDGTYSKYD AASGERLTNE FFTTGDNHWY   1260
YIGANGKTVT GEVKIGDDTY FFAKDGKQLK GQIVTTRSGR ISYYFGDSGK KAISTWVEIQ   1320
PGVFVFFDKN GLAYPPENMN                                              1340

SEQ ID NO: 29          moltype = DNA   length = 4026
FEATURE                Location/Qualifiers
source                 1..4026
                       mol_type = other DNA
                       organism = Streptococcus salivarius
SEQUENCE: 29
atgacggacg gtaaatacta ttatgtaaat gaggacggca gccacaaaga gaatttcgca     60
attacggtaa acggtcaact gttgtacttt ggcaaggacg gcgctctgac gagcagcagc    120
acgcacagct tcacgccggg tactacgaat attgtggacg gtttctcgat caacaaccgt    180
gcgtacgata gcagcgaagc gagctttgag ctgatcaacg ttacctgacg gcggattccc    240
tggtatcgcc cggtttctat catcaaggat ggcgtcacgt ggcaggcaag cactgccgag    300
gattttcgtc cgctgttgat ggcctggtgg ccgaacgttg ataccaggt gaactatctg    360
aactatatgt ccaaggtctt taacctggaa gccaagtaca ccagcaccga taaacaggct    420
gatctgaacc gtgctgcaaa ggatatccag gtcaagatcg aacagaagat ccaggcggaa    480
aagagcacgc agtggctgcg tgagactatc tccgcgtttg ttaaacccca gccgcaatgg    540
aacaaagaga ctgagaatta ctccaagggg ggtggcaaga atcatctgca aggcggtgcg    600
ctgttgtacg tgaacgacag ccgtaccccg tgggcgaata gcaattaccg cctgctgaat    660
cgcacggcaa cgaaccagac cggtaccatt aacaagtcgg tgttggacga gcaatccgat    720
ccaaatcaca tgggtggctt cgacttcctg ctggcaaacg atgtggatct gagcaatcct    780
gttgtgcagg ccgagcagct gaatcaaatc cattatctga tgaactgggg cagcattgtt    840
atgggtgaca aagacgcgaa ttttgatggt atccgtgtgg acgccgttga caacgtgaac    900
gctgacatgt tgcagctgta cacgaactac tttcgtgagt attacggcgt caacaaaagc    960
gaagcgcaag cgctggcgca cattagcgtt ctggaagcgt ggagcttgaa cgataaccac   1020
tataacgaca aaaccgatgg tgcggcactg gcgatggaga ataagcaacg tctggccttg   1080
ctgttctctc tggccaagcc gatcaaagat cgtactccga cagtgctaac actgtataac   1140
aatactttca ataccaccca acgtgacttc aagacggatt ggattaacaa ggacggtagc   1200
accgcctaca atgaggatgg caccgcgaaa caatctacca tcggtaagta caatgagaaa   1260
tatggtgatg caagcggtaa ctatgtgttt attcgtgccc atgacaataa cgtccaagac   1320
attattgcgg agatcattaa gaaagaaatc aataagaaga cgatggtttt taccatcagc   1380
gatagcgaaa tgaaacaggc gttcgaaatc tacaacaaag atatgctgag cagcaataag   1440
aaatacactc tgaataacat tccggcagcg tacgccgtga tgctgcaaaa catggagact   1500
atcacccgtg tgtattatgg tgacctgtac accgacgacg tcactatat ggaaaccaag   1560
agcccgtatc atgacaccat tgtgaacctg atgaaaaacc gtatcaagta cgtttctgat   1620
ggccaggccc aacgctccta ttggctgccg accgacggta aaatggacaa tagccgatgtc   1680
gaactgtacc gtactagcga ggtctatacc agcttcgct acggtaagga cattatgacg   1740
gcggatgaca ccgagggtag caagtactcc cgcacgagcg tcaggttac cctggttgtt   1800
aacaaccgga agctgactct gcatgaaagc gccaaactga acgtcgagat gggtaagatc   1860
cacgcaaaacc agaaataccg tgcgctgatt gtgggtaccg ccgatggcat caaaaacttt   1920
acgtctgatg ccgaagcgat cgcggcaggc tactgtaaaag aaacgggacag caatggtgtt   1980
ctgaccttcg gcgcaaatga tatcaaaggt tacgagactt cgatatgag cggtttcgtc   2040
gcagtttggg tgccggtggg tgcgagcgat gatcaggaca tccgcgtggc gccgtcgacg   2100
gaagcgaaga aagaaggtga actgacgctg aaagccacgg aagcgtatga tagccagttg   2160
atttatgaag gcttctccaa tttccagacc attccggatg cagcgaccc gagcgtttat   2220
accaaccgca aaattgctga atgttgat ctgttaagt cctggggtgt cactagcttc   2280
gaaatggctc cgcagtttgt ttcggcgac gacggcacct tcctggatag cgttatccag   2340
aacggttacg cctttgcgga ccgttatgat tggcgatga gcaagaacaa caagtacggt   2400
tctaaagagg atctgcgcga cgcactgaaa gcgctgcaca agctggcat tcaggcaatc   2460
gcggactggg tcccagacca aatctaccaa ctgccaggca agaagtggt tacggcgacg   2520
cgcacggacg gtgcgggtcg caagatcgcg gacgccatca ttgatcatag cctgtatgtt   2580
gctaactcca agagctccgg tcgcgattac caagcgcagt atggtggcga gtttctggca   2640
gagctgaaag cgaagtaccc gaaaatgttc acggaaaaca tgattagcac gggtaagccg   2700
atcgatgaca gcgtcaaact gaagcaatgg aaagccaagt attcaatgg tacgaatgtg   2760
ctggaccgtg gtgtcggtta cgtcctgtcc gacgaggcga ccgcaaata cttcaccgtt   2820
accaaagagg gtaacttcat tccgctgcaa ctgaccggca tgaaaaagc ggtgaccggt   2880
ttcagcaacg acggcaaggg tatcacctac tttggtacga cggtaatca ggccaagagc   2940
gcgttcgtca cctttaacgg caatacgtac tatttcgacg cgcgtggcca tggtcgtg   3000
aacggcgagt atagcccgaa cggcaaagat gtctaccgtt ttctgccaaa tggtattatg   3060
ttgtcgaacg cgtttttatgt cgacgcaaac ggtaatacgt acttgtacaa ctacaagggc   3120
cagatgtaca aggtggtta tacgaaattt gatgtcaccg aaactgataa agatggtaat   3180
gagagcaagg tggtcaagtt tcgttattc accaatgagg gcgtcatggc taagggtctg   3240
accgtcattg acggtagcac ccagtacttt ggtgaggatg gttttcaaac gaaggacaag   3300
```

-continued

```
ctggcgacct ataaaggtaa gacttattac ttcgaggcac acacgggcaa tgcgatcaaa   3360
aacacctggc gtaacatcga cggtaagtgg tatcacttcg atgagaatgg cgttgccgcg   3420
accggtgcac aagtgattaa cggtcaaaaa ctgtatttca acgaggatgg ctcgcaagtg   3480
aagggcggtg ttgttaagaa cgccgacggt acctacagca aatacaaaga gggcagcggt   3540
gagcggtta ccaacgagtt tttcacgacc gacggtaatg tgtggtacta tgctggtgcg   3600
gatggcaaga ctgtgaccgg tgctcaggtc attaatggtc agcacctgta ctttaaagaa   3660
gatggcagcc aggtgaaagg tggtgtggtg aaaaacgcgg acggtacgta cagcaagtat   3720
gacgccgcca ccggtgaacg cttgaccaat gagttcttta ccacgggcga taacaattgg   3780
tactatattg gttctaatgg taagaccgta accggtgaag tcaaaatcgg tgcggacacc   3840
tattactttg ccaaagatgg caaacaggtc aagggccaaa ccgtcaccgc aggcaatggc   3900
cgcatctcct attactacgg cgattctggt aagaaagcaa tcagcacgtg gatcgaaatt   3960
caaccgggta tctatgtcta ttttgataag acgggcatcg cgtacccacc gcgtgtgctg   4020
aattaa                                                              4026

SEQ ID NO: 30          moltype = AA  length = 1341
FEATURE                Location/Qualifiers
source                 1..1341
                       mol_type = protein
                       organism = Streptococcus salivarius
SEQUENCE: 30
MTDGKYYVN  EDGSHKENFA  ITVNGQLLYF  GKDGALTSSS  THSFTPGTTN  IVDGFSINNR    60
AYDSSEASFE LINGYLTADS  WYRPVSIIKD  GVTWQASTAE  DFRPLLMAWW  PNVDTQVNYL   120
NYMSKVFNLE AKYTSDKQA   DLNRAAKDIQ  VKIEQKIQAE  KSTQWLRETI  SAFVKTQPQW   180
NKETENYSKG GGEDHLQGGA LLYVNDSRTP  WANSNYRLLN  RTATNQTGTI  NKSVLDEQSD   240
PNHMGGFDFL LANDVDLSNP VVQAEQLNQI  HYLMNWGSIV  MGDKDANFDG  IRVDAVDNVN   300
ADMLQLYTNY FREYYGVNKS EAQALAHISV  LEAWSLNDNH  YNDKTDGAAL  AMENKQRLAL   360
LFSLAKPIKD RTPAVSPLYN NTFNTTQRDF  KTDWINKDGS  TAYNEDGTAK  QSTIGKYNEK   420
YGDASGNYVF IRAHDNNVQD IIAEIIKKEI  NKKSDGFTIS  DSEMKQAFEI  YNKDMLSSNK   480
KYTLNNIPAA YAVMLQNMET ITRVYYGDLY  TDDGHYMETK  SPYHDTIVNL  MKNRIKYVSG   540
GQAQRSYWLP TDGKMDNSDV ELYRTSEVYT  SVRYGKDIMT  ADDTEGSKYS  RTSGQVTLVV   600
NNPKLTLHES AKLNVEMGKI HANQKYRALI  VGTADGIKNF  TSDAEAIAAG  YVKETDSNGV   660
LTFGANDIKG YETFDMSGFV AVWVPVGASD  DQDIRVAPST  EAKKEGELTL  KATEAYDSQL   720
IYEGFSNFQT IPDGSDPSVY TNRKIAENVD  LFKSWGVTSF  EMAPQFVSAD  DGTFLDSVIQ   780
NGYAFADRYD LAMSKNNKYG SKEDLRDALK  ALHKAGIQAI  YNDAVPDQIYQ LPGKEVVTAT   840
RTDGAGRKIA DAIIDHSLYV ANSKSSGRDY  QAQYGGEFLA  ELKAKYPKMF  TENMISTGKP   900
IDDSVKLKQW KAKYFNGTNV LDRGVGYVLS  DEATGKYFTV  TKEGNFIPLQ  LTGNEKAVTG   960
FSNDGKGITY FGTSGNQAKS AFVTFNGNTY  YFDARGHMVT  NGEYSPNGKD  VYRFLPNGIM  1020
LSNAFYVDAN GNTYLYNYKG QMYKGGYTKF  DVTETDKDGN  ESKVVKFRYF  TNEGVMAKGL  1080
TVIDGSTQYF GEDGFQTKDK LATYKGKTYY  FEAHTGNAIK  NTWRNIDGKW  YHFDENGVAA  1140
TGAQVINGQK LYFNEDGSQV KGGVVKNADG  TYSKYKEGSG  ELVTNEFFTT  DGNVWYYAGA  1200
DGKTVTGAQV INGQHLYFKE DGSQVKGGVV  KNADGTYSKY  DAATGERLTN  EFFTTGDNNW  1260
YYIGSNGKTV TGEVKIGADT YYFAKDGKQV  KGQTVTAGNG  RISYYYGDSG  KKAISTWIEI  1320
QPGIYVYFDK TGIAYPPRVL N                                              1341

SEQ ID NO: 31          moltype =    length =
SEQUENCE: 31
000

SEQ ID NO: 32          moltype =    length =
SEQUENCE: 32
000

SEQ ID NO: 33          moltype = DNA  length = 4026
FEATURE                Location/Qualifiers
source                 1..4026
                       mol_type = other DNA
                       organism = Streptococcus salivarius
SEQUENCE: 33
atgatcgacg gcaaatacta ctatgtaaac gaggacggca gccacaaaga gaatttcgcg     60
attacggtaa acggtcagct gctgtacttt ggtaaggacg gtgctctgac gagcagctcc    120
acgtacagct ttaccccggg tacgaccaat attgtcgatg gcttcagcat taacaaccgt    180
gcgtatgaca gcagcgaggc atcctttgag ctgatcgatg gttatttgac cgcggatagc    240
tggtatcgtc cggtgagcat cattaaggac ggcgttacgt ggcaggcctc gaccgcagaa    300
gattttcgtc cgctgctgat ggcttggtgg ccagatgtca acacccaggt gaattatctg    360
aattacatgt ccaaggtttt caacctggat gcaaagtaca ccagcaccga caagcaggaa    420
accctgaacg tggctgcgaa agatatccaa gtcaagattg agcaaaagat tcaggcgag    480
aaatctaccc agtggctgcg tgaaacgatt agcgcgtttg ttaaaactca gccgcaatgg    540
aataaagaaa cggaaaacta ttccaagggt ggtggcgagg accatctgca aggcggtgcc    600
ctgttgtacg ttaacgattc gcgcaccccg tgggcgaact cgaactgtga ac              660
catccgcta ccaatcaaaa aggcactatt gacaaatctg tcctggacga gcagagcgac    720
ccgaaccaca tgggcggttt cgattttctg ctggcgaacg acgtcgacct gagcaacccg    780
gtggtgcagg ccgaacaact gaaccagatt cactacctga tgaattgggg tagcatcgtg    840
atgggtgata aagatgcgaa cttttgacgg attcgtgtcg atgcggtcga taacgtggac    900
gccgatgtg tgcagctgta cacgaactac tttcgtgagt actacggtat taacgaagac    960
gaagcaaatg ccctggcgca tatcagcgtt ctggaagcgt ggagcctgaa tgacaatcac   1020
tataacgata gacggacgg tgcggccctg gcaatggaga ataaaacg tctggcgctg    1080
ctgttcagcc tggcgaaacc gatcaaagag cgtacgccgg ctgtgagccc actgtataac   1140
aacaccttca atactacgca gcgtgacgag aaaacggact ggattaacaa agacggtagc   1200
aaagcgtata cgaggatgg taccgtcaag caatcgacca ttggtaagta caatgagaag   1260
```

```
tatggcgacg caagcggtaa ttacgtgttc attcgtgccc acgacaacaa tgttcaagac 1320
atcatcgccg aaatcatcaa gaaagagatc aaccctaaga gcgacggttt caccatcacc 1380
gacgcagaga tgaagaaggc cttttgaaatc tacaacaagg acatgttgag cagcgataag 1440
aagtatactc tgaacaacat tccggctgcg tacgcggtga tgttcagaa tatggaaacc 1500
atcacgcgtg tttactatgg tgatctgtat accgataagt gcaactacgt ggaaacgaaa 1560
agcccgtact atgacaccat tgttaatctg atgaagaatc gcatcaagta tgtgtctggc 1620
ggtcaagcgc agcgttctta ctggctgccg accgatggta agatggacaa tagcgatgtg 1680
gaactgtacc gcaccaacga ggtatacgct tctgtgcgct atggtaaaga cattatgacc 1740
gccgatgata ccgagggttc caagtactcc cgtacgagcg gccaagttac cttggtggca 1800
aacaacccga aattgaccct ggaccaaagc gcgaaactga aagtggagat gggtaagatc 1860
cacgcaaatc aaaagtaccg tgcactgatt gtcggtaccg ccgacggtat caagaatttc 1920
accagcgatg cggatgcgat tgcagcaggc tatgttaaag agactgatag caatggtgtg 1980
ctgacgtttg gtgcgaacga cattaaaggc tatgaaacgt ttgacatgag cggtttcgtt 2040
gcggttgacg tgcctgtggg tgctagcgat gatcaggata tccgtgtcgc gccgagcacc 2100
gaggcaaaga aagaaggtga gctgacgttg aaagcgaccg aggcctatga cagccagttg 2160
atttacgaag gtttcagcaa tttccaaacc attccagacg gttccgatcc gagcgtctac 2220
accaatcgca aaatcgcgga aaacgttgat ctgttcaaaa gctggggtgt gaccagcttc 2280
gaaatggcac cgcaattcgt tagcgcggac gatggtacgt tcttggacag tgttatccaa 2340
aatggctatg cgttcgccga tcgttatgac ttggcgatga gcaaaaacaa caaatacggc 2400
agcaaagagg atctgcgcga cgccctgaaa gcgctgcata agcgggtat tcaagccatc 2460
gctgactggg ttccggacca gatctaccag ctgccgggta agaagtcgt taccgcgacc 2520
cgcaccgatg gcgctggccg taagatcgcg gatgcaatta tcgatcatag cttgtatgtg 2580
gccaatacta aaagctccgg taaggattac caggcgaaat atggtggtga atttctggct 2640
gagctgaagg ccaaataccc ggagatgttc aaggtcaaca tgattagcac cggcaaacct 2700
attgatgact ctgtcaaatt gaaacaatgg aaggcagagt atttcaatgg cactaacgtc 2760
ctggaacgtg gtgttggtta cgtgctgagc gacgaggcga ccgtaaaata cttcaccgtt 2820
acgaaggacg gcaatttcat cccgctgcaa ctgaccggta atgagaaggt tgtgacgggt 2880
ttttctaatg acggtaaggg cattacctac ttcggtaccc cgggtaccca ggcaaagagc 2940
gcattcgtga cgtttaacgg taacacctac tactttgatg cacgcggcca catggtgacg 3000
aacggcgagt acagcccgaa cggcaaggat gtttatcgct tcctgccgaa tggcatcatg 3060
ctgtccaatg cgttttacgt cgatgcaaat ggtaatactt acctgtacaa cagcaagggt 3120
cagatgtata agggcggtta taccaagttc gacttactg aaacggacaa ggacggtaaa 3180
gagagcaaag tagtgaagtt tcgttatttc acgaacgaag cgtcatggc gaaaggtgtc 3240
accgttattg atggctttac ccagtatttc ggtgaagatg gctttcaagc gaaggacaag 3300
ctggtgaccct ttaagggcaa aacctactat tttgacgcgc acacgggcaa cgccatcaag 3360
aacacctggc gtaatatcga cggtaagtgg tatcattttg atgcgaacgg tgtggcggcg 3420
accggcgcac aggtcattaa tggtcaaaaa ctgtacttta tgaggacgg tagccaagtc 3480
aaaggtggcg tcgtcaagaa tgcagatggc acctatagca aatacaaaga gggctccggt 3540
gagctggtta ccaacgagtt cttttaccacg gatggtaacg tctggtacta tgctggtgcg 3600
aatggcaaga ccgttaccgg tgcacaggtt atcaacggcc agcacctgta cttcaatgcg 3660
gatggctctc aagtgaaggg cggtgtcgtc aaaaacgcgg acgtacgta ctccaaatac 3720
gatgccgcga ccggtgaacg tctgaccaat gagtttttca cgactggtga caacaattgg 3780
tactcatcg gcgccaacgg taagacggtt acgggcgaga tgaaaattgg cgacgatacg 3840
tactacttcg caaaagatgg taaacaggtg aaaggtcaga cggtttccgc tggtaatggc 3900
cgcatcagct actattacgg tgactctggt aaacgtgcgg ttagcacgtg ggttgaaatt 3960
caaccggggcg tgtatgtcta ttttgataag aatggcctgg catatccacc gcgcgttttg 4020
aattaa                                                              4026

SEQ ID NO: 34         moltype = AA  length = 1341
FEATURE               Location/Qualifiers
source                1..1341
                      mol_type = protein
                      organism = Streptococcus salivarius
SEQUENCE: 34
MIDGKYYYVN EDGSHKENFA ITVNGQLLYF GKDGALTSSS TYSFTPGTTN IVDGFSINNR   60
AYDSSEASFE LIDGYLTADS WYRPASIIKD GVTWQASTAE DFRPLLMAWW PNVDTQVNYL  120
NYMSKVFNLD AKYTSTDKQE TLNVAAKDIQ VKIEQKIQAE KSTQWLRETI SAFVKTQPQW  180
NKETENYSKG GGEDHLQGGA LLYVNDSRTP WANSNYRLLN HTATNQKGTI DKSVLDEQSD  240
PNHMGGFDFL LANDVDLSNP VVQAEQLNQI HYLMNWGSIV MGDKDANFDG IRVDAVDNVD  300
ADMLQLYTNY FREYYGVNKS EANALAHISV LEAWSLNDNH YNDKTDGAAL AMENKQRLAL  360
LFSLAKPIKE RTPAVSPLYN NTFNTTQRDE KTDWINKDGS KAYNEDGTVK QSTIGKYNEK  420
YGDASGNYVF IRAHDNNVQD IIAEIIKKEI NPKSDGFTIT DAEMKKAFEI YNKDMLSSDK  480
KYTLNNIPAA YAVMLQNMET ITRVYYGDLY TDNGNYMETK SPYYDTIVNL MKNRIKYVSG  540
GQAQRSYWLP TDGKMDNSDV ELYRTNEVYA SVRYGKDIMT ADDTEGSKYS RTSGQVTLVA  600
NNPKLTLDQS AKLKVEMGKI HANQKYRALI VGTADGIKNF TSDADAIAAG YVKETDSNGV  660
LTFGANDIKG YETFDMSGFV AVWVPVGASD DQDIRVAPST EAKKEGELTL KATEAYDSQL  720
IYEGFSNFQT IPDGSDPSVY TNRKIAENVD LFKSWGVTSF EMAPQFVSAD DGTFLDSVIQ  780
NGYAFADRYD LAMSKNNKYG SKEDLRDALK ALHKAGIQAI ADWVPDQIYQ LPGKEVVTAT  840
RTDGAGRKIA DAIIDHSLYV ANTKSSGKDY QAKYGGEFLA ELKAKYPEMF KVNMISTGKP  900
IDDSVKLQW KAEYFNGTNV LERGVGYVLS DEATGKYFTV TKDGNFIPLQ LTGNEKVVTG  960
FSNDGKGITY FGTSGTQAKS AFVTFNGNTY YFDARGHMVT NGEYSPNGKD VYRFLPNGIM 1020
LSNAFYVDAN GNTYLYNSKG QMYKGGYTKF DVTETDKDGK ESKVVKFRYF TNEGVMAKGV 1080
TVIDGFTQYF GEDGFQAKDK LVTFKGKTYY FDAHTGNAIK NTWRNIDGKW YHFDANGVAA 1140
TGAQVINGQK LYFNEDGSQV KGGVVKNADG TYSKYKEGSG ELVTNEFFTT DGNVWYYAGA 1200
NGKTVTGAQV INGQHLYFNA DGSQVKGGVV KNADGTYSKY DAATGERLTN EFFTTGDNNW 1260
YYIGANGKTV TGEVKIGDDT YYFAKDGKQV KGQTVSAGNG RISYYYGDSG KRAVSTWVEI 1320
QPGVYVYFDK NGLAYPPRVL N                                            1341

SEQ ID NO: 35         moltype =     length =
```

SEQUENCE: 35
000

SEQ ID NO: 36     moltype =    length =
SEQUENCE: 36
000

SEQ ID NO: 37     moltype =    length =
SEQUENCE: 37
000

SEQ ID NO: 38     moltype =    length =
SEQUENCE: 38
000

SEQ ID NO: 39     moltype =    length =
SEQUENCE: 39
000

SEQ ID NO: 40     moltype =    length =
SEQUENCE: 40
000

SEQ ID NO: 41     moltype =    length =
SEQUENCE: 41
000

SEQ ID NO: 42     moltype =    length =
SEQUENCE: 42
000

SEQ ID NO: 43     moltype =    length =
SEQUENCE: 43
000

SEQ ID NO: 44     moltype =    length =
SEQUENCE: 44
000

SEQ ID NO: 45     moltype =    length =
SEQUENCE: 45
000

SEQ ID NO: 46     moltype =    length =
SEQUENCE: 46
000

SEQ ID NO: 47     moltype =    length =
SEQUENCE: 47
000

SEQ ID NO: 48     moltype =    length =
SEQUENCE: 48
000

SEQ ID NO: 49     moltype =    length =
SEQUENCE: 49
000

SEQ ID NO: 50     moltype =    length =
SEQUENCE: 50
000

SEQ ID NO: 51     moltype =    length =
SEQUENCE: 51
000

SEQ ID NO: 52     moltype =    length =
SEQUENCE: 52
000

SEQ ID NO: 53     moltype =    length =
SEQUENCE: 53
000

SEQ ID NO: 54     moltype =    length =
SEQUENCE: 54
000

| SEQ ID NO: 55 | moltype = length = |
| SEQUENCE: 55 | |
| 000 | |

| SEQ ID NO: 56 | moltype = length = |
| SEQUENCE: 56 | |
| 000 | |

| SEQ ID NO: 57 | moltype = length = |
| SEQUENCE: 57 | |
| 000 | |

| SEQ ID NO: 58 | moltype = length = |
| SEQUENCE: 58 | |
| 000 | |

| SEQ ID NO: 59 | moltype = AA length = 1242 |
| FEATURE | Location/Qualifiers |
| source | 1..1242 |
| | mol_type = protein |
| | organism = Streptococcus sp. |
| SEQUENCE: 59 | |

```
MINGKEYYVE DDGTVRKNYV LERNGGSQYF NAETGELSNQ KDYRFDKNGG TGSAADSTTN    60
TNVTVNGDKN AFYGTTEKDI ELVDGYFTAN TWYRPKEILK DGKEWTASTE NDKRPLLTVW   120
WPSKAIQASY LNYMREEGLG TNQTFTSYSS QTQMDQAALE VQKRIEERIA REGNTDWLRT   180
TIKNFVKTQP GWNSTSENLD NSDHLQGGAL LYNNSNRTSY ANSDYRLLNR TPTQQDGTRR   240
YFKDNSSGGF EFLLANDIDN SNPAVQAEQL NWLHYIMNIG SLTGGSEDEN FDGVRVDAVD   300
NVNADLLQIA SDYFKAKYGV EKSEEEAIKH LSILEAWSHN DAYYNEDTKG AQLPMDDPLR   360
LAMVFSFLRP IGNRSGLEPL ITNSLNDRSE SKKNTKRMAN YTFVRAHDSE VQSVIGQIIK   420
NEINPQSTGN TFTLDEMKKA FKIYNADMRS ANKRYTQYNI PSAYAFMLTN KDTVPRVYYG   480
DLYTDDGQYM AQKSPYHDAI STLLQARIRY AAGGQDMKMS YVGSGNTNGW DASGVLTSVR   540
YGKGANNASD AGTAETRNQG MAVILSNQPA LRLNSNLTIN MGAAHRNQAY RPLLLTTSNG   600
VASYLNDGDA NGIVKYTDAN GYLTFNPGEI SGVRNAQVDG YLAVWVPLGA SENQDVRVAA   660
SKSKNSSGLV YDSSAALDSQ VIYEGFSNFQ DFVQDPSQYT NKKIAENANL FKSWGITSFE   720
FAPQYVSSDD GTFLDSVIQN GYAFSDRYDI GMSKDNKYGS LADLKAALKS LHAVGISAIA   780
DWVPDQIYNL PGDEVVTATR VNNYGETKDG AIIDHSLYVA KTRTFGNDYQ GKYGGAYLDE   840
LKRLYPQFFD RVQISTGKRL TTDEKITKWS AKYMNGTNIL DRGSEYVLKN GLSGYYGTNG   900
GKVSLPKVVG SNQSTNNNNQ NGDGSGRFEK SWGSVYYRYN DGRARNAFI KDNDGNVYYF   960
DNTGRMAIGE KTIDGKQYFF LANGVQLRDG YRQNRRGQVF YYDENGIMSQ TGKPSPKPEP  1020
KPDNNTFSRN QFIQIGNNVW AYYDGNGKRV IGRQNINGQE LFFDNNGVQV KGRTAQVDGV  1080
TRYFDANSGE MARNRFAEVE PGVWAYFNND GAAVTGSQNI NGQTLYFDQN GHQVKGALVT  1140
VDGNLRYYDA NSGDLYRNRF QEVNGSWYYF DGNGNAVKGM VNINGQNLLF DNDGKQVKGH  1200
LVRVNGVIRY YDPNSGEMAV NRWVEISSGW WVYFDGEGRG QI                    1242
```

| SEQ ID NO: 60 | moltype = AA length = 1518 |
| FEATURE | Location/Qualifiers |
| source | 1..1518 |
| | mol_type = protein |
| | organism = Streptococcus salivarius |
| SEQUENCE: 60 | |

```
MENKIHYKLH KVKKQWVTIA VASVALATVL GGLSVTTSSV SADETQDKTV TQSNSGTTAS    60
LVTSPEATKE ADKRTNTKEA DVLTPAKETN AVETATTTNT QATAEAATTA TTADVAVAAV   120
PNKEAVTTTD APAVTTEKAE EQPATVKAEV VNTEVKAPEA ALKDSEVEAA LSLKNIKNID   180
GKYYVNEDG SHKENFAITV NGQLLYFGKD GALTSSSTYS FTPGTTNIVD GFSINNRAYD   240
SSEASFELID GYLTADSWYR PASIIKDGVT WQASTAEDFR PLLMAWWPNV DTQVNYLNYM   300
SKVFNLDAKY SSTDKQETLK VAAKDIQIKI EQKIQAEKST QWLRETISAF VKTQPQWNKE   360
TENYSKGGGE DHLQGGALLY VNDSRTPWAN SDYRRLNRTA TNQTGTIDKS ILDEQSDPNH   420
MGGFDFLLAN DVDLSNPVVQ AEQLNQIHYL MNWGSIVMGD KDANFDGIRV DAVDNVDADM   480
LQLYTNYFRE YYGVNKSEAN ALAHISVLEA WSLNDNHYND KTDGAALAME NKQRLALLFS   540
LAKPIKERTP AVSPLYNNTF NTTQRDEKTD WINKDGSKAY NEDGTVKQST IGKYNEKYGD   600
ASGNYVFIRA HDNNVQDIIA EIIKKEINPK SDGFTITDAE MKQAFEIYNK DMLSSDKKYT   660
LNNIPAAYAV MLQNMETITR VYYGDLYTDD GHYMETKSPY YDTIVNLMKS RIKYVSGGQA   720
QRSYWLPTDG KMDNSDVELY RTNEVYTSVR YGKDIMTAND TEGSKYSRTS GQVTLVANNP   780
KLNLDQSAKL NVEMGKIHAN QKYRALIVGT ADGIKNFTSD ADAIAAGYVK ETDSNGVLTF   840
GANDIKGYET FDMSGFVAVW VPVGASDNQD IRVAPSTEAK KEGELTLKAT EAYDSQLIYE   900
GFSNFQTIPD GSDPSVYTNR KIAENVDLFK SWGVTSFEMA PQFVSADDGT FLDSVIQNGY   960
AFADRYDLAM SKNNKYGSKE DLRDALKALH KAGIQAIADW VPDQIYQLPG KEVVTATRTD  1020
GAGRKIADAI IDHSLYVANS KSSGKDYQAK YGGEFLAELK AKYPEMFKVN MISTGKPIDD  1080
SVKLKQWKAE YFNGTNVLER GVGYVLSDEA TGKYFTVTKE GNFIPLQLTG KEKVITGFSS  1140
DGKGITYFGT SGTQAKSAFV TFNGNTYYFD ARGHMVTNSE YSPNGKDVYR FLPNGIMLSN  1200
APYIDANGNT YLYNSKGQMY KGGYTKFDVS ETDKDGKESK VVKFRYFTNE GVMAKGVTVI  1260
DGFTQYFGED GFQAKDKLVT FKGKTYYFDA HTGNGIKDTW RNINGKWYYF DANGVAATGA  1320
QVINGQKLYF NEDGSQVKGG VVKNADGTYS KYKEGFGELV TNEFFTTDGN VWYYAGANGK  1380
TVTGAQVING QHLYFNADGS QVKGGVVKNA DGTYSKYNAS TGEERLTNEFF TTGDNNWYYI  1440
GANGKSVTGE VKIGDDTYFF AKDGKQVKGQ TVSAGNGRIS YYYGDSGKRA VSTWIEIQPG  1500
VYVYFDKNGL AYPPRVLN                                              1518
```

| SEQ ID NO: 61 | moltype = AA length = 1528 |
| FEATURE | Location/Qualifiers |

```
source                  1..1528
                        mol_type = protein
                        organism = Streptococcus salivarius
SEQUENCE: 61
MTNKITGKII MENKVHYKLH KVKKQWVTIA VASAALATVV GGLSATTSSV SADETQDKIV    60
TQPNLDTTAD LVTSTEATKE VDKRTNTKEA DVLTPAKETN AVETATTTNT QATAEAATTA   120
TTSDVAVAAV PNKEAVVTTD APAVTTEKAE EQPATVKAEV VNTEVKAPQA ALKDSEVEAA   180
LSLKNIKYTD GKYYYVNEDG SHKENFAITV NGQLLYFGKD GALTSSSTHS FTPGTTNIVD   240
GFSINNRAYD SSEASFELIN GYLTADSWYR PVSIIKDGVT WQASTAEDFR PLLMAWWPNV   300
DTQVNYLNYM SKVFNLEAKY TSTDKQADLN RAAKDIQVKI EQKIQAEKST QWLRETISAF   360
VKTQPQWNKE TENYSKGGGE DHLQGGALLY VNDSRTPWAN SNYRLLNRTA TNQTGTINKS   420
VLDEQSDPNH MGGFDFLLAN DVDLSNPVVQ AEQLNQIHYL MNWGSIVMGD KDANFDGIRV   480
DAVDNVNADM LQLYTNYFRE YYGVNKSEAQ ALAHISVLEA WSLNDNHYND KTDGAALAME   540
NKQRLALLFS LAKPIKDRTP AVSPLYNNTF NTTQRDFKTD WINKDGSTAY NEDGTAKQST   600
IGKYNEKYGD ASGNYVFIRA HDNNVQDIIA EIIKKEINKK SDGFTISDSE MKQAFEIYNK   660
DMLSSNKKYT LNNIPAAYAV MLQNMETITR VYYGDLYTDD GHYMETKSPY HDTIVNLMKN   720
RIKYVSGGQA QRSYWLPTDG KMDNSDVELY RTSEVYTSVR YGKDIMTADD TEGSKYSRTS   780
GQVTLVVNNP KLTLHESAKL NVEMGKIHAN QKYRALIVGT ADGIKNFTSD AEAIAAGYVK   840
ETDSNGVLTF GANDIKGYET FDMSGFVAVW VPVGASDDQD IRVAPSTEAK KEGELTLKAT   900
EAYDSQLIYE GFSNFQTIPD GSDPSVYTNR KIAENVDLFK SWGVTSFEMA PQFVSADDGT   960
FLDSVIQNGY AFADRYDLAM SKNNKYGSKE DLRDALKALH KAGIQAIADW VPDQIYQLPG  1020
KEVVTATRTD GAGRKIADAI IDHSLYVANS KSSGRDYQAK YGGEFLAELK AKYPKMFTEN  1080
MISTGKPIDD SVKLKQWKAK YFNGTNVLDR GVGYVLSDEA TGKYFTVTKE GNFIPLQLTG  1140
NEKAVTGFSN DGKGITYFGT SGNQAKSAFV TFNGNTYYFD ARGHMVTNGE YSPNGKDVYR  1200
FLPNGIMLSN AFYVDANGNT YLYNYKGQMY KGGYTKFDVT ETDKDGNESK VVKFRYFTNE  1260
GVMAKGLTVI DGSTQYFGED GFQTKDKLAT YKGKTYYFEA HTGNAIKNTW RNIDGKWYHF  1320
DENGVAATGA QVINGQKLYF NEDGSQVKGG VVKNADGTYS KYKEGSGELV TNEFFTTDGN  1380
VWYYAGADGK TVTGAQVING QHLYFKEDGS QVKGGVVKNA DGTYSKYDAA TGERLTNEFF  1440
TTGDNNWYYI GSNGKTVTGE VKIGADTYYF AKDGKQVKGQ TVTAGNGRIS YYYGDSGKKA  1500
ISTWIEIQPG IYVYFDKTGI AYPPRVLN                                    1528

SEQ ID NO: 62           moltype = AA  length = 1518
FEATURE                 Location/Qualifiers
source                  1..1518
                        mol_type = protein
                        organism = Streptococcus salivarius
SEQUENCE: 62
MENKIHYKLH KVKKQWVTIA VASVALATVL GGLSVTTSSV SADETQDKTV TQSNSGTTAS    60
LVTSPEATKE ADKRTNTKEA DVLTPAKETN AVETATTTNT QATAEAATTA TTADVAVAAV   120
PNKEAVVTTD APAVTTEKAE EQPATVKAEV VNTEVKAPEA ALKDSEVEAA LSLKNIKNID   180
GKYYYVNEDG SHKENFAITV NGQLLYFGKD GALTSSSTYS FTPGTTNIVD GFSINNRAYD   240
SSEASFELID GYLTADSWYR PASIIKDGVT WQASTAEDFR PLLMAWWPNV DTQVNYLNYM   300
SKVFNLDAKY SSTDKQETLK VAAKDIQIKI EQKIQAEKST QWLRETISAF VKTQPQWNKE   360
TENYSKGGGE DHLQGGALLY VNDSRTPWAN SDYRRLNRTA TNQTGTIDKS ILDEQSDPNH   420
MGGFDFLLAN DVDLSNPVVQ AEQLNQIHYL MNWGSIVMGD KDANFDGIRV DAVDNVDADM   480
LQLYTNYFRE YYGVNKSEAN ALAHISVLEA WSLNDNHYND KTDGAALAME NKQRLALLFS   540
LAKPIKERTP AVSPLYNNTF NTTQRDEKTD WINKDGTVKQST IGKYNEKYGD             600
ASGNYVFIRA HDNNVQDIIA EIIKKEINPK SDGFTITDAE MKQAFEIYNK DMLSSDKKYT   660
LNNIPAAYAV MLQNMETITR VYYGDLYTDD GHYMETKSPY YDTIVNLMKS RIKYVSGGQA   720
QRSYWLPTDG KMDNSDVELY RTNEVYTSVR YGKDIMTAND TEGSKYSRTS GQVTLVANNP   780
KLTLDQSAKL NVEMGKIHAN QKYRALIVGT ADGIKNFTSD ADAIAAGYVK ETDSNGVLTF   840
GANDIKGYET FDMSGFVAVW VPVGASDDQD IRVAPSTEAK KEGELTLKAT EAYDSQLIYE   900
GFSNFQTIPD GSDPSVYTNR KIAENVDLFK SWGVTSFEMA PQFVSADDGT FLDSVIQNGY   960
AFADRYDLAM SKNNKYGSKE DLRDALKALH KAGIQAIADW VPDQIYQLPG KEVVTATRTD  1020
GAGRKIADAI IDHSLYVANT KSSGKDYQAK YGGEFLAELK AKYPEMFKVN MISTGKPIDD  1080
SVKLKQWKAE YFNGTNVLER GVGYVLSDEA TGKYFTVTKD GNFIPLQLTG NEKVVTGFSN  1140
DGKGITYFGT SGTQAKSAFV TFNGNTYYFD ARGHMVTNGE YSPNGKDVYR FLPNGIMLSN  1200
AFYVDANGNT YLYNSKGQMY KGGYTKFDVT ETDKDGKESK VVKFRYFTNE GVMAKGVTVI  1260
DGFTQYFGED GFQAKDKLVT FKGKTYYFDA HTGNAIKDTW RNIDGKWYHF DANGVAATGA  1320
QVINGQKLYF NEDGSQVKGG VVKNADGTYS KYKEGSGELV TNEFFTTDGN VWYYAGANGK  1380
TVTGAQVING QHLYFNADGS QVKGGVVKNA DGTYSKYDAS TGERLTNEFF TTGDNNWYYI  1440
GANGKSVTGE VKIGDDTYFF AKDGKQVKGQ TVSAGNGRIS YYYGDSGKRA VSTWIEIQPG  1500
VYVYFDKNGI AYPPRVLN                                                1518

SEQ ID NO: 63           moltype = AA  length = 1431
FEATURE                 Location/Qualifiers
source                  1..1431
                        mol_type = protein
                        organism = Streptococcus salivarius
SEQUENCE: 63
MTKETNTVDA ATTTNTQAAA DAATKTADAA VTALPNKEAV VTTDAPAVTT EKAAEQPATV    60
KSEVVNTEVK APEAALKDSE VEAALSLKNI KNIDGKYYYV NKDGSHKENF AITVNGQLLY   120
FGKDGALTSS STYSFTQGTT NIVDGFSKNN RAYDSSEASF ELIDGYLTAD SWYRPVSIIK   180
DGVTWQASTK EDFRPLLMAW WPNVDTQVNY LNYMSKVFNL DAKYTSTDKQ VDLNRAAKDI   240
QVKIEQKIQA EKSTQWLREA ISAFVKTQPQ WNKETENFSK GGGEDHLQGG ALLYVNDPRT   300
PWANSNYRLL NRTATNQTGT IDKSVLDEQS DPNHMGGFDF LLANDVDLSN PVVQAEQLNQ   360
IHYLMNWGSI VMGDKDANFD GIRVDAVDNV DADMLQLYTN YFREYYGVNK SEANALAHIS   420
VLEAWSLNDN HYNDKTDGAA LAMENKQRLA LLFSLAKPIK ERTPAVSPLY NNTFNTTQRD   480
EKTDWINKDG SKAYNEDGTV KQSTIGKYNE KYGDASGNYV FIRAHDNNVQ DIIAEIIKKE   540
```

```
INPKSDGFTI TDAEMKKAFE IYNKDMLSSD KKYTLNNIPA AYAVMLQNME TITRVYYGDL   600
YTDDGHYMET KSPYYDTIVN LMKNRIKYVS GGQAQRSYWL PTDGKMDKSD VELYRTNEVY   660
TSVRYGKDIM TADDTQGSKY SRTSGQVTLV VNNPKLSLDK SAKLDVEMGK IHANQKYRAL   720
IVGTPNGIKN FTSDAEAIAA GYVKETDNGG VLTFGANDIK GYETFDMSGF VAVWVPVGAS   780
DDQDIRVAAS TAAKKEGELT LKATEAYDSQ LIYEGFSNPQ TIPDGSDPSV YTNRKIAENV   840
DLFKSWGVTS FEMAPQFVSA DDGTFLDSVI QNGYAFADRY DLAMSKNNKY GSKEDLRNAL   900
KALHKAGIQA IADWVPDQIY QLPGKEVVTA TRTDGAGRKI SDAIIDHSLY VANSKSSGKD   960
YQAKYGGEFL AELKAKYPEM FKVNMISTGK PIDDSVKLKQ WKAEYFNGTN VLDRGVGYVL  1020
SDEATGKYFT VTKEGNFIPL QLKGNEKVIT GFSSDGKGIT YFGTSGNQAK SAFVTFNGNT  1080
YYFDARGHMV TNGEYSPNGK DVYRFLPNGI MLSNAFYVDG NGNTYLYNSK GQMYKGGYSK  1140
FDVTETKDGK ESKVVKFRYF TNEGVMAKGV TVVDGFTQYF NEDGIQSKDE LVTYNGKTYY  1200
FEAHTGNAIK NTWRNIKGKW YHFDANGVAA TGAQVINGQH LYFNEDGSQV KGGVVKNADG  1260
TFSKYKDGSG DLVVNEFFTT GDNVWYYAGA NGKTVTGAQV INGQHLFFKE DGSQVKGDFV  1320
KNSDGTYSKY DAASGERLTN EFFTTGDNHW YYIGANGKTV TGEVKIGDDT YFFAKDGKQL  1380
KGQIVTTRSG RISYYFGDSG KKAISTWVEI QPGVFVFFDK NGLAYPPENM N           1431

SEQ ID NO: 64              moltype = AA  length = 1532
FEATURE                    Location/Qualifiers
REGION                     1..1532
                           note = unknown Streptococcus sp. C150
source                     1..1532
                           mol_type = protein
                           organism = unidentified
SEQUENCE: 64
MENKVHYKLH KVKKQWVTIA VASAALATVV GGLSATTSSV SADETQDKTV TQPNSDTTAD    60
LVTSTEATKE VDKRTNTKEA DVLTPAKETN TVETAATTNT QATAEAAKTA TTTNTQATAE   120
VAKTATTADV AVAAVPNKEA VVTTDAPAVT TEKAEEQPAT VKAEVVNTEV KAPEAALKDS   180
EVEAALSLKN IKNIDKYYYV VNEDGSHKEN FAITVNGQLL YFGKDGALTS SSTYSFTQGT   240
TNIVDGFSIN NRAYDSSEAS FELIDGYLTA DSWYRPASII KDGVTWQAST AEDFRPLLMA   300
WWPNVDTQVN YLNYMSKVFN LDAKYSSTDK QETLKVAAKD IQIKIEQKIQ AEKSTQWLRE   360
TISAFVKTQP QWNKETENYS KGGGEDHLQG GALLYVNDSR TPWANSNYRL LNRTATNQTG   420
TIDKSILDEQ SDPNHMGGFD FLLANDVDLS NPVVQAEQLN QIHYLMNWGS IVMGDKDANF   480
DGIRVDAVDN VDADMLQLYT NYFREYYGVN KSEANALAHI SVLEAWSLND NHYNDKTDVA   540
ALAMENKQRL ALLFSLAKPI KERTPAVSPL YNNTFNTTQR DEKTDWINKD GSKAYNEDGT   600
VKKSTIGKYN EKYGDASGNY VFIRAHDNNV QDIIAEIIKK EINEKSDGFT ITDSEMKRAF   660
EIYNKDMLSN DKKYTLNNIP AAYAVMLQNM ETITRVYYGD LYTDDGNYME AKSPYYDTIV   720
NLMKSRIKYV SGGQAQRSYW LPTDKMDKS DVELYRTNEV YTSVRYGKDI MTADDTQGSK   780
YSRTSGQVTL VVNNPKLTLD QSAKLNVVMG KIHANQKYRA LIVGTPNGIK NFTSDAEAIA   840
AGYVKETDGN GVLTFGANDI KGYETFDMSG FVAVWVPVGA SDDQDIRVAA STAAKKEGEL   900
TLKATEAYDS QLIYEGFSNF QTIPDGSDPS VYTNRKIAEN VDLFKSWGVT SFEMAPQFVS   960
ADDGTFLDSV IQNGYAFADR YDLAMSKNNK YGSKEDLRNA LKALHKAGIQ AIADWVPDQI  1020
YQLPGKEVVT ATRTDGAGRK ISDAIIDHSL YVANSKSSGK DYQAKYGGEF LAELKAKYPE  1080
MFKVNMISTG KPIDDSVKLK QWKAEYFNGT NVLDRGVGYV LSDEATGKYF TVTKEGNFIP  1140
LQLKGNKKVI TGFSSDGKGI TYFGTSGNQA KSAFVTFNGN TYYFDARGHM VTNGEYSPNG  1200
KDVYRFLPNG IMLSNAFYVD GNGNTYLYNS KGQMYKGGYS KFDVTETKDG KESKVVKFRY  1260
FTNEGVMAKG VTVVDGFTQY FNEDGIQSKD ELVTYNGKTY YFEAHTGNAI KNTWRNIKGK  1320
WYHFDANGVA ATGAQVINGQ HLYFNEDGSQ VKGSIVKNAD GTFSKYKDSS GDLVVNEFFT  1380
TGDNVWYYAG ANGKTVTGAQ VINGQHLFFK EDGSQVKGDF VKNSDGTYSK YDAASGERLT  1440
NEFFTTGDNH WYYIGANGKT VTGEVKIGDD TYFFAKDGKQ LKGQIVTTRS GRISYYFGDS  1500
GKKAISTWVE IQPGVFVFFD KNGLAYPPEN MN                                1532

SEQ ID NO: 65              moltype = AA  length = 1341
FEATURE                    Location/Qualifiers
source                     1..1341
                           mol_type = protein
                           organism = Streptococcus salivarius
SEQUENCE: 65
MIDGKYYYVN EDGSHKENFA ITVNGQLLYF GKDGALTSSS TYSFTPGTTN IVDGFSINNR    60
AYDSSEASFE LIDGYLTADS WYRPASIIKD GVTWQASTAE DFRPLLMAWW PNVDTQVNYL   120
NYMSKVFNLD AKYSSTDKQE TLKVAAKDIQ IKIEQKIQAE KSTQWLRETI SAFVKTQPQW   180
NKETENYSKG GGEDHLQGGA LLYVNDSRTP WANSDYRRLN RTATNQTGTI DKSILDEQSD   240
PNHMGGFDFL LANDVDLSNP VVQAEQLNQI HYLMNWGSIV MGDKDANFDG IRVDAVDNVD   300
ADMLQLYTNY FREYYGVNKS EANALAHISV LEAWSLNDNH NDKTDGAAL AMENKQRLAL   360
LFSLAKPIKE RTPAVSPLYN NTFNTTQRDE KTDWINKDGS KAYNEDGTVK QSTIGKYNEK   420
YGDASGNYVF IRAHDNNVQD IIAEIIKKEI NPKSDGFTIT DAEMKQAFEI YNKDMLSSDK   480
KYTLNNIPAA YAVMLQNMET ITRVYYGDLY TDDGHYMETK SPYYDTIVNL MKSRIKYVSG   540
GQAQRSYWLP TDGKMDNSDV ELYRTNEVYT SVRYGKDIMT ANDTEGSKYS RTSGQVTLVA   600
NNPKLNLDQS AKLNVEMGKI HANQKYRALI VGTADGIKNR TSDADAIAAG YVKETDSNGV   660
LTFGANDIKG YETFDMSGFV AVWVPVGASD NQDIRVAPST EAKKEGETLT KATEAYDSQL   720
IYEGFSNFQT IPDGSDPSVY TNRKIAENVD LFKSWGVTSF EMAPQFVSAD DGTFLDSVIQ   780
NGYAFADRYD LAMSKNNKYG SKEDLRNDAL ALHKAGIQAI ADWVPDQIYQ LPGKEVVTAT   840
RTDGAGRKIA DAIIDHSLYV ANSKSSGKDY QAKYGGEFLA ELKAKYPEMF KVNMISTGKP   900
IDDSVKLKQW KAEYFNGTNV LERGVGYVLS DEATGKYFTV TKEGNFIPLQ LTGKEKVITG   960
FSSDGKGITY FGTSGTQAKS AFVTFNGNTY YFDARGHMVT NSEYSPNGKD VYRFLPNGIM  1020
LSNAFYIDAN GNTYLYNSKG QMYKGGYTKF DVSETKDGKE SKVVKFRYFT NEGVMAKGV  1080
TVIDGFTQYF GEDGFQAKDK LVTFGKTTYY FDAHTGNGIK DTWRNINGKW YYFDANGVAA  1140
TGAQVINGQK LYFNEDGSQV KGGVVKNADG TSYKYEGFG ELVTNEFFTT DGNVWYYAGA  1200
NGKTVTGAQV INGQHLYFNA DGSQVKGGVV KNADGTYSKY NASTGERLTN EFFTGDNNW  1260
YYIGANGKSV TGEVKIGDDT YFFAKDGKQV KGQTVSAGNG RISYYGDSG KRAVSTWIEI  1320
```

```
QPGVYVYFDK NGLAYPPRVL N                                            1341

SEQ ID NO: 66          moltype =   length =
SEQUENCE: 66
000

SEQ ID NO: 67          moltype = DNA   length = 93
FEATURE                Location/Qualifiers
misc_feature           1..93
                       note = terminator sequence added to pHYT
source                 1..93
                       mol_type = other DNA
                       organism = unidentified
SEQUENCE: 67
ggttaccttg aatgtatata aacattctca aagggatttc taataaaaaa cgctcggttg  60
ccgccgggcg tttttttatgc atcgatggaa ttc                              93

SEQ ID NO: 68          moltype = AA   length = 971
FEATURE                Location/Qualifiers
source                 1..971
                       mol_type = protein
                       organism = Aspergillus clavatus
SEQUENCE: 68
AAVHSFAPST TATAAYSQHT LPSSIDNGAQ LIANIDDPLA VNAQSVCPGY KASDVQQTSR  60
GFTASLQLAG EPCNAYGIDV DSLSLSVEVL AKDRLNIQIV PTHVDSSNAS WYILPEDRVP  120
KAQASADASV SQSDFEIEWS NDPSFNIKII RKATGDALFD TADSVLVFQN QFIEFVSALP  180
EGYNLYGLGE RMAQLRLLRN ATLTTYAADV GDPIDDNIYG QHPFYLDTRY YTKDANGSYS  240
LVNTDDADAS GDYESFSHGV FLRNAHGQEV ILQSRNITWR TIGGSIDLTF YSGPTQADVT  300
KSYQLTTIGL PAMQQYSALG FHQCRWGYRS WSELEEVVNT FEQFEIPLEY IWTDIDYMRG  360
YRDFDNDQVH FPYDEGEEFL DRLHKSGRHW VPIVDSAIYI PNPDNASDAY DTYARGAKDD  420
VFIKNPDGSL YIGAVWPGFT VFPDWHNPKA AEWWSNELVT WFEKVQYDGI WIDMSEVSSF  480
CVGSCGTGNL HLNPAHPPFQ LPGEPGNIEY TYPEAFNVTN STEAASASAA SASQSSAAAA  540
TQTDVSSTTT SYLRTTPTPG VRDINYPPYV INHVQSGHDL AVHAISPNAT HVDGVQEYDV  600
HSLWGHQILN ATYQGLLEVF TEKRPFIIGR STFAGSGKWA GHWGGDNNSR WGSMFHSISQ  660
ALSFSLFGIP MFGVDTCGFN GNTDEELCNR WMQLSAFFPF YRNHNTLAAL SQEPYRWASV  720
TEEAAKTAMSI RYALLPYFYT LFHQAHTTGS TVMRALAWEF PNDPSLAAVD TQFMVGPSIL  780
VTPVLEPLAK TVKGVFPGVG KGQVWYDWYT QAAVDAKPGV NTTIPAPLGH IPVYVRGGSI  840
LPMQEPALTT RDARKTPWSL LAALDGNQTA SGQLYLDDGS SVNPSSTLNV EFAATHSSIK  900
VSAKGDWREK NSLDSVTVLG VAKEPARVTF NRRRVPPESV EYNATSQVLT VSGLQKLTPR  960
GAWAEDWILK W                                                      971

SEQ ID NO: 69          moltype = AA   length = 969
FEATURE                Location/Qualifiers
source                 1..969
                       mol_type = protein
                       organism = Neosartorya fischeri
SEQUENCE: 69
ASHSLAPSTS ATSAHAQYTL PSSIDVGAQL VANIDDPLAV DAQSVCPGYK ASNVHQTSQG  60
FTASLQLAGD PCNVYGTDVD SLSLTVDYLA KDRLNIQIVP TYVDASNASW YLLSEDLVPR  120
AQGSGVSASQ SDFDVKWSNE PSFNLKVIRK ATGDVLFDTE GSVLVFENQF IEFVSSLPEG  180
YNLYGLGERM AQLRLLRNAT LTTYAADVGD PIDSNIYGQH PFYLDTRYYT KGTNGSYSLV  240
NTDEADLSED YESFSHGVFL RNSHGQEVLL QPRNITWRTI GGSIDLTFYS GPTQADVTKS  300
YQLSTIGLPA MQQYSTLGFH QCRWGYQNWS QLEEVVNNFE RFEIPLEYIW SDIDYMLGYR  360
DFENDPERFS YDEGEEFLNK LHKSGRHYVP IVDSAIYIPN PDNASDAYEP YARGAKDDVF  420
IKNPDGTLYI GAVWPGFTVF PDWLNPKAFD YWANELVIWS KKVAFDGIWI DMSEVSSFCV  480
GSCGTGKLHL NPVHPPFQLP GEPGNIGYDY PEAFNVTNST EAASASAASA SQASAAAATQ  540
TATTSTSTSY LRTTPTPGVR DVNYPPYVIN HVQEGHDLAV HAISPNSTHA DGVQEYDVHS  600
LWGHQILNAT YYGLRQVFTE KRPFIIGRST FAGSGKWAGH WGGDNNSKWG SMFLSISQGL  660
SFSLFGIPMF GVDTCGFNGN TDEELCSRWM QLSAFFPFYR NHNVLGAIPQ EPYRWASVTQ  720
ASKAAMKIRY SILPYFYTLF HQAHTTGSTV MRALAWEFPT DPSLAAVDTQ FMVGPSIMVV  780
PVLEPLADTV KGAFPGVGKG EVVWYDWYTQT AVDAKPGVNT TIPAPLGHIP VYVRGGSILP  840
MQEPALTTRD ARNTPWSLLV ALSGNQTASG SLYLDDGTSL NPSRTLDVDF QATAWSIKVS  900
VKGTWEEKNR LDKVTVLGVG EKPSAVTFNG RNVHPGSVHY NATSKVLSVQ GLHSMTPHGA  960
WAGNWVLKW                                                         969

SEQ ID NO: 70          moltype = AA   length = 1022
FEATURE                Location/Qualifiers
source                 1..1022
                       mol_type = protein
                       organism = Neurospora crassa
SEQUENCE: 70
QHVSVVATSS GPGVLSGTVA GDSPMFTFPA SADIGPNVLP NIFDPQAVNV QSVCPGYTAA  60
NAQKTEKGLT ADLTLAGPPC NVYGNDIEHL KLTIEFQADN RINVQIQPRY TGPGNETWFI  120
LPEVLVPRPE AEPDANAARS KLEISWSNEP TFSFTVKRKE TGDVLFTTEG RVLVYEDQFI  180
EFGSSLPENY NLYGLGEVMH GFRLGNNLTR TLFAADVGDN LDANIYGNHP IYLDTRYFTK  240
DESGKLSYVS DPADKNAKYV SYTNGVFLRN AHAQEVLLRP EGITWRTLGG SIDLYFFEGP  300
FAQDIIKSYQ LSTVGLPAMQ QYWTLGFHQC RWGYSNWTVV KDVVDNFRKF GIPLETIWTD  360
IDYMKGYRDF ENDPDQFSYE EGARFLEELH KNHQYVPIV DSAIYVPNPD KPEDDYEPYH  420
RGLEADAFIM NPDGSLYIGA VWPGYTVFPD WIGAALNGTG TVGWWTDEFV RYYKKVAFDG  480
```

```
IWIDMSEVAS FCIGSCGTGN LTLNPVHPPW GLPGEPGALV LDYPEGFEKT NASEASSATS 540
VYKTQNPDPT TTASTTSTTS YLRTTPTPGV RNINYPPYVI NNFHGDIGTH ALSPNGTHHG 600
GTVDYDFHNL FGHQILHATY QALLKVFEGK RPFIIGRSTF AGSGKWAGHW GGDNYSLWAF 660
LYFSIPQALS FSIFGFPMFG VDTCGFNGNT DHELCSRWMQ LSAFFPFYRN HNVRGAISQE 720
PYVWSSVIDA SKKAMRIRYL LLPYMYTLMA QASLSGDTVM RALSWEFPQE PWLADADRQF 780
MLGSAVMVTP CLVQGANTVD GVFPGVGDGT IWYDWYTYKA ASEGVQPGEN VTIDAPLGHI 840
PVFLRGGHVI PVQEPGMTTT ESRQNEWSVI VALDGAGKAN GTLYLDDGES LEPGENVKWV 900
DFTVEKNSFR VTPQGKYLDR NSLANVTILG VAEAPLGVAI NSHLLGSASW SYDSEGKFLS 960
VTELQDNFKE GAWASNWTLS WNSASNSGSS PVQGGGRLE FSTPNLLHAA AFGILFGRMF 1020
VV                                                              1022

SEQ ID NO: 71          moltype = AA  length = 1012
FEATURE                Location/Qualifiers
REGION                 1..1012
                       note = Derived from Rasamsonia composticola.
source                 1..1012
                       mol_type = protein
                       organism = synthetic construct
SEQUENCE: 71
AIVRRNGASP SCPGYKASNV KTVDGEIVSA DLNLAGPACN VYGTDLDDLK LQVEYQSGPG 60
VRADCLLPFD VTGTVRLVDN DLTSAEQRLH VKIYDAAEQV YQVPTAVLPR PSSANIPPAK 120
SDLKFSMTND PFSFTIKRRS NGEILFDTSG HPLIFESQYL GLRTKLPDSP NIYGLGEHTG 180
SFRLPTKNYT RTLWSRDAYG TPKDTNLYGN HPVYFDYRGS NGTHGVFLLN SNGMDVDIDV 240
DSDGQYLQYN TLGGVLDFYF LSGPDPKAVA TQYAETVGKP VMMPYWGFGF HNCRYGYQDI 300
YEVAEIIANY SAANIPLETQ WTDIDYMDLR KVFTLDPYRY PLKLVQEVVS YLHKHNQHYI 360
MMVDPAVAYQ NYSAFNNGVA ADAFLKFSNG SIYQGVVWPG PTAFPDWFAP QTQEFWNSEF 420
STFFDPAHGV DIDALWIDMN EASNFCDFPC SNPAAYAAAN GDPPTPPPVR LSPPRPIPGF 480
GPDFQPTCVA TVSFDCDAQT YFGENILILG NSTTLGAGDV HMAPVMSANN YPIWQLTVQM 540
PPNGTFSYQY VRKESDGSYI YEQTNRTVTT GDCTSGTLKV SDTITTSSGP HKRSELRPLV 600
RSPFPAEDLT RRQSGSMLGL PNRNLLNPPY TIHNAAGNLS EKTINTDLIH AGGYAEYDTH 660
NLYGTMMSAT SREAMLNRRP AVRPLVITRS TFAGAGRQVG HWLGDNFADW DHYRWTIAEL 720
QEFAALFQIP MVGSDICGYD GNTTDNLCSR WVFLGAFSPF FRDHSDNQSP PHELYRTPQI 780
AAAARAAIDI RYRLLDYAYT VLWTQTQTGA PMLNPMFFEY PADSNTADLQ YQFFWGDSIM 840
VAPVTDNDST TVNVYFPKDQ FYDFYTGAPV SGEGNTVTLT DVGFDTIPLY FKGGSIVPMR 900
VRSANTTAEL RQQDFVVVIA PDSHGDATGQ LYLDDGESIN QPHTSEIQFS YRGGHFSMTG 960
KFDYDPGNVV ISQITLLGAD GAGKGGSYNS TTKVATYKVN AKLTGKFEAS LH         1012

SEQ ID NO: 72          moltype = AA  length = 984
FEATURE                Location/Qualifiers
source                 1..984
                       mol_type = protein
                       organism = Rasamsonia composticola
SEQUENCE: 72
AIVRRNGASP SCPGYKASNV KTVDGEIVSA DLNLAGPACN VYGTDLDDLK LQVEYQSEQR 60
LHVKIYDAAE QVYQVPTAVL PRPSSANIPP AKSDLKFSMT NDPFSFTIKR RSNGEILFDT 120
SGHPLIFESQ YLGLRTKLPD SPNIYGLGEH TGSFRLPTKN YTRTLWSRDA YGTPKDTNLY 180
GNHPVYFDYR GSNGTHGVFL LNSNGMDVDI DVDSDGQYLQ YNTLGGVLDF YFLSGPDPKA 240
VATQYAETVG KPVMMPYWGF GFHNCRYGYQ DIYEVAEIIA NYSAANIPLE TQWTDIDYMD 300
LRKVFTLDPY RYPLKLVQEV VSYLHKHNQH YIMMVDPAVA YQNYSAFNNG VAADAFLKFS 360
NGSIYQGVVW PGPTAFPDWF APQTQEFWNS EFSTFFDPAH GVDIDALWID MNEASNFCDF 420
PCSNPAAYAA ANGDPPTPPP VRLSPPRPIP GFGPDFQPTC VATVSFDCDA QTYFGENILI 480
LGNSTTLGAG DVHMAPVMSA NNYPIWQLTV QMPPNGTFSY QYVRKESDGS YIYEQTNRTV 540
TTGDCTSGTL KVSDTITTSS GPHKRSELRP LVRSPFPAED LTRRQSGSML GLPNRNLLNP 600
PYTIHNAAGN LSEKTINTDL IHAGGYAEYD THNLYGTMMS ATSREAMLNR RPAVRPLVIT 660
RSTFAGAGRQ VGHWLGDNFA DWDHYRWTIA ELQEFAALFQ IPMVGSDICG YDGNTTDNLC 720
SRWVFLGAFS PFFRDHSDNQ SPPHELYRTP QIAAAARAAI DIRYLLDYA YTVLWTQTQT 780
GAPMLNPMFF EYPADSNTAD LQYQFFWGDS IMVAPVTDND STTVNVYFPK DQFYDFYTGA 840
PVSGEGNTVT LTDVGFDTIP LYFKGGSIVP MRVRSANTTA ELRQQDFVVV IAPDSHGDAT 900
GQLYLDDGES INQPHTSEIQ FSYRGGHFSM TGKFDYDPGN VVISQITLLG ADGAGKGGSY 960
NSTTKVATYK VNAKLTGKFE ASLH                                      984

SEQ ID NO: 73          moltype = AA  length = 984
FEATURE                Location/Qualifiers
REGION                 1..984
                       note = Derived from Rasamsonia composticola.
source                 1..984
                       mol_type = protein
                       organism = synthetic construct
SEQUENCE: 73
AIVRRNGASP SCPGYKASNV KTVDGEIVSA DLNLAGPACN VYGTDLDDLK LQVEYQSEQR 60
LHVKIYDAAE QVYQVPTAVL PRPSSANIPP AKSDLKFSMT NDPFSFTIKR RSNGEILFDT 120
SGHPLIFESQ YLGLRTKLPD SPNIYGLGEH TGSFRLPTKN YTRTLWSRDA YGTPKDTNLY 180
GNHPVYFDYR GSNGTHGVFL LNSNGMDVDI DVDSDGQYLQ YNTLGGVLDF YFLSGPDPKA 240
VATQYAETVG KPVMMPYWGF GFHNCRYGYQ DIYEVAEIIA NYSAANIPLE TQWTDIDYMD 300
LRKVFTLDPY RYPLKLVQEV VSYLHKHNQH YIMMVDPAVA YQNYSAFNNG VAADAFLKFS 360
NGSIYQGVVW PGPTAFPDWF APQTQEFWNS EFSTFFDPAH GVDIDALWID MNEASNFCDF 420
PCSNPAAYAA ANGDPPTPPP VRLSPPRPIP GFGPDFQPTC VATVSFDCDA QTYFGENILI 480
LGNSTTLGAG DVHMAPVMSA NNYPIWQLTV QMPPNGTFSY QYVRKESDGS YIYEQTNRTV 540
TTGDCTSGTL KVSDTITTSS GPHKRSELRP LVRSPFPAED LTRRQSGSML GLPNRNLLNP 600
```

```
PYTIHNAAGN LSEKTINTDL IHAGGYAEYD THNLYGTMMS ATSREAMLNR RPAVRPLVIT    660
RSTFAGAGRQ VGHWLGDNFA DWDHYRWTIA ELQQEFAALFQ IPMVGSDICG YDGNTTDNLC   720
SRWVFLGAFS PFFRDHSDNQ SPPHELYRTP QIAAAARAAI DIRYRLLDYA YTVLWTQTQT    780
GAPMLNPMFF EYPADSNTAD LQYQFFWGDS IMVAPVTDND STTVNVYFPK DQFYDFYTGA    840
PVSGEGNTVT LTDVGFDTIP LYFKGGSIVP MRVRSANTTA ELRQQDFVVV IAPDSHGDAT    900
GQLYLDDGES INQPHTSEIQ FSYRGGHFSM TGKFDYDPGN VVISQITLLG ADSAGKGGSY    960
NSTTKVATYK VNAKLTGKFE ASLH                                          984

SEQ ID NO: 74           moltype = AA   length = 973
FEATURE                 Location/Qualifiers
source                  1..973
                        mol_type = protein
                        organism = Rasamsonia composticola
SEQUENCE: 74
FDALAGPVSS TTAAAPSAQF TVPAAADVGA NLLANIDDPN AVNAQDVCPG YTASNVQNTE    60
SGFVATLTLA GKPCNVYGTD VESLNLTVEY QAADRLNINI VPTHVDSSNQ SWYLLPENVV    120
PKPGVDAGAQ VPESDLVFSW SNEPSFNFKV IRKATGDILF DTEGSVLVFE NQFIEFASAL    180
PENYNLYGLG ERIHGLRLGN NFTATTYAAD SADPIDRNIY GTHPFYLDTR YYEVDSEHGR    240
FTLVTDNETD FSKEYLSLSH GVFLRNAHGQ EVLLRPQSIT WRTLGGSIDL YFYAGPTQAD    300
VTRSYQTSTV GLPAMQQYFT LGYHQCRWGY RNWSELADVV ANFEKFEIPL ENIWSDIDYM    360
NEYRDFENDP VRFSYSEGAK FLDQLHKSGR HYIPIVDAAI YDPNPNNDSD AYATYDRGSK    420
DDIWLKNPDG SVYIGAVWPG YTVFTDWHHP KANEWWANEL ALWHEKVAFD GIWLDMNEVS    480
SFCVGSCGTG NLTLNPVHPN FALPGEPGAV IYDYPEDFNV TNATAAASAS AASSSQAAAT    540
ATATSSSTTT SYLVTTPTPG VRNVNYPPYV INHVQEGHDL AVHAVSPNAT HVDGVQEYDV    600
HNLWGYQETN ATYHALLSIF PGKRPFIISR STFAGSGRWA GHWGGDNASK WAYMFFSIPQ    660
ALSFSLFGIP MFGVDTCGFN GNSDEELCNR WMQLSAFPPF YRNHNVLSAI PQEPYVWASV    720
IEASKSAMRI RYTLLPYLYT LFYLAHTTGS TVMRALAWEF PNDPSLAAVD RQFLLGPSLM    780
VVPVLEPQVD TVKGVFPPGVA QGQVWYDWYT QTAFDAQPGV NTTISAPLGH IPVFVRGGSV    840
LPMQQPALVT RDVRNSPWSL LVALGSDGTA SGQLYVDDGE SITPPASLHV DFVAANFSTL    900
FATARGAFKD SNTLANVTVL GVPAAPSSAV TWNNETVPSE SVSYNATSKV LVVNGLQSLT    960
RDGAWSSDWV LKW                                                      973

SEQ ID NO: 75           moltype = AA   length = 604
FEATURE                 Location/Qualifiers
source                  1..604
                        mol_type = protein
                        organism = Bifidobacterium longum
SEQUENCE: 75
MTANNLNDDW WKQAVVYQIY PRSFKDVNGD GLGDIAGVTE KMDYLKNLGV DAIWLSPFYP    60
SDLADGGYDV IDYRNVDPRL GTMEDFDAMA KAAHEAGIKV IVDIVPNHTA DKHVFFQEAL    120
AAEPGSPARD RYIFRDGRGE HGELPPNDWQ SFFGGPAWAR VADGQWYLHL FDKAQPDVNW    180
KNPDIHEEFK KTLRFWSDHG TDGFRIDVAH GLAKDLESKP LEELGREYSV VGVLNHDFSH    240
PLFDRREVHD IYREWRKVFN EYDPPRFAVA EAWVVPEHQH LYASMDELGQ SFNFDFAQAN    300
WYADEFREAI AAGLKAAAET GGSTTTWVMN NHDVPRSPSR YGLPQIKGAP YHQLPHDWLL    360
RNGTTYPEDR ELGTRRARAA ALMELGLPGA AYIYQGEELG LFEVADIPWD HLEDPTAFHT    420
AQATMDKGRD GCRVPLPWTA ADEPALADFS RPTPADDGTG ENHVPLCAAG QFGTGASFGF    480
SPATRAEGVT PAADPHLPQP LWFKDYAVDV EQADPDSMLA LYRAALAIRQ ESLTATRDTT    540
AEQVDMGDDV VAYTRAAVGG RVFTSITNFG NAPVALPDGS VVLASGPLTP EAQLPTDTSA    600
WVVQ                                                                604

SEQ ID NO: 76           moltype = AA   length = 604
FEATURE                 Location/Qualifiers
source                  1..604
                        mol_type = protein
                        organism = Bifidobacterium longum
SEQUENCE: 76
MTANNLNDDW WKQAVVYQIY PRSFKDVNGD GLGDIAGVTE KMDYLKNLGV DAIWLSPFYP    60
SDLADGGYDV IDYRNVDPRL GTMEDFDAMA KAAHEAGIKV IVDIVPNHTA DKHVFFQEAL    120
AAEPGSPARD RYIFRDGRGE HGELPPNDWQ SFFGGPAWAR VADGQWYLHL FDKAQPDVNW    180
KNPDIHEEFK KTLRFWSDHG TDGFRIDVAH GLAKDLESKP LEELGREYSV VGVLNHDFSH    240
PLFDRREVHD IYREWRKVFN EYDPPRFAVA EAWVVPEHQH LYASMDELGQ SFNFDFAQAN    300
WYADEFREAI AAGLKAAAET GGSTTTWVMN NHDVPRSPSR YGLPQIKGAP YHQLPHDWLL    360
RNGTTYPEDR ELGTRRARAA ALMELGLPGA AYIYQGEELG LFEVADIPWD HLEDPTAFHT    420
AQATMDKGRD GCRVPLPWTA ADEPALADFS RPTPADDGTG ENHVPLCAAG QFGTGASFGF    480
SPATRAEGVT PAADPHLPQP LWFKDYAVDV EQADPDSMLA LYRAALAIRQ ESLTATRDTT    540
AEQVDMGDDV VAYTRAAVGG RVFTSITNFG NAPVALPDGS VVLASGPLTP EAQLPTDTSA    600
WVVQ                                                                604

SEQ ID NO: 77           moltype = AA   length = 604
FEATURE                 Location/Qualifiers
source                  1..604
                        mol_type = protein
                        organism = Bifidobacterium longum
SEQUENCE: 77
MTANNLNDDW WKQAVVYQIY PRSFKDVNGD GLGDIAGVTE KMDYLKNLGV DAIWLSPFYP    60
SDLADGGYDV IDYRNVDPRL GTMDDFDAMA EAAHEAGIKV IVDIVPNHTA DKHVFFKEAL    120
ASEPGSPARD RYIFRDGRGE HGELPPNDWQ SFFGGPAWAR VPDGQWYLHL FDKAQPDVNW    180
KNPDIHEEFK KTLRFWSDHG TDGFRIDVAH GLAKDLESKP LEELGREYSV VGVLNHDFSH    240
PLFDRREVHD IYREWRKVFN EYTPPRFAVA EAWVVPEHQH LYASMDELGQ SFNFDFAQAN    300
```

```
WYADEFRKAI  AAGLKAAAET  GGSTTTWVMN  NHDVPRSPSR  YGLPQVKGAP  YHQLPHDWLL   360
RDGTTYPENR  ELGTRRARAA  ALMELGLPGA  AYIYQGEELG  LFEVADIPWD  HLEDPTAFHT   420
TRNTMDKGRD  GCRVPLPWTA  ADEPALADFS  RPAPADDGTG  ENHVPLCAAG  QFGTGASFGF   480
SPAVRADGVT  PAADPHLPQP  LWFKDYAVDV  EQADPDSMLA  LYRAALAIRQ  ESLTATRDTT   540
AEQVDMGDDV  VAYTRAAVGG  RVFTSITNFG  NAPVALPDGS  VVLASGPLTP  EGQLPTDTSA   600
WVIK                                                                    604

SEQ ID NO: 78           moltype = AA  length = 585
FEATURE                 Location/Qualifiers
source                  1..585
                        mol_type = protein
                        organism = Bifidobacterium pseudolongum
SEQUENCE: 78
MTLNNTHDDW  WKQAVVYQVY  PRSFRDANGD  GLGDIAGITS  RIPYLRQLGV  DALWLSPFYP    60
SELADGGYDV  IDYRNVDPRL  GTLDDFDAMV  AAAHSAGLKV  VVDIVPNHTS  NMHPWFQEAL   120
ASAPGSPARD  RYIFRDGEGA  HGELPPNNWQ  SLFGGPAWEA  AGDGQWYLHL  FTKEQPDLNW   180
KNPDVHEDFR  TTLRFWSDRG  VDGFRIDVAH  GLAKDLSEP   LKDLERFPVG  GNPVPGHPLW   240
DRPEVHEIYR  EWNKVFNEYD  PPRFAVGEAW  VPAEHQHLYA  SKDELGQVFN  FEFAKANWFA   300
DDFRLAIEEG  LASADESKST  TTWVMSNHDV  PRHVSRYGLP  QVHTRGYHEL  PNDWLLRNGT   360
TYIEDRELGT  RRARAAILME  LGLPGSVYVY  QGEELGLPEV  ATIPWDHLED  PVAFNTDHSD   420
AAKGRDGCRV  PLPWSAQDMP  QPAPWDPEFG  TGASFGFSEH  AGGRASADPH  LPQPLWYAGY   480
AADMEDTDPA  SMLNLYRRAM  HWRQEHLTPT  GDTSLTWLSP  QSFADCGDDV  VAYARPLADD   540
SGDRFVCIVN  FGAASIELPH  GDVMMRSIPF  DGYQLPADAA  VWMRI                   585

SEQ ID NO: 79           moltype = AA  length = 601
FEATURE                 Location/Qualifiers
source                  1..601
                        mol_type = protein
                        organism = Bifidobacterium thermophilum
SEQUENCE: 79
MAERKSPQSA  QESTASDRAA  AAWWHQAVVY  QVYPRSFKDT  TGSGLGDIAG  VTSRIGYLKQ    60
LGVDAIWLSP  FYPSQLADGG  YDVDDYRNVD  PKLGTMDDFD  KLAKTAHEAG  IKIVVDIVPN   120
HSSNLHPWFK  AALAAGPGSP  ERDRYIFRDG  RGEHGLPPT   DWVSHFGGPA  WTRVPDGQWY   180
LHLFTVEQPD  WNWKNPDVQA  DFIKTLRFWL  DHGADGFRVD  VAHGLCKDLD  RDNLDQWSVT   240
PPSLPADGSH  PLYDRDDVHQ  IYREWRKVFN  EYDPPAFAVA  EAWVNPARQY  LYASDDELGQ   300
VFNFEFAKKN  WVRDDMHQAI  EEGLEAARRS  GSTATWVMSN  HDVPRHASRY  ALPQVPSTRH   360
HQLAHDWLLR  DGTSYHEDRE  AGTRRARAAI  LMELALPGSA  YLYQGEELGL  FEVADIPWNK   420
LEDPTARNSE  RAAKDKGRDG  CRVPLPWVAA  DGVEGSFGFS  PRVKSVGAGV  SADQAGQPSE   480
PAHLPQPAWF  ADFAADRESA  QPESMLNLYR  RALALRHELM  PADTTLTWLD  EDRPSDAPDG   540
ADGQHGGVIA  YRRSNGWASV  TNFGAEPVAL  PAGEVLLTSG  ELCSDGRLPQ  DTTVWLRLNQ   600
D                                                                       601

SEQ ID NO: 80           moltype = AA  length = 662
FEATURE                 Location/Qualifiers
source                  1..662
                        mol_type = protein
                        organism = Bifidobacterium breve
SEQUENCE: 80
MYFHINHLHD  TVVINVISKH  GFTVAVRVLL  NPITTNPQQS  GATHHVSHTI  THAQKGIGMT    60
ANNLNDDWWK  QAVVYQIYPR  SFKDVNGDGI  GDIAGVTEKM  DYLKNLGVDA  IWLSPFYPSD   120
LADGGYDVID  YRNVDPRLGT  MDDFDAMAKA  AHEAGIKVIV  DIVPNHTADK  HVFFKEALAA   180
EPGSPARDRY  IFRDGRGEHG  ELPPNDWQSF  FGGPAWARVA  DGQWYLHFD   KAQPDVNWKN   240
PDIHEEFKKT  LRFWSDHGTD  GFRIDVAHGL  AKDLESKPLE  ELGREYSVVG  VLNHDFSHPL   300
FDRREVHDIY  REWRKVFNEY  DPPRFAVAEA  WVVPEHQHLY  ASMDELGQSF  NFDFAQASWY   360
ADEFRAAIAA  GLKAAAETGG  STTTWVMNNH  DVPRSPSPYH  LPQVKGAPYH  QLPHDWLLRN   420
GTTYPEDREL  GTRRARAAAL  MELGLPGAAY  IYQGEELGLF  EVADIPWDRL  EDPTAFHTAQ   480
ATMDKGRDGC  RVPIPWTAAN  EPTLADFSRP  IPADDGTGEN  HVPLCAAGQF  GTGASFGFSP   540
ATRAEGVTPA  ADPHLPQPLW  FKDYAVDVEQ  APDPSMLALY  HAALAIRQES  LTATRDTTAE   600
QVDMGPDVVA  YTRAAVGGRT  FTSITNFGTE  PVELPGGSVV  LTSGPLTPDG  QLPTDTSAWV   660
IK                                                                      662

SEQ ID NO: 81           moltype = AA  length = 606
FEATURE                 Location/Qualifiers
source                  1..606
                        mol_type = protein
                        organism = Bifidobacterium breve
SEQUENCE: 81
MTTFNRAIIP  DAIRTNGATP  NPWWSNAVVY  QIYPRSFQDT  NGDGLGDLKG  ITSRLDYLAD    60
LGVDVLWLSP  VYRSPQDDNG  YDISDYRDID  PLFGTLDDMD  ELLAEAHKRG  LKIVMDLVVN   120
HTSDEHAWFE  ASKDKDDPHA  DWYWWRPARP  GHEPGTPGAE  PNQWGSYFGG  SAWEYSPERG   180
EYYLHQFSKK  QPDLNWENPA  VRRAVYDMMN  WWLDRGIDGF  RMDVITLISK  RTDANGRLPG   240
EYGSELHDLP  VGEEGYSSPN  PFCADGPRQD  EFLAEMRREV  FDGRDGFLTV  GEAPGITAER   300
NEHITNPANG  ELDMLFLFEH  VDFDCDGVKW  KPLPLDLGPK  KRIMAGYQTA  VENVGWASLF   360
TGNHDQPRVV  SRWGDDSSEE  SRVRSAKALG  LMLMHMRGTP  YVYQGEELGM  TNAHFTSLDQ   420
YRDLESLNAY  RQRVEEAKVQ  SPESMMAGIA  ARGRDNSRTP  MQWDGSAYAG  FTAPDAATEP   480
WISVNPNHAE  INAAGEFDDP  DSVYAFYKKL  IALRHNSSIV  AAGEWRLIDA  DDAHVYAFTR   540
TLGNERLLVV  VNLSGRTVDL  PRESTELIAG  GVTEPDIILS  TYDAPHTVVS  LANRELDPWE   600
AAAVQL                                                                  606
```

What is claimed is:

1. A polynucleotide comprising a nucleotide sequence encoding a non-native glucosyltransferase,
   wherein the non-native glucosyltransferase comprises at least two amino acid substitutions at positions corresponding with amino acid residues Gln-588, Phe-607, or Arg-741 of SEQ ID NO:62,
   wherein the non-native glucosyltransferase synthesizes insoluble alpha-glucan comprising 1,3-linkages,
   wherein the non-native glucosyltransferase has:
   (i) an insoluble alpha-glucan yield that is higher than the insoluble alpha-glucan yield of a second glucosyltransferase that only differs from the non-native glucosyltransferase at the substitution positions, and/or a leucrose yield that is lower than the leucrose yield of the second glucosyltransferase;
   wherein the non-native glucosyltransferase comprises an amino acid sequence that has at least 90% sequence identity to the amino acid sequence of residues 55-960 of SEQ ID NO:4 or the amino acid sequence of residues 54-957 of SEQ ID NO: 65.

2. The polynucleotide of claim 1, wherein one or more regulatory sequences are operably linked to the nucleotide sequence.

3. The polynucleotide of claim 2, wherein said one or more regulatory sequences include a promoter sequence.

4. The polynucleotide of claim 1, wherein the non-native glucosyltransferase comprises amino acid substitutions at positions corresponding with amino acid residues Gln-588, Phe-607 and Arg-741 of SEQ ID NO: 62.

5. The polynucleotide of claim 1, wherein:
   (i) the amino acid substitution at the position corresponding with amino acid residue Gln-588 is with a Leu, Ala, or Val residue;
   (ii) the amino acid substitution at the position corresponding with amino acid residue Phe-607 is with a Trp, Tyr, or Asn residue; and/or
   (iii) the amino acid substitution at the position corresponding with amino acid residue Arg-741 is with a Ser or Thr residue.

6. The polynucleotide of claim 1, wherein the non-native glucosyltransferase further comprises at least one amino acid substitution at a position corresponding with amino acid residue Ala-510 and/or Asp-948 of SEQ ID NO: 62.

7. The polynucleotide of claim 6, wherein:
   (i) the amino acid substitution at the position corresponding with amino acid residue Ala-510 is with an Asp, Glu, Ile, or Val residue; and/or
   (ii) the amino acid substitution at the position corresponding with amino acid residue Asp-948 is with a Gly, Val, or Ala residue.

8. The polynucleotide of claim 1, wherein the non-native glucosyltransferase further comprises at least one amino acid substitution at a position corresponding with amino acid residue Ser-631, Ser-710, Arg-722, and/or Thr-877 of SEQ ID NO:62.

9. The polynucleotide of claim 8, wherein:
   (i) the amino acid substitution at the position corresponding with amino acid residue Ser-631 is with a Thr, Asp, Glu, or Arg residue;
   (ii) the amino acid substitution at the position corresponding with amino acid residue Ser-710 is with a Gly, Ala, or Val residue;
   (iii) the amino acid substitution at the position corresponding with amino acid residue Arg-722 is with a His or Lys residue; and/or
   (iv) the amino acid substitution at the position corresponding with amino acid residue Thr-877 is with a Lys, His, or Arg residue.

10. The polynucleotide of claim 1, wherein the non-native glucosyltransferase further comprises at least one amino acid substitution at a position corresponding with amino acid residue Val-1188, Met-1253, and/or Gln-957 of SEQ ID NO:62.

11. The polynucleotide of claim 10, wherein:
    (i) the amino acid substitution at the position corresponding with amino acid residue Val-1188 is with a Glu or Asp residue;
    (ii) the amino acid substitution at the position corresponding with amino acid residue Met-1253 is with an Ile, Leu, Ala, or Val residue; and/or
    (iii) the amino acid substitution at the position corresponding with amino acid residue Gln-957 is with a Pro residue.

12. The polynucleotide of claim 1, wherein the non-native glucosyltransferase comprises an amino acid sequence that has at least 95% sequence identity to the amino acid sequence of residues 55-960 of SEQ ID NO: 4 or the amino acid sequence of residues 54-957 of SEQ ID NO:65.

13. The polynucleotide of claim 1, wherein the non-native glucosyltransferase comprises an amino acid sequence that has at least 90% sequence identity to the amino acid sequence of SEQ ID NO:4 or the amino acid sequence of SEQ ID NO:65.

14. The polynucleotide of claim 13, wherein the non-native glucosyltransferase comprises an amino acid sequence that has at least 95% sequence identity to the amino acid sequence of SEQ ID NO:4 or the amino acid sequence of SEQ ID NO:65.

15. The polynucleotide of claim 1, wherein the non-native glucosyltransferase comprises amino acid substitutions at positions corresponding with amino acid residues Ala-510, Gln-588, Phe-607, Arg-741 and Asp-948 of SEQ ID NO:62.

16. The polynucleotide of claim 15, wherein:
    (i) the amino acid substitution at the position corresponding with amino acid residue Ala-510 is with an Asp, Glu, Ile, or Val residue;
    (ii) the amino acid substitution at the position corresponding with amino acid residue Gln-588 is with a Leu, Ala, or Val residue;
    (iii) the amino acid substitution at the position corresponding with amino acid residue Phe-607 is with a Trp, Tyr, or Asn residue;
    (iv) the amino acid substitution at the position corresponding with amino acid residue Arg-741 is with a Ser or Thr residue; and/or
    (v) the amino acid substitution at the position corresponding with amino acid residue Asp-948 is with a Gly, Val, or Ala residue.

17. The polynucleotide of claim 15, wherein:
    (i) the amino acid substitution at the position corresponding with amino acid residue Ala-510 is with an Asp residue;
    (ii) the amino acid substitution at the position corresponding with amino acid residue Gln-588 is with a Leu residue;
    (iii) the amino acid substitution at the position corresponding with amino acid residue Phe-607 is with a Trp residue;
    (iv) the amino acid substitution at the position corresponding with amino acid residue Arg-741 is with a Ser residue; and/or (v) the amino acid substitution at the position corresponding with amino acid residue Asp-948 is with a Gly residue.

18. The polynucleotide of claim 17, wherein:
(i) the amino acid substitution at the position corresponding with amino acid residue Ala-510 is with an Asp residue;
(ii) the amino acid substitution at the position corresponding with amino acid residue Gln-588 is with a Leu residue;
(iii) the amino acid substitution at the position corresponding with amino acid residue Phe-607 is with a Trp residue;
(iv) the amino acid substitution at the position corresponding with amino acid residue Arg-741 is with a Ser residue; and
(v) the amino acid substitution at the position corresponding with amino acid residue Asp-948 is with a Gly residue.

19. The polynucleotide of claim 15, wherein the non-native glucosyltransferase further comprises amino acid substitutions at positions corresponding with amino acid residue Val-1188 and Met-1253 of SEQ ID NO: 62.

20. The polynucleotide of claim 19, wherein:
(i) the amino acid substitution at the position corresponding with amino acid residue Val-1188 is with a Glu or Asp residue; and
(ii) the amino acid substitution at the position corresponding with amino acid residue Met-1253 is with an Ile, Leu, Ala, or Val residue.

\* \* \* \* \*